United States Patent
Housley et al.

(10) Patent No.: US 11,013,917 B2
(45) Date of Patent: May 25, 2021

(54) METHOD AND APPARATUS FOR CLOSE-FIELD ELECTROPORATION

(71) Applicant: NEWSOUTH INNOVATIONS PTY LIMITED, New South Wales (AU)

(72) Inventors: Gary David Housley, New South Wales (AU); Matthias Klugmann, New South Wales (AU); Jeremy Pinyon, New South Wales (AU)

(73) Assignee: NEWSOUTH INNOVATIONS PTY LIMITED, Sydney (AU)

( * ) Notice: Subject to any disclaimer, the term of this patent is extended or adjusted under 35 U.S.C. 154(b) by 681 days.

(21) Appl. No.: 14/895,207

(22) PCT Filed: Jun. 23, 2014

(86) PCT No.: PCT/AU2014/000647
§ 371 (c)(1),
(2) Date: Dec. 1, 2015

(87) PCT Pub. No.: WO2014/201511
PCT Pub. Date: Dec. 24, 2014

(65) Prior Publication Data
US 2016/0129246 A1    May 12, 2016

(30) Foreign Application Priority Data
Jun. 21, 2013  (AU) .............................. 2013902263

(51) Int. Cl.
*A61N 1/30* (2006.01)
*A61N 1/32* (2006.01)
(Continued)

(52) U.S. Cl.
CPC .............. *A61N 1/30* (2013.01); *A61K 38/185* (2013.01); *A61N 1/327* (2013.01); *A61N 1/0541* (2013.01)

(58) Field of Classification Search
None
See application file for complete search history.

(56) References Cited

U.S. PATENT DOCUMENTS

| 5,702,359 A | 12/1997 | Hofmann et al. |
| 6,009,345 A | 12/1999 | Hofmann |

(Continued)

FOREIGN PATENT DOCUMENTS

| WO | 98000014 | 1/1998 |
| WO | 03063543 | 7/2003 |

(Continued)

OTHER PUBLICATIONS

Choi et al., Intracellular Protein Delivery and Gene Transfection by Electroporation Using a Microneedle Electrode Array. Small. Apr. 10, 2012; 8(7): 1081-1091 (Year: 2012).*

(Continued)

*Primary Examiner* — Christopher M Babic
*Assistant Examiner* — Arthur S Leonard
(74) *Attorney, Agent, or Firm* — Michael Best & Friedrich LLP

(57) ABSTRACT

The present invention relates to improved methods for transfecting one or more cells within a target region with an agent by electroporation. The method comprises exposing one or more cells to the agent and to a close electric field created between an anode or anode array and a cathode or cathode array in the target region for sufficient time to allow at least some of the agent to enter said one or more cells.

20 Claims, 23 Drawing Sheets

(51) Int. Cl.
  *A61K 38/18*  (2006.01)
  *A61N 1/05*  (2006.01)

(56)  References Cited

U.S. PATENT DOCUMENTS

| | | | |
|---|---|---|---|
| 6,546,934 B1 * | 4/2003 | Ingle | A61B 18/1482 |
| | | | 128/898 |
| 6,947,791 B2 * | 9/2005 | Zhang | A61N 1/0424 |
| | | | 604/20 |
| 6,972,013 B1 | 12/2005 | Zhang et al. | |
| 7,315,763 B2 | 1/2008 | Kuzma et al. | |
| 7,317,944 B1 | 1/2008 | Overstreet | |
| 7,319,906 B2 | 1/2008 | Kuzma et al. | |
| 7,340,308 B1 | 3/2008 | Clopton et al. | |
| 7,349,744 B2 | 3/2008 | Dadd et al. | |
| 7,367,992 B2 | 5/2008 | Dadd | |
| 7,406,352 B2 | 7/2008 | Gibson | |
| 7,451,000 B2 | 11/2008 | Gibson et al. | |
| 7,879,610 B1 | 2/2011 | Heller et al. | |
| 2003/0203482 A1 | 10/2003 | Kil et al. | |
| 2005/0052630 A1 | 3/2005 | Smith et al. | |
| 2005/0281786 A1 | 12/2005 | Poulsen et al. | |
| 2006/0089674 A1 | 4/2006 | Walters et al. | |
| 2006/0247735 A1 | 11/2006 | Honert | |
| 2008/0214986 A1 | 9/2008 | Ivorra et al. | |
| 2009/0125011 A1 * | 5/2009 | Behzadian | A61B 18/1477 |
| | | | 606/33 |
| 2011/0106221 A1 | 5/2011 | Neal, II et al. | |
| 2012/0046598 A1 | 2/2012 | Kardos et al. | |
| 2012/0071957 A1 * | 3/2012 | Carter | A61N 1/0541 |
| | | | 607/137 |
| 2012/0089009 A1 | 4/2012 | Omary et al. | |
| 2012/0191032 A1 | 7/2012 | Housley | |
| 2013/0066296 A1 | 3/2013 | Broderick et al. | |
| 2014/0194807 A1 | 7/2014 | Housley | |

FOREIGN PATENT DOCUMENTS

| | | | | |
|---|---|---|---|---|
| WO | 2007137335 | | 12/2007 | |
| WO | 2010008627 | | 1/2010 | |
| WO | WO-2011006204 A1 * | 1/2011 | | A61F 11/00 |

OTHER PUBLICATIONS

Cochlear Ltd., (Product Reference Guide, Cochlear™ Nucleus® Electrode Portfolio, p. 1-2, published on-line Dec. 11, 2012) (Year: 2012).*
Heller, R. et al., Electrically Mediated Delivery of Plasmid DNA to the Skin, Using a Multielectrode Array, Human Gene Therapy, Mar. 2010, vol. 21, pp. 357-362.
Lin, F. et al., "Optimization of Electroporation-Enhanced Intradermal Delivery of DNA Vaccine Using a Minimally Invasive Surface Device", Human Gene Therapy Methods, Jun. 2012, vol. 23, pp. 157-168.
Gubbels, S. et al., "Functional auditory hair cells produced in the mammalian cochlea by in utero gene transfer", Nature, Sep. 25, 2008, vol. 455 (7212), pp. 537-541.
International Search Report for PCT/AU2014/000647 dated Jul. 21, 2014 (4 pages).
International Search Report and Written Opinion for Application No. PCT/AU2010/000899 dated Sep. 2, 2010 (8 pages).
International Preliminary Report on Patentability for Application No. Application No. PCT/AU2010/000899 dated Jun. 7, 2011 (3 pages).
Badi et al., "A Technique for Implantation of a 3-Dimensional Penetrating Electrode Array in the Modiolar Nerve of Cats and Humans",Arch Otolaryngol Head Neck Surg., 2002; 128(9):1019-1025.
Biomed Brown University,"Understanding the cochlear implant", May, 2006. pp. 1-5.<http://biomed.brown.edu/Courses/BI108/2006-108websites/group10cochlearimplant/pages/electrodearray.Html>.
Brigande,et al., "Electroporation-mediated gene transfer to the developing mouse inner ear", Methods Mal Biol, 2009; 493:125-139.
Cochlear, "Cochlear Nucleus CI422 with Slim Straight—Technical Specifications", (12 pages).
Cochlear, "Nucleus CI512 cochlear implant—Technical Specifications",(42 pages).
Cogan, "Neural Stimulation and Recording Electrodes", Annual Review of Biomedical Engineering, 2008; 10:275-309.
CUY21EDIT, "In Vivo Square Wave Electroporator",[retrieved from internet on Sep. 23, 2016] <URL: http://www.sonidel.com/product_info.php?products_id=32> published on Apr. 20, 2008 per Wayback Machine. The document D1 (WO 2014/201511) discloses the use of In Vivo Square Wave Electroporator CUYEDIT in [00193] for optimization of electroporation parameters.
Dabdoub et al., "Sox2 signaling in prosensory domain specification and subsequent hair cell differentiation in the developing cochlea", Proc Natl Acad Sci USA., 2008; 105(47):18396-401.
Kawamoto et al., "Antioxidant Gene Therapy Can Protect Hearing and Hair Cells from Ototoxicity", Molecular Therapy, 2004; 9(2):173-181.
Keithley et al., "Effects of a hair cell transcription factor Bm-3.1, gene deletion on homozygous and heterozygous mouse cochleas in adulthood and aging", Hearing Research, 1999; 134(1-2):71-76.
Leake et al., "Effects of Brain-Derived Neurotrophic Factor (BDNF) and Electrical Stimulation on Survival and Function of Cochlear Spiral Ganglion Neurons in Deafened, Developing Cats",J Assoc Res Otolaryngol, 2013; 14(2):187-211.
Liu et al., "Promoter effects of adeno-associated viral vector for transgene expression in the cochlea in vivo", Experimental and Molecular Medicine, 2007; 39(2):170-175.
Mencia, Angeles, et al., "Mutations in the seed region of human miR-96 are responsible for nonsyndromic progressive hearing loss", Nature Genetics, 2009; 41(5):609-613.
Mencia, Angeles, et al., "Mutations in the seed region of human miR-96 are responsible for nonsyndromic progressive hearing loss", Nature Genetics, 2009; 41(5), Supporting Information, (15 pages).
Merrill et al., "Electrical stimulation of excitable tissue: design of efficacious and safe protocols",Journal of Neuroscience Methods, 2005; 141(2):171-198.
Paasche et al., "Technical Report: Modification of a Cochlear Implant Electrode for Drug Delivery to the Inner Ear", Otology & Neurology, 2003; 24(2):222-227.
Pinyon et al., "Close-Field Electroporation Gene Delivery Using the Cochlear Implant Electrode Array Enhances the Bionic Ear",Science Translational Medicine, 2014; 6(233): 1-12.
Prado-Guitierrez et al., "Effect of interphase gap and pulse duration on electrically evoked potentials is correlated with auditory nerve survival",Hear Res., 2006; 215(1-2):47-55.
Rols, "Electropermeabilization, a physical method for the delivery of therapeutic molecules into cells",Biochim Biophys Acta., 2006; 1758(3):423-8.
Ryan A.F., "Declaration under 37 C.F.R s1.132 for U.S. Appl. No. 14/145,673", filed Aug. 27, 2015.
Salt, "Chapter 6: The Cochlear Fluids: Perilymph and Endolymph", In: Neurobiology of Hearing: The Cochlea, Altschuler, et al, Editors, Raven Press, New York, NY, (1986), 109-122.
Satkauskas, et al., "Mechanisms of in Vivo DNA Electrotransfer: Respective Contributions of Cell Electropermeabilization and DNA Electrophoresis",Molecular Therapy, 2002; 5(2):133-40.
Stone et al., "Adeno-associated Virus-Mediated Gene Transfer to Hair Cells and Support Cells of the Murine Cochlea", Molecular Therapy, 2005; 11(6):843-884.
Thorne et al., "Cochlear fluid space dimensions for six species derived from reconstructions of three-dimensional magnetic resonance images", The Laryngoscope, 1999; 109(10): 1661-1668.
Van Der Wees et al., "Hearing loss following Gata3 haploinsufficiency is caused by cochlear disorder", Neurobiology of Disease, 2004; 16(1):169-178.
Wang,et al., "ABSTRACT: Gene Transfer to the Developing Mouse Inner Ear by In Vivo Electroporation", J Vis Exp., 2012;64:1-7.
Xu et al., "CMV-β-Actin promoter directs higher expression from an adeno-associated viral vector in the liver than the cytomegalovirus

(56) References Cited

OTHER PUBLICATIONS or elongation factor 1 alpha promoter and results in therapeutic levels of human factor X in mice", Human Gene Therapy, 2001; 12(5): 563-573.

Abed, AA et al., "Computational simulation expands understanding of electrotransfer-based gene augmentation for enhancement of neural interfaces," Frontiers in Neuroscience Aug. 6, 2019, vol. 13, Artivle 691, 12 pages.

Browne, CJ et al., "Mapping of bionic array electric field focusing in plasmid DNA-based gene electrotransfer," Gene Therapy, 2016, 23(4): pp. 369-79.

Escoffre, JM et al., "Electromediated formation of DNA complexes with cell membranes and its consequences for gene delivery," Biochim. Biophys. Acta 1808, 2011, pp. 1538-1543.

Housley, GD et al., "Cochlear implant close-field electroporation," Handbook of Electroporation, 2016, 20 pages.

Ita, K., "Perspectives on transdermal electroporation," Pharmaceutics, 8:9, 2016,14 pages.

Pinyon, JL et al., "Close-field electroporation gene delivery using the cochlear implant electrode array enhances the bionic ear," Science Translational Medicine, 6, 2014, 21 pages.

Pinyon, JL et al., "Neurotrophin gene augmentation by electrotransfer to improve cochlear implant hearing outcomes," Hearing Research 380, 2019, 137-149.

Rosazza, C et al., "Endocytosis and endosomal trafficking of DNA after gene electrotransfer in vitro," Mol. Ther. Nucleic Acids 5, 2016, 11 pages.

\* cited by examiner

Figure 1
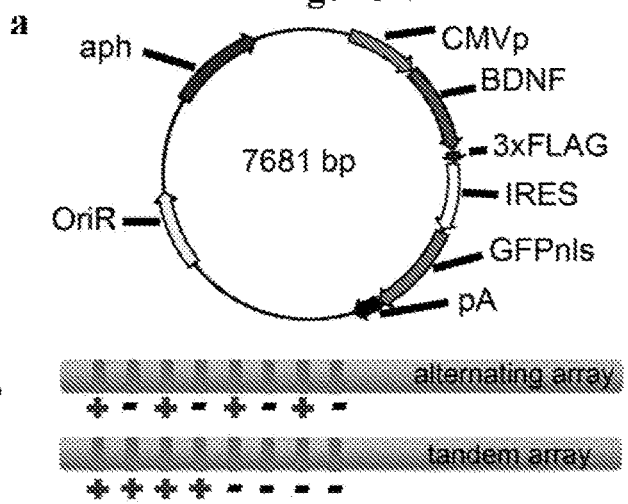
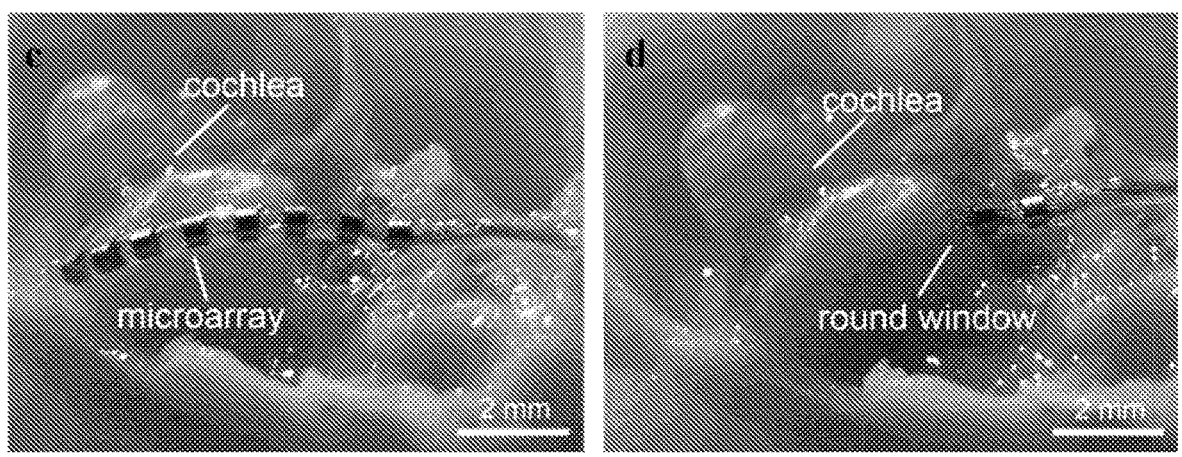
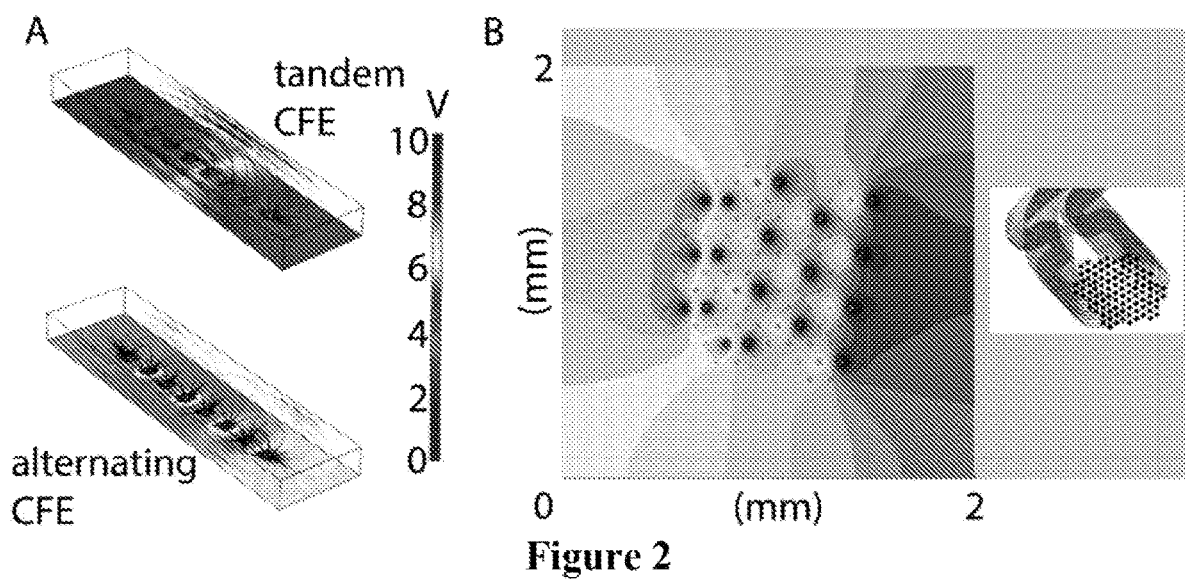
Figure 2

Figure 3
Microarray electrode congifurations
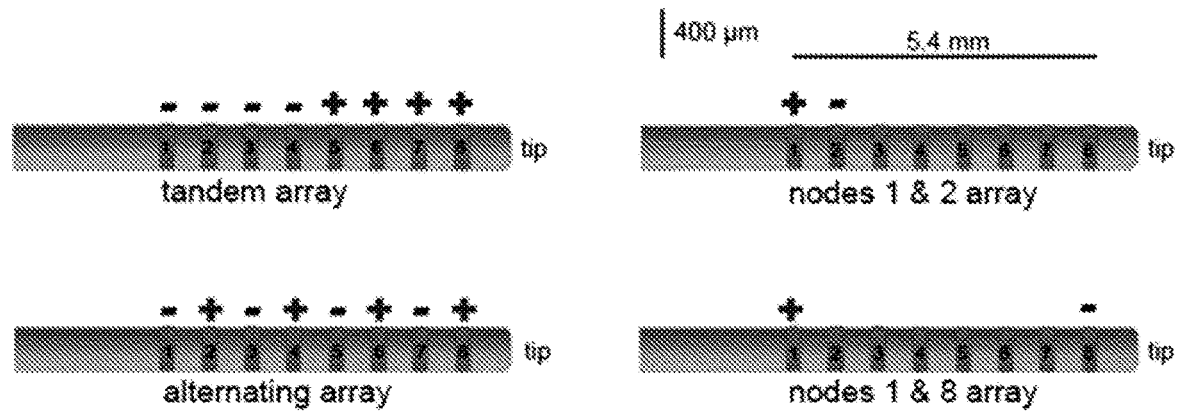
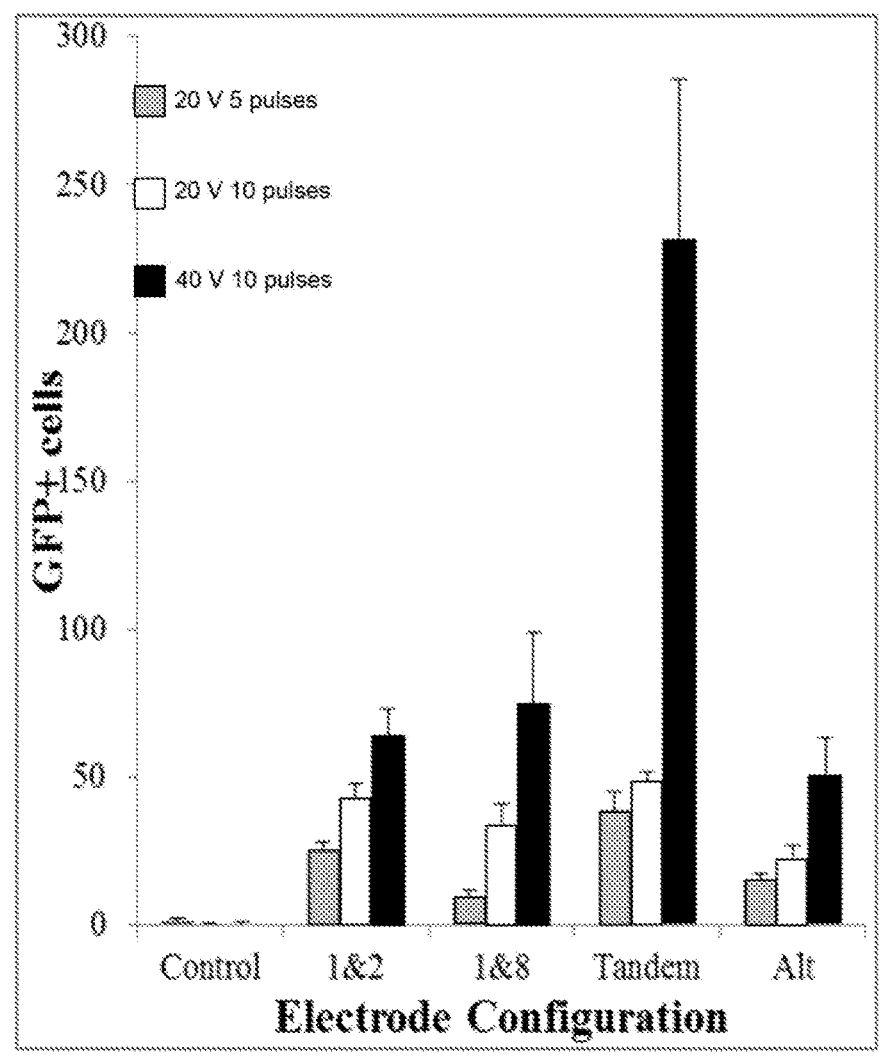
Figure 4

Figure 8
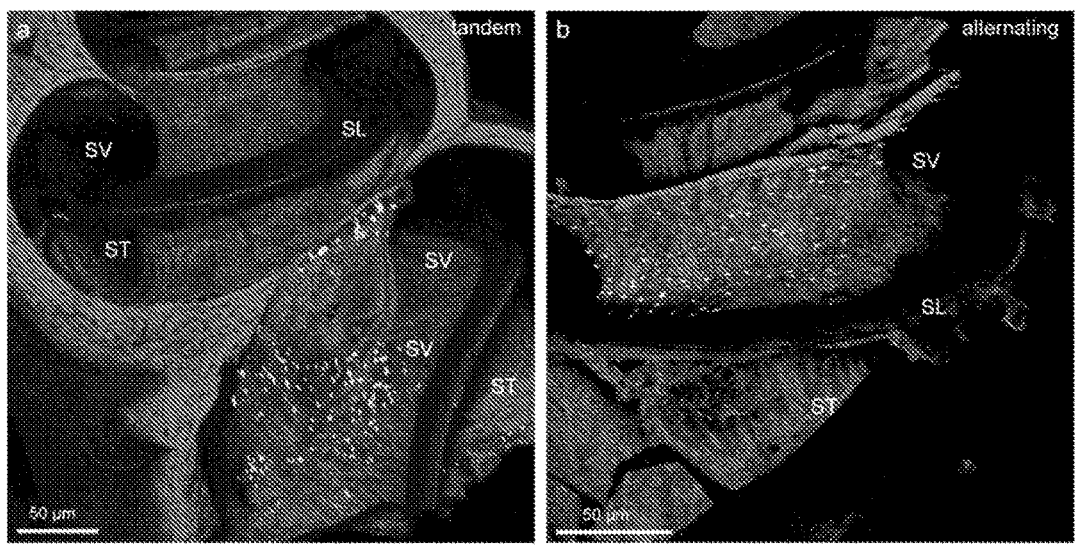
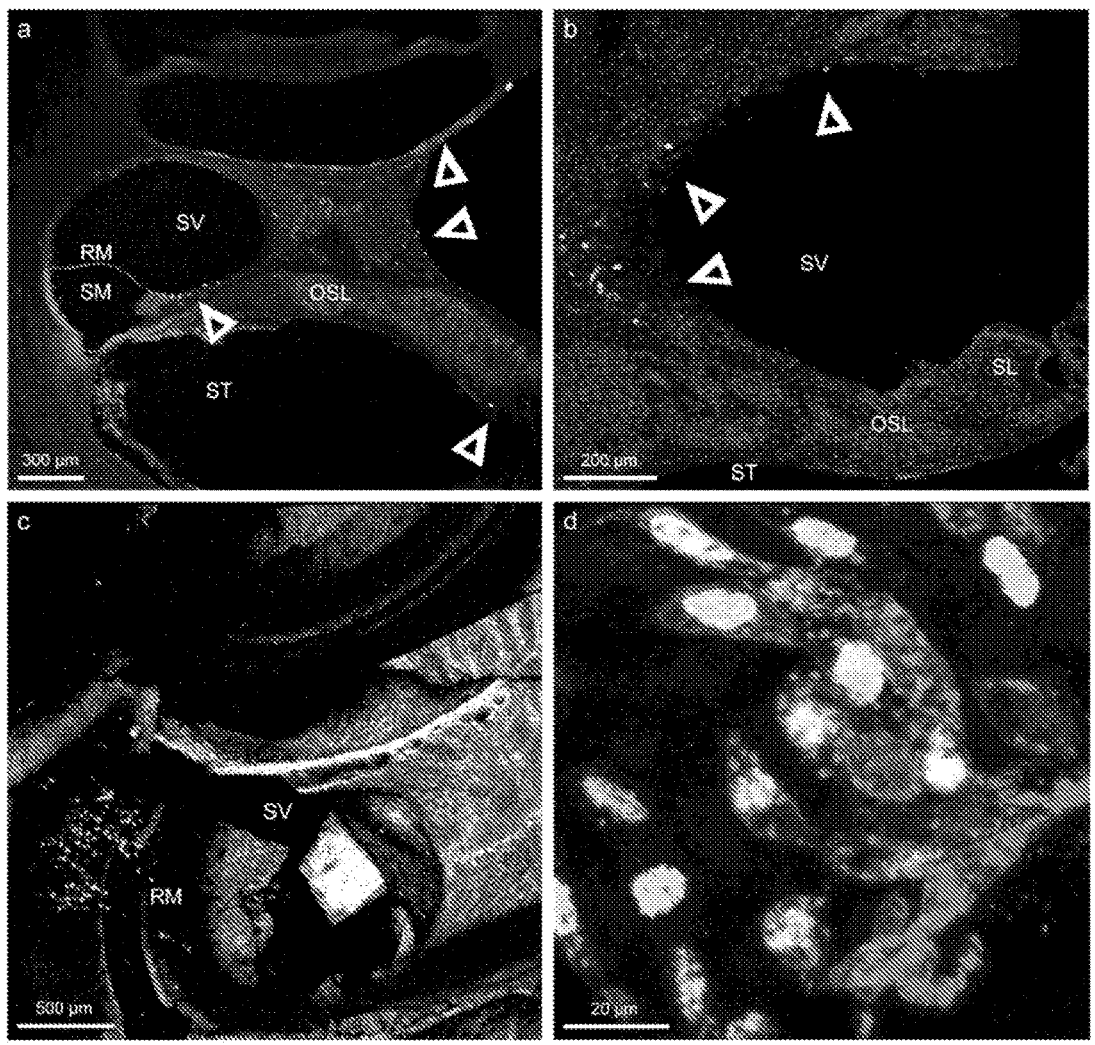
Figure 9 c d e

Figure 17 (cont'd)
d
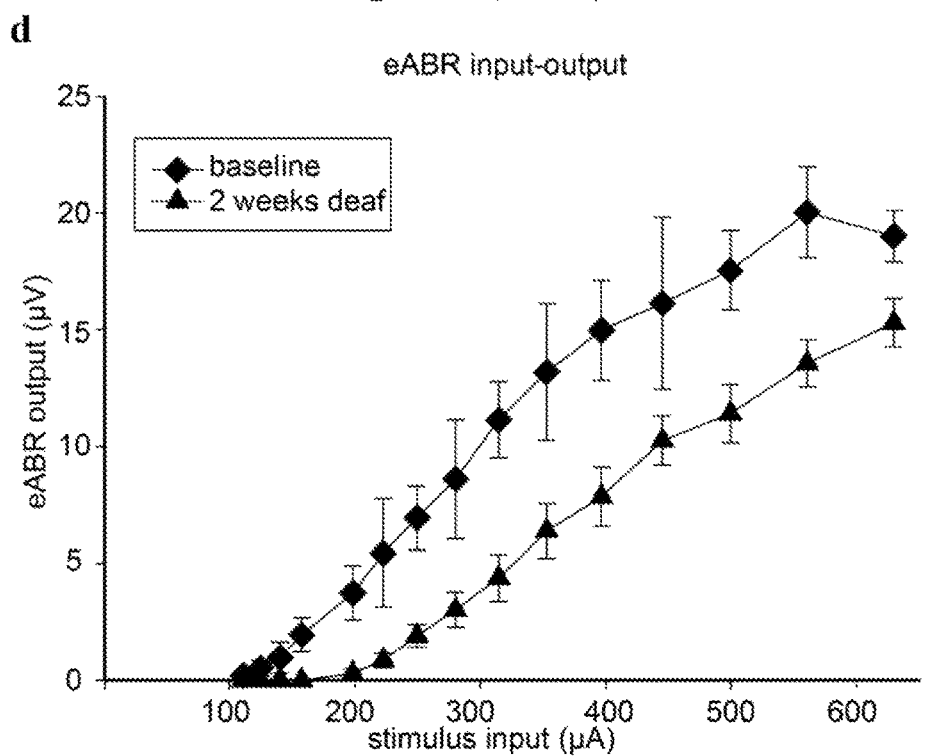
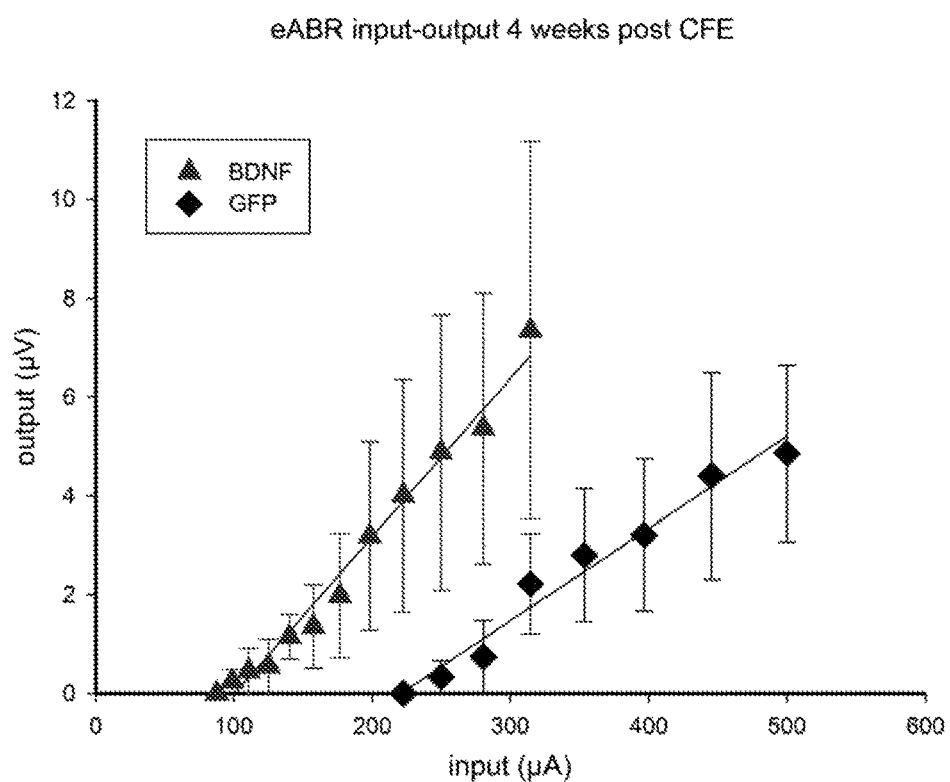
Figure 18

Figure 23
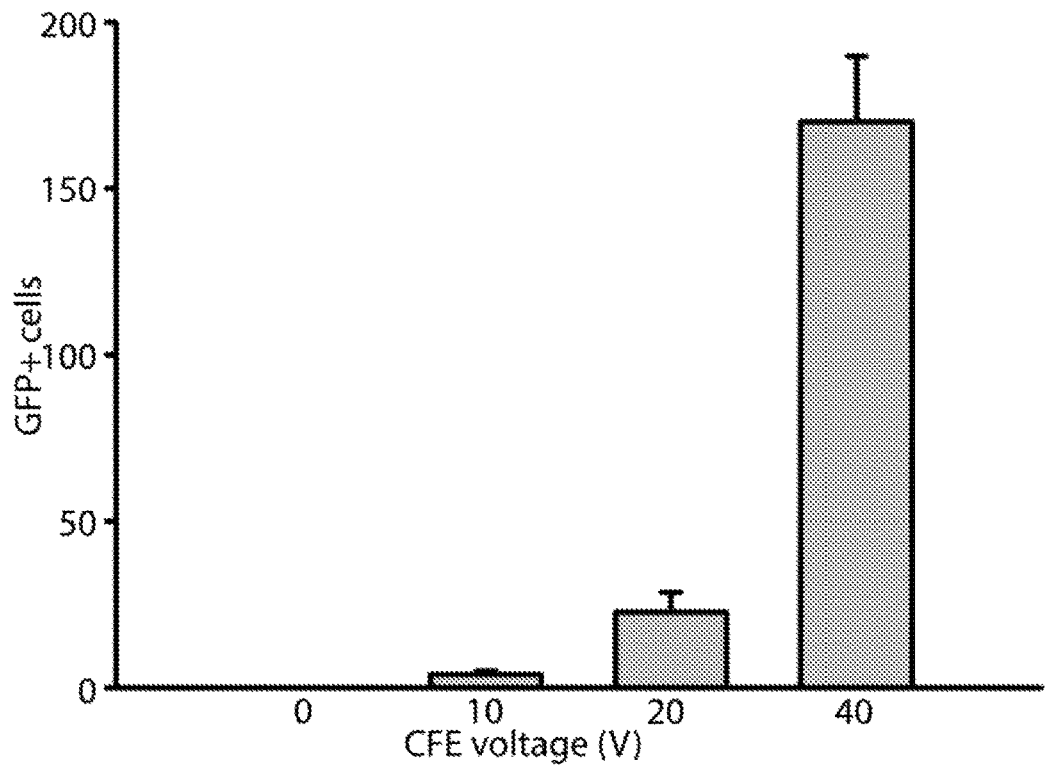
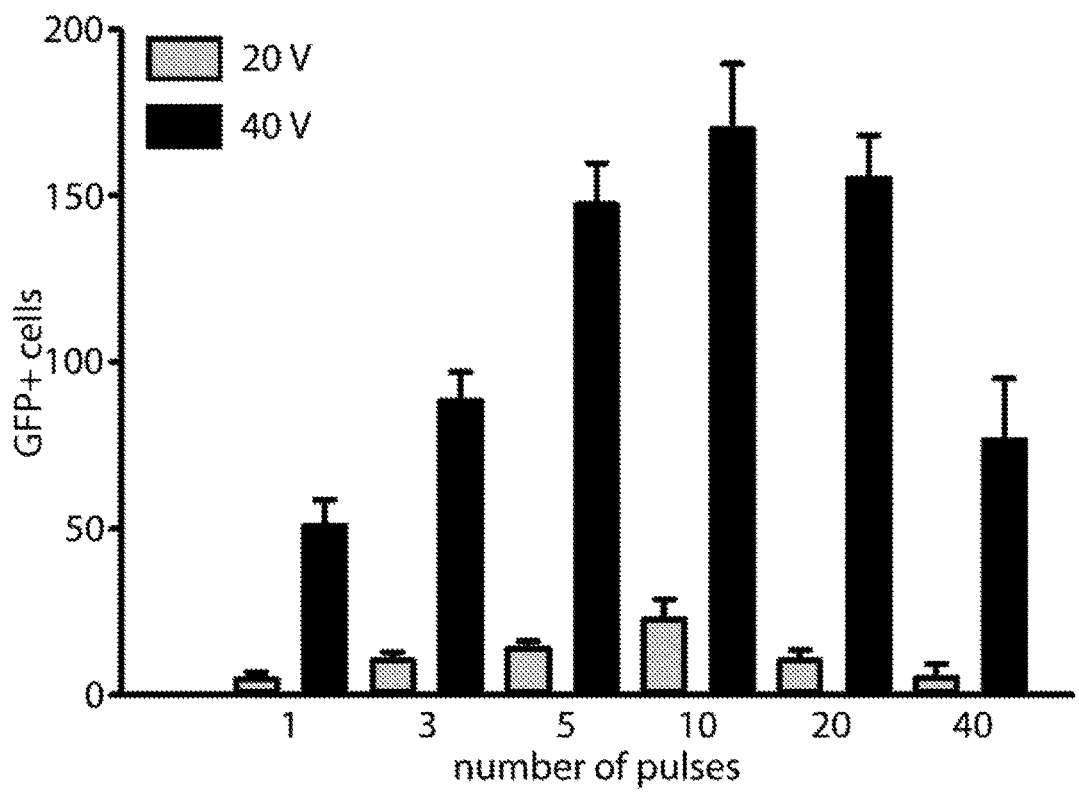
Figure 24

METHOD AND APPARATUS FOR CLOSE-FIELD ELECTROPORATION

TECHNICAL FIELD

The present invention relates to a method of providing an agent to cells within a target region in a subject. The method has particular application in providing enhanced transfection of one or more cells within a limited target region within a subject, such as a limited target region within a cochlea.

BACKGROUND ART

Electroporation is a well-established methodology for delivery of a variety of molecules into cells, including drugs, proteins and nucleic acids. The latter is highlighted by the electroporation-based delivery of DNA into cells to drive recombinant gene expression. The underlying principle is that an electric field generated by a high voltage pulse between two electrodes causes a transient dielectric breakdown of the plasma membrane of cells within the high intensity electric field, enabling the negatively-charged DNA to enter the cells. However, the process by which the DNA/cell membrane interface responds to the electric field to enable the DNA to enter the cell is not well understood.

The most common use for electroporation-based gene delivery is for molecular biology research, where simple plate electrodes within cuvettes enable routine transformation of competent cells on the bench. Electroporation-based gene delivery has subsequently been extended to in situ, ex vivo, and in vivo applications with development of specialised electroporation systems. These electroporation systems include a variety of electrode designs and voltage pulse shaping as part of optimised electroporation parameters, along with custom electroporation solutions and electrodes, with pulse intensity, pulse duration and repetition frequency being key parameters. These systems have proved effective in facilitating research in a range of tissues, including developmental neurobiology applications.

However, electroporation is still considered problematic for therapeutic gene delivery due to low transformation efficiency, difficulty in placement of electrodes into tissues and the typically high voltages that need to be applied to destabilise the cell membrane. This can detrimentally affect the target organs and tissues, and may also impact on DNA stability.

Despite the breadth of uptake of electroporation both in vitro and in vivo, current technology has been limited to the application of electric fields utilising conventional electrode configurations (typically plates and needles separated by tissue).

To date, no reports exist of electroporation-based gene delivery into the mature bony cochlea, where paddle electrodes or penetrating needle electrodes are untenable. WO 2011/006204 reports use of a single electrode inserted into the base of the cochlea to deliver an electric field and an external current return electrode, with applications of up to 100 V and up to 20×50 ms pulses immediately after injecting plasmid DNA into the cochlea fluid compartments. This achieved a number of transfected cells expressing a fluorescence reporter protein, but transformation efficiency was limited, as was specificity for the region targeted for transformation.

There is therefore a need for improved techniques which allow for more efficient and/or more targeted transfection of cells in vivo.

SUMMARY

The present studies have surprisingly found that generation of high field strengths within millimetre to sub-millimetre dimensional space (close-field) allows for highly efficient and targeted transformation of mammalian cells. The efficacy of this new mode of electroporation was greater than that of conventional 'open-field' electroporation—where electrodes are separated by tissue, with lower required voltages for transfection of the cells, and is hereinafter termed Close-Field Electroporation ('CFE').

Thus, according to a first embodiment of the invention, there is provided a method of transfecting one or more cells within a target region with an agent by electroporation, said method comprising exposing said one or more cells to said agent and to a close electric field created between an anode or anode array and a cathode or cathode array, in said target region for sufficient time to allow at least some of said agent to enter said one or more cells. The electrodes may be contiguous to an array structure of at least 2 electrode elements, but electrode or electrode elements may be separated by a distance of less than 5 mm. According to an embodiment subjects that may be treated by methods according to the present invention comprise human and non-human animals. The close electric field may be generated by the anode or anode array and the cathode or cathode array being separated by between about 10 μm and about 5 mm, more typically between about 50 μm and about 1 mm, and more typically between about 50 μm and about 0.5 mm.

The methods of the present invention allow for use of significantly lower voltages while maintaining highly efficient transformation of cells. According to an embodiment, the voltage applied between the anode or anode array and the cathode or cathode array is about 1V to about 40V, more typically from about 1V to about 30V, and even more typically from about 4V to about 20V.

The methods of the present invention also allow for significantly lower total charge delivery while maintaining highly efficient transformation of cells, significantly reducing the risk of collateral damage to cells in the region of cells being treated. According to an embodiment the total electric charge delivered during said electroporation is less than 4 Coulombs, more typically less than 0.4 Coulombs, more typically less than 0.1 Coulombs, and more typically less than 0.01 Coulombs. Ignoring the roughness factor (the fine 3-dimensional structure of platinum electrodes), the effective charge density on platinum electrodes may be between about 1 mC/cm$^2$ and about 1 C/cm$^2$, such as between about 25 mC/cm$^2$ and about 250 mC/cm$^2$.

Methods according to the present invention may be carried out using any suitable arrangement of anode(s) and cathode(s) provided they provide a close electric field, thus providing a focussed high electric field in the region of the target cells. Such arrangements may comprise separately inserted or applied electrodes, or anodes and cathodes provided on the same probe. According to an embodiment, the anode or anode array and the cathode or cathode array are provided on a single probe to be introduced into said region. An example of an electrode configuration contemplated by the present invention is embodied by a cochlear implant electrode array. Electrodes of a cochlear implant electrode array may be in a linear configuration and configured to have distal electrode(s) as an anode or cathode array and proximal electrode(s) as an array of the opposite polarity (viz. cathode or anode array). Alternatively, the electrodes may be in a planar configuration, with anode(s) and cathode(s) interspersed or configured substantially or completely on opposite sides of the plane. An anode or cathode array may each, independently, comprise any number of electrodes. According to an embodiment, an anode or cathode array may each, independently, comprise from 2 to 8 electrodes and, more typically, each of the arrays comprises 4 electrodes.

Methods according to the present invention may be used to transfect cells within a target region with any desirable agent amenable to electrophoretic transfer into cells. Such agents may include, for example, nucleic acids and analogues thereof, peptides and proteins and analogues thereof as well as other small or large molecules. According to an embodiment, the agent is a nucleic acid. In another embodiment, the agent may comprise or be a fluorescent or other labelling moiety or may comprise or be a photoactivatable moiety, such as may be employed in cancer treatment.

Methods according to the present invention may be for producing, enhancing or suppressing an activity within said region and may be, for example, for at least partially restoring physiological function within said target region, one or more regions proximal to said target region, or both within said target region and one or more regions proximal to said target region. In another embodiment, methods according to the present invention may be for regulation of cell function or for localized cancer treatment.

According to specific embodiments, methods according to the present invention may be for transfecting cells within a targeted region of the cochlea of a subject. In such embodiments, the agent may comprise or consist of a nucleic acid molecule. In such embodiments, the close electric field may be provided by a cochlear implant electrode array and, in a particular embodiment, a distal half of the operational electrodes may be configured as an anode array or cathode array and a proximal half of the operational electrodes may be configured as an opposite electrode array (i.e. cathode or anode). In another embodiment the electrodes within a cochlear implant array may be divided into blocks of anode or cathodes, or combinations thereof. The nucleic acid molecule may encode a neurotrophic factor for peripheral sensory neurons, and in particular embodiments the nucleic acid molecule encodes a neurotrophic factor for spiral ganglion cells. In particular embodiments the nucleic acid molecule encodes a transcription factor which promotes the expression of a neurotrophic factor. In particular embodiments the nucleic acid molecule encodes one or more therapeutic molecules for spiral ganglion cells.

In particular embodiments the cells in the target region in the subject are cells of the scala tympani or scala vestibuli, such as mesenchymal cells.

According to another embodiment of the invention, there is provided an electroporation electrode assembly comprising an anode or anode array and a cathode or cathode array for creating a close electric field in a target region, for transfecting one or more cells in a target region by a method of the invention as described above.

BRIEF DESCRIPTION OF THE DRAWINGS

Certain embodiments of the present invention will now be described, by way of example only, with reference to the accompanying drawings.

FIG. 1 shows an exemplary gene therapy construct for use in methods according to the present invention, and "alternating" and "tandem" electrode configuration in a cochlear implant 8-electrode microarray. a) BDNF-GFP plasmid: cytomegalovirus promoter (CMVp) upstream of the FLAG-tagged brain-derived neurotrophic factor (BDNF) gene cDNA. The BDNF and green fluorescent protein fused to a nuclear localization site (GFPnls) coding region are transcribed simultaneously, but translated as separate proteins via an internal ribosome entry site (IRES). pA, SV40n polyadenylation site; OriR, origin of replication; aph, kanamycin selection. b) Alternating and tandem electrode close-field electroporation microarray configurations. c) Exposed cochlea with the eight electrode cochlear implant microarray overlaid. d) Cochlear implant inserted into scala tympani via the round window.

FIG. 2 shows electrical modelling of the electrical field in close-field electroporation ("CFE"). A. shows a model of a linear microarray with 8 flat electrodes with a surface area of 60 $\mu m^2$ each in either the 'tandem', or 'alternating' electrode configuration, overall length 1 mm. The model predicts an even, high field strength at the anodes, while in the 'alternating' electrode layout, there is a bias in field strength to the distal end. This maps well to pilot data from transfections of HEK293 cell sheets (see FIG. 6) utilising a cochlear implant microarray. B. A model of electric fields arising from CFE utilizing central electrodes in a hexagonal array (770 $\mu m$ electrode pitch), with a single return electrode; insert shows fabrication layout of a planar microarray.

FIG. 3 shows a number of possible cochlear implant microarray configurations for use in methods according to the present invention.

FIG. 4 provides a bar chart for numbers of close field electroporation transfected cells for treatment of confluent HEK293 cells on Poly-D-lysine coated coverslips by methods according to the present invention using a range of electrode configurations and electrostimulation protocols.

y=a+b*x, where a=6.2, b=0.79, $R^2$=0.71; mean±s.e.m.; multiple data points at each voltage level reflect variation in number of pulses (see Table 1). ** P=0.005; ANOVA, Holm-sidak pairwise comparison. f) Effect of charge on mesenchymal cell transformation. Tandem configuration:

$$y=a/x \exp[-0.5(\ln(x/x_0)/b)^2], \text{ where } a=3.012,$$
$$b=1.354, x_0=0.072, R^2=0.787$$

demonstrating a distinct optimum corresponding to 20 V 5-10 pulses. Alternating configuration: y=a+b*x, where a=9.1, b=174.4, $R^2$=0.948. * P=0.039; Mann-Whitney Rank Sum test.

FIG. 8 illustrates results for ex vivo CFE of a BDNF-GFP expression cassette using a) tandem and b) alternating microarray configurations. Nuclear GFP fluorescence is evident in mesenchymal cells lining the perilymphatic compartment in the basal turn region of the guinea pig cochlea—SV, scala vestibuli; ST, scala tympani; SL, spiral limbus. Confocal 3D reconstructions.

FIG. 9 illustrates localisation of CFE BDNF-GFP transformants in the guinea pig cochlea ex vivo and in vivo. a) Cryosection (50 μm) identifying the transformed cells (GFP+ve; white dots) as mesencyhymal cells lining the perilymphatic compartments (arrowheads). ST, scala tympani; SV, scala vestibuli; SM, scala media; RM, Reissner's membrane. CFE: tandem configuration 20V—5 pulses; hi vivo at day 4. b) Fluorescence imaging of transformed mesenchymal cells in scala vestibuli (SV)—GFP nuclear labelling (white). CFE: alternating configuration 40V—20 pulses; ex vivo, 3 days organotypic culture. OSL, osseous spiral lamina; SL, spiral limbus. c) Low power image of GFP fluorescence (white dots) in mesenchymal cells on Reissner's membrane. Alternating configuration CFE 40V—20 pulses; 3 days organotypic culture. Background structure provided by autofluorescence acquired on a separate channel. d) Detail of cells shown in c), with double fluorescence of GFP reporter and BDNF synthesis).

Figure 10:

FIG. 10 shows microCT of the guinea pig skull showing the 8 electrode cochlear implant microarray in situ within the lower turn of the cochlea. a) top down view; implanted (left) and control cochleae are indicated by arrowheads. b) detail of microarray within the basal turn of the left cochlea showing the 8 platinum ring electrodes. c) Tilted right-side view of skull showing the right (upper) and left (implanted) cochleae.

Figure 11:
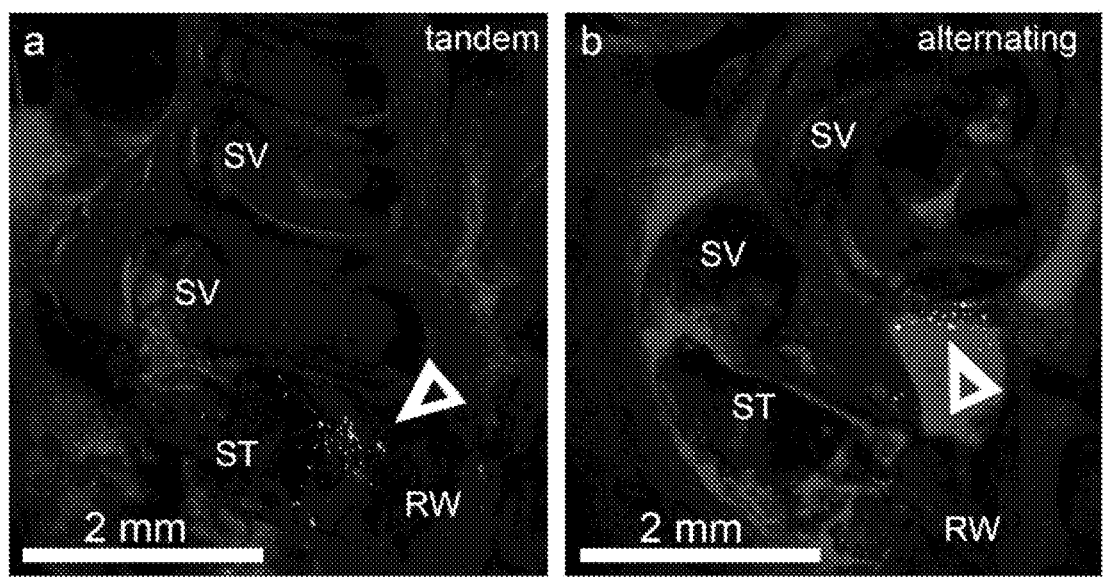
Figure 11:
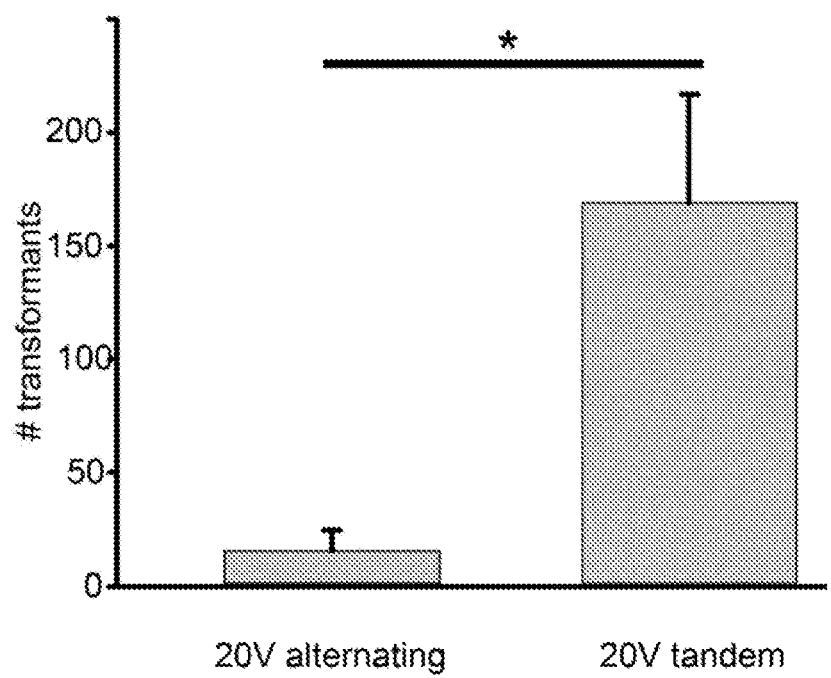

FIG. 11 shows results for in vivo CFE of guinea pig cochleae using cochlear implant electrode microarrays in alternating or tandem electrode configurations: a) Transduced mesenchymal cells (GFP+) in the perilymphatic compartments (scala tympani (ST) and scala vestibuli (SV)) 4 days post tandem configuration CFE—white arrowhead. RW—round window. 20 V—5 pulses. b) Alternating configuration CFE: 20 V—5 pulses. c) Tandem configuration CFE provided ~8 times greater transformation efficiency than alternating array CFE (n=7 tandem, n=4 alternating). * P=0.043 (t-test).

Figure 12:
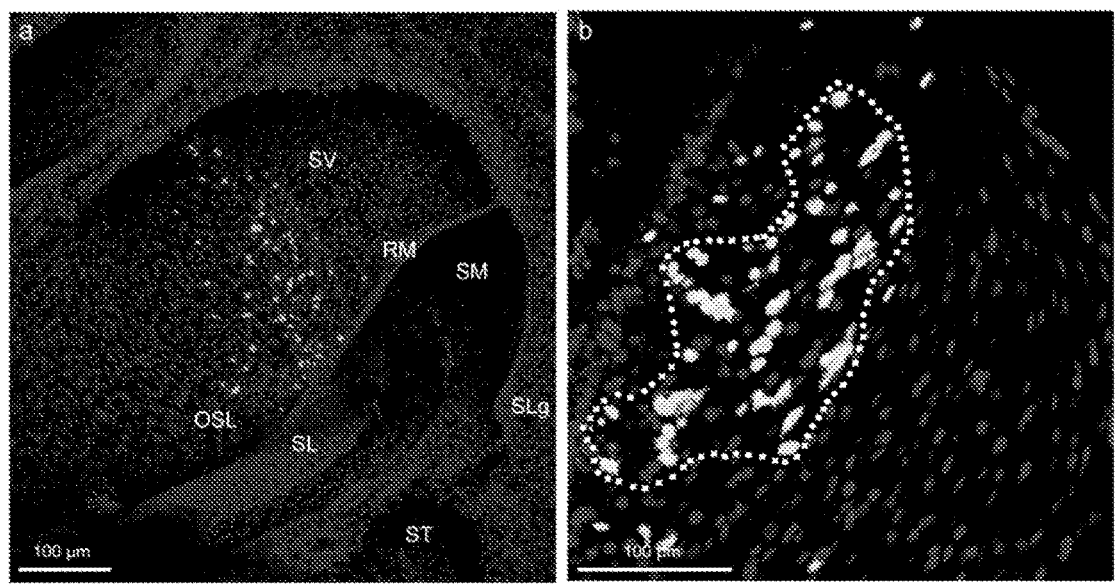

FIG. 12 shows results for in vivo tandem configuration CFE of the BDNF-GFP gene construct. a) Fluorescence imaging of transformed mesenchymal cells lining the perilymphatic compartment of the cochlea (nuclear localization of GFP, white dots), with overall cell density determined by DAPI nuclear labelling (grey—via multi-photon excitation). b) The maximum transformation efficiency was determined by calculating the number of GFP+ cells/total cell number within a region of interest containing >100 cells as outlined. CFE: 20V—5 pulses; imaged 4 days post-treatment.

Figure 13:
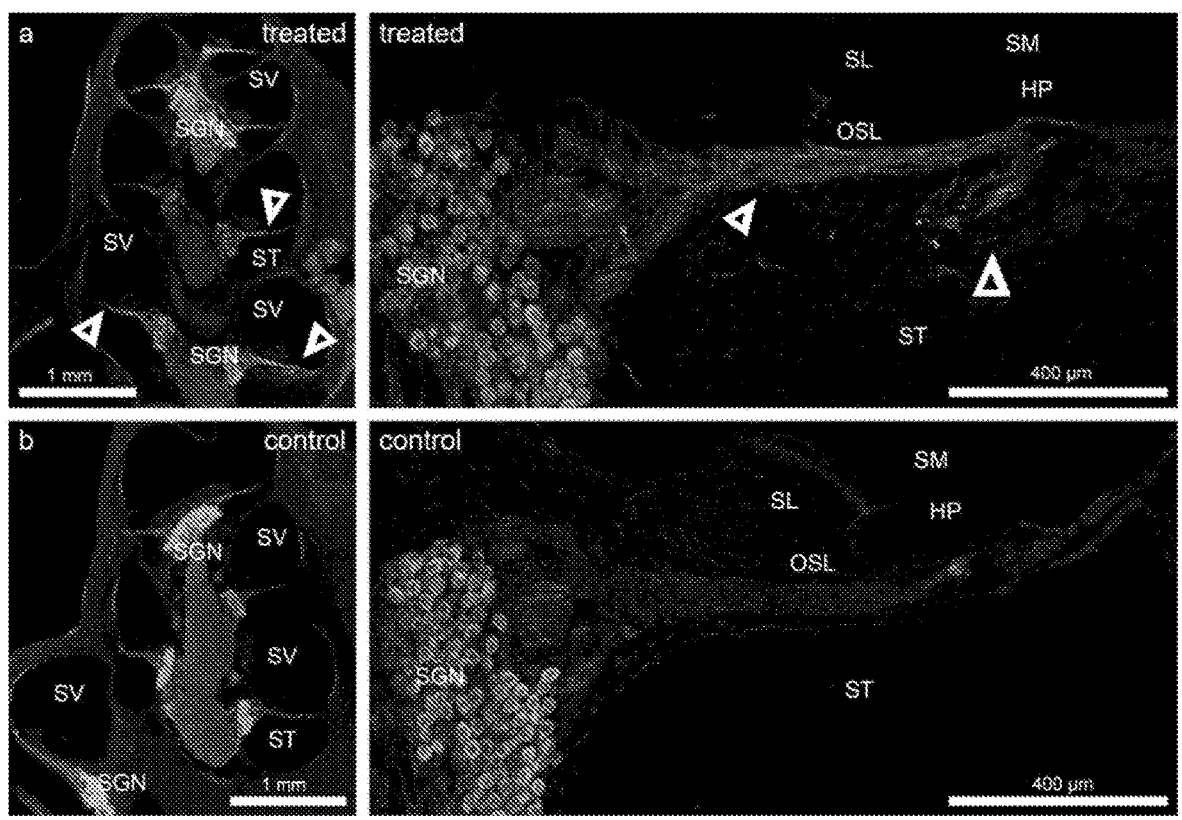
Figure 13:
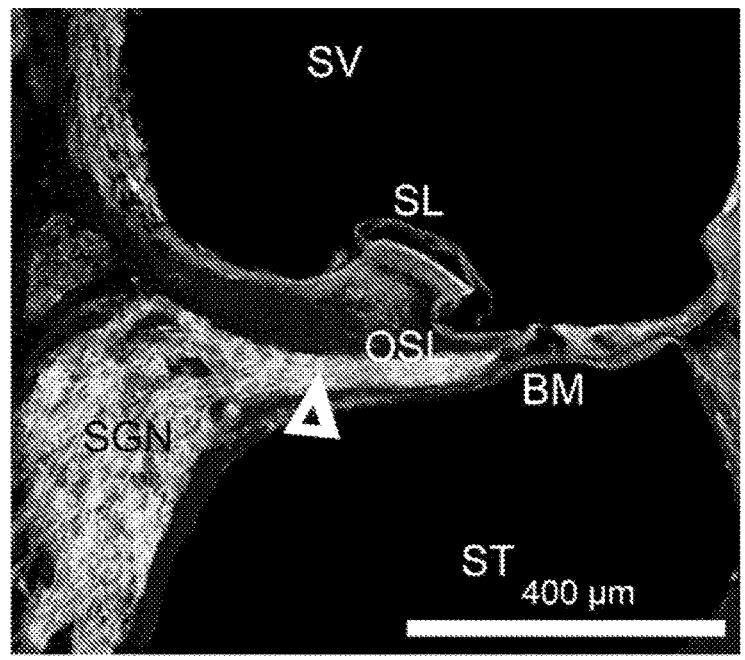
Figure 13:
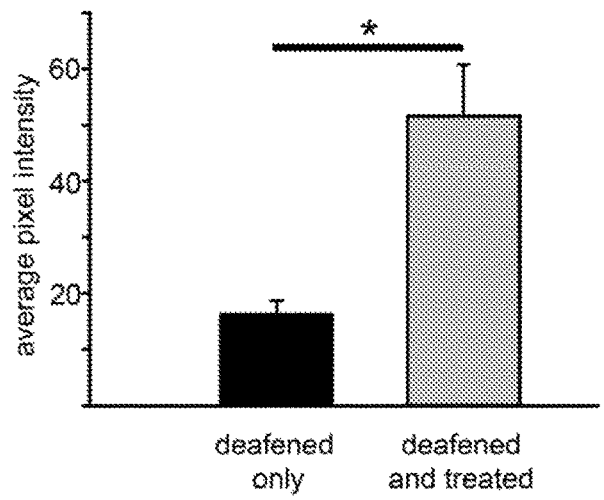
Figure 13:
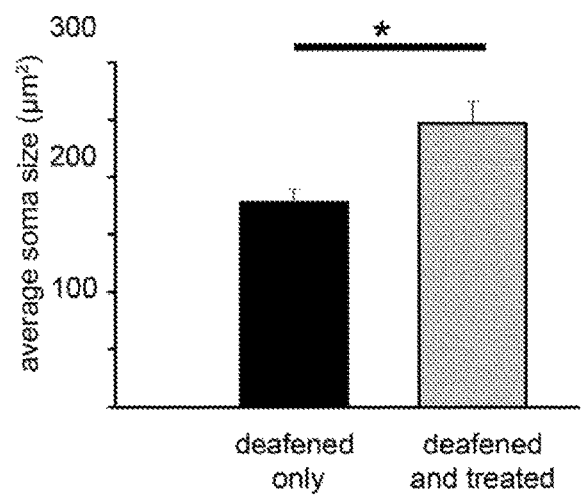

FIG. 13 shows results for BDNF gene therapy in a deafened cochlea. a) Regeneration of spiral ganglion neuron (SGN) two weeks post CFE (alternating; 40V—20 pulses). Type III β-tubulin immunofluorescence of SGN, highlights restored neurites in the osseous spiral lamina (OSL), which extend beyond the habenula perforata (HP) and branch into scala tympani (ST)—arrowheads. SL—spiral limbus; SM—scala media (endolymph); SV—scala vestibuli. b) Control (right) cochlea from the same guinea-pig; contrasting the loss of peripheral neurites in the OSL and atrophy of the SGN somata. Right-side images provide detail of the basal region. Grey in (a) (left-hand side), and (b) (left-hand side) is autofluorescence, used to provide cochlear structure: grey in (a) (right-hand side) and (b) (right-hand side) shows fluorescence from DAPI nuclear staining. c) Aspartoacylase (ASPA) immunofluorescence (white) showing satellite cell myelination of the regenerated neurites in a BDNF treated cochlea. d) Neurite regeneration with gene therapy. Data are mean (±s.e.m.); β-tubulin immunofluorescence pixel intensity (average sum of pixel intensity $\mu m^{-2}$) within the OSL; * P=0.017, paired t-test. (n=4). e) Increase in soma size of BDNF-treated SGN; comparing cross-sectional areas of neuron somata (n=4) (* P=0.012, paired t-test). 50 μm cochlear cryosections.

Figure 14:
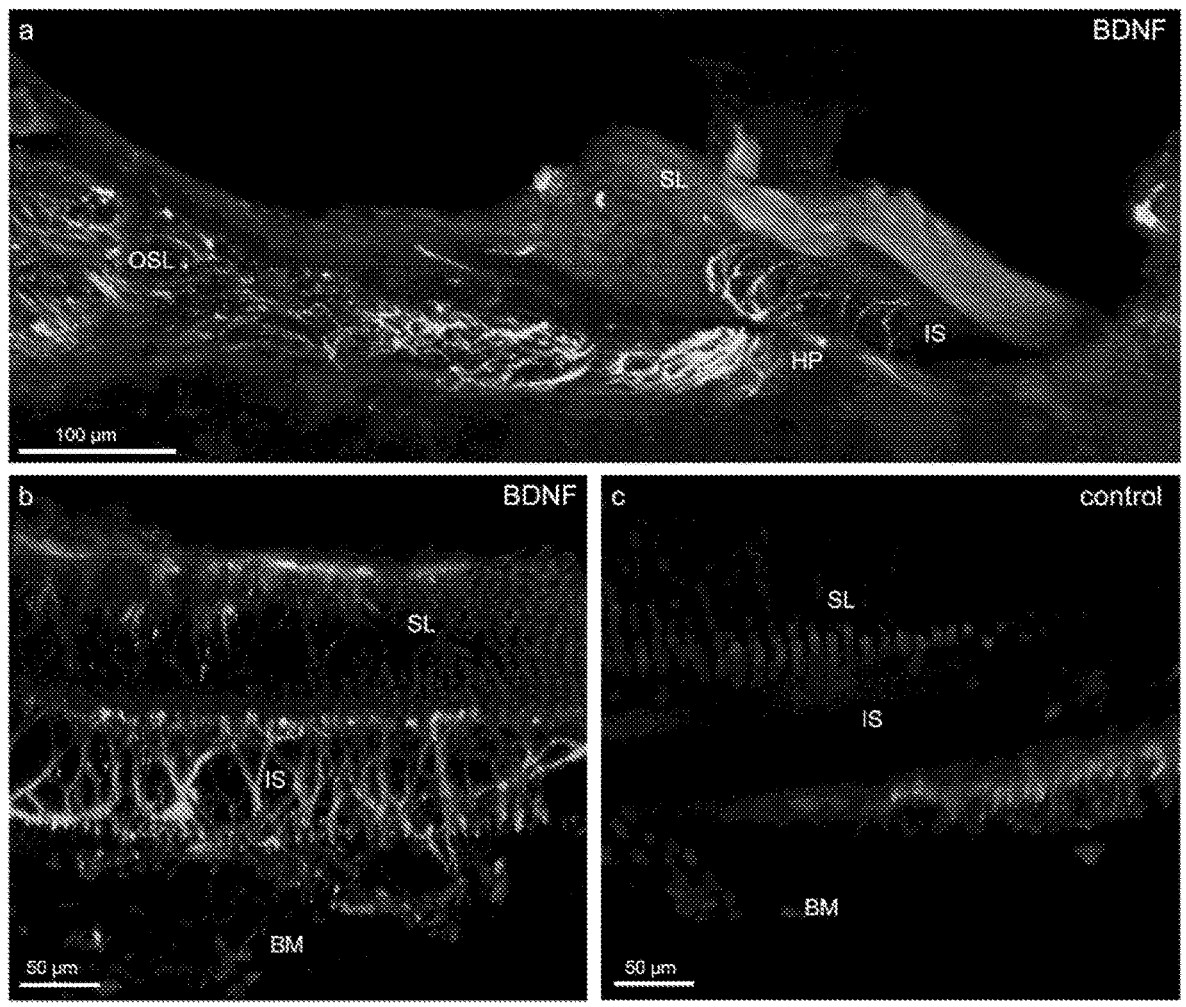

FIG. 14 shows results for BDNF gene therapy using tandem configuration CFE. a) Type III ß-tubulin immunofluorescence of the hemi-sectioned cochlea two weeks after electroporation (20V—5 pulses) (4 weeks post-deafening). Confocal 3D reconstruction shows the spiral ganglion neurite regeneration back along the osseous spiral lamina (OSL), through the habenula perforata (HP) and extending to the inner sulcus (IS) region, under the lateral prominence of the spiral limbus (SL). Cochlear structure shown by autofluorescence. b) Detail of the same preparation showing the ectopic branching of the regenerated neurites. Nuclear labelling (DAPI)—grey signal. c) Control (deafened, no gene therapy) right cochlea from the same guinea pig.

Figure 15:
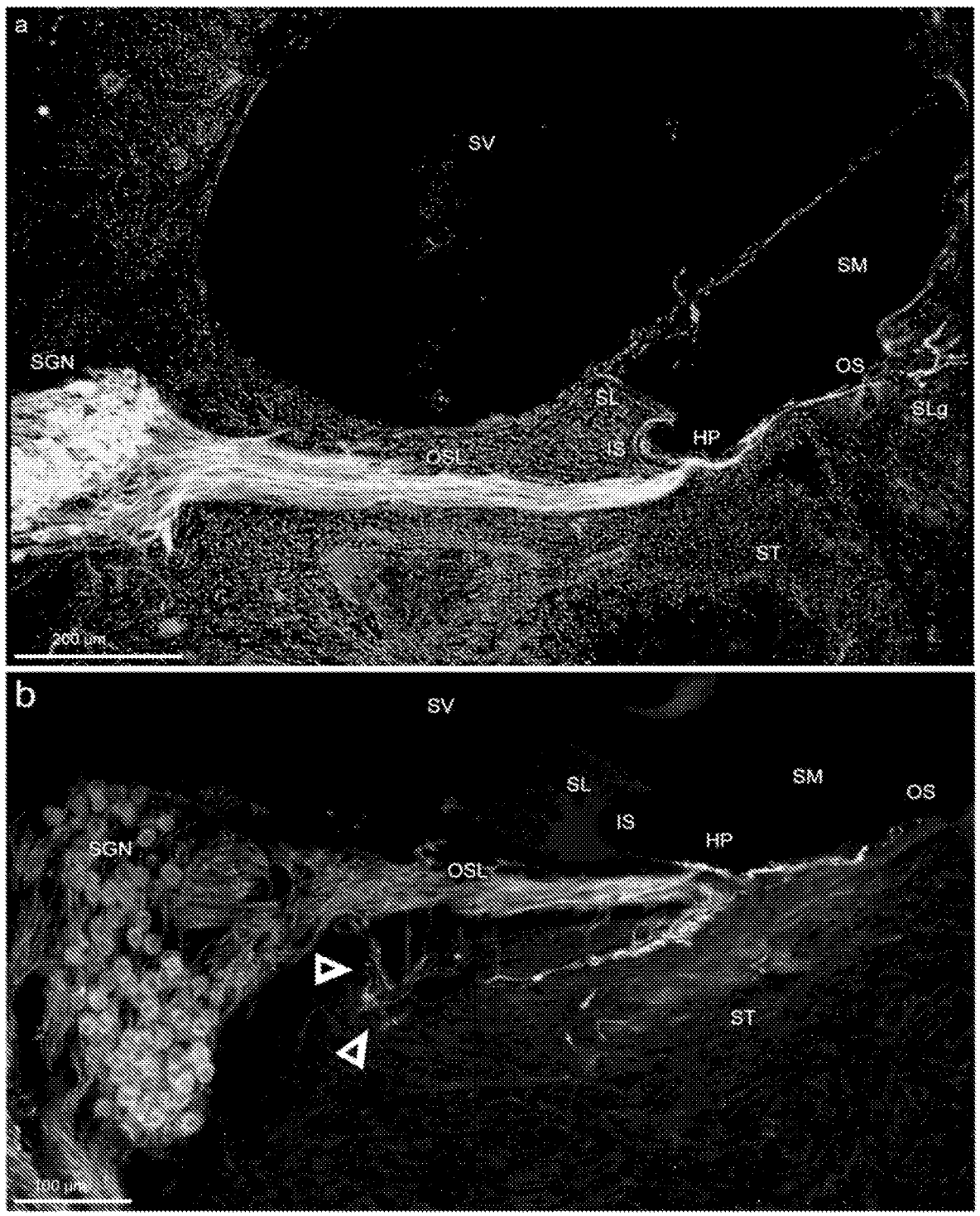

FIG. 15 illustrates examples of regeneration of the spiral ganglion peripheral neurites in vivo following CFE-mediated BDNF gene therapy in deafened guinea pigs. a) Image from a cryosection (50 μm) showing peripheral spiral ganglion neurites, extending back through the osseous spiral lamina (OSL) to the former site of the hair cells, now a flattened basilar membrane lacking hair cells and supporting cells immediately to the right of the habenula perforata (HP). (3 weeks post ototoxic treatment). The neurites are shown branching at the HP, to project medially to the inner sulcus region (TS) and laterally to the outer sulcus (OS) and spiral ligament (SLg). Endolymphatic compartment (scala media, SM). Fibres also project into scala tympani (ST). SGN, spiral ganglion neurons; SV, scala vestibuli. Alternating configuration CFE: 40V—20 pulses, 7 days post-treatment. DAPI nuclear fluorescence evident in background. b) Detail of outgrowth of fibres in the OSL, with ectopic branching of fibres into ST, both at the HP, and directly from the OSL (arrowheads). Cryosection (50 μm). CFE: alternating configuration 40 V—20 p; 11 days post-treatment (25 days post ototoxic treatment).

Figure 16:
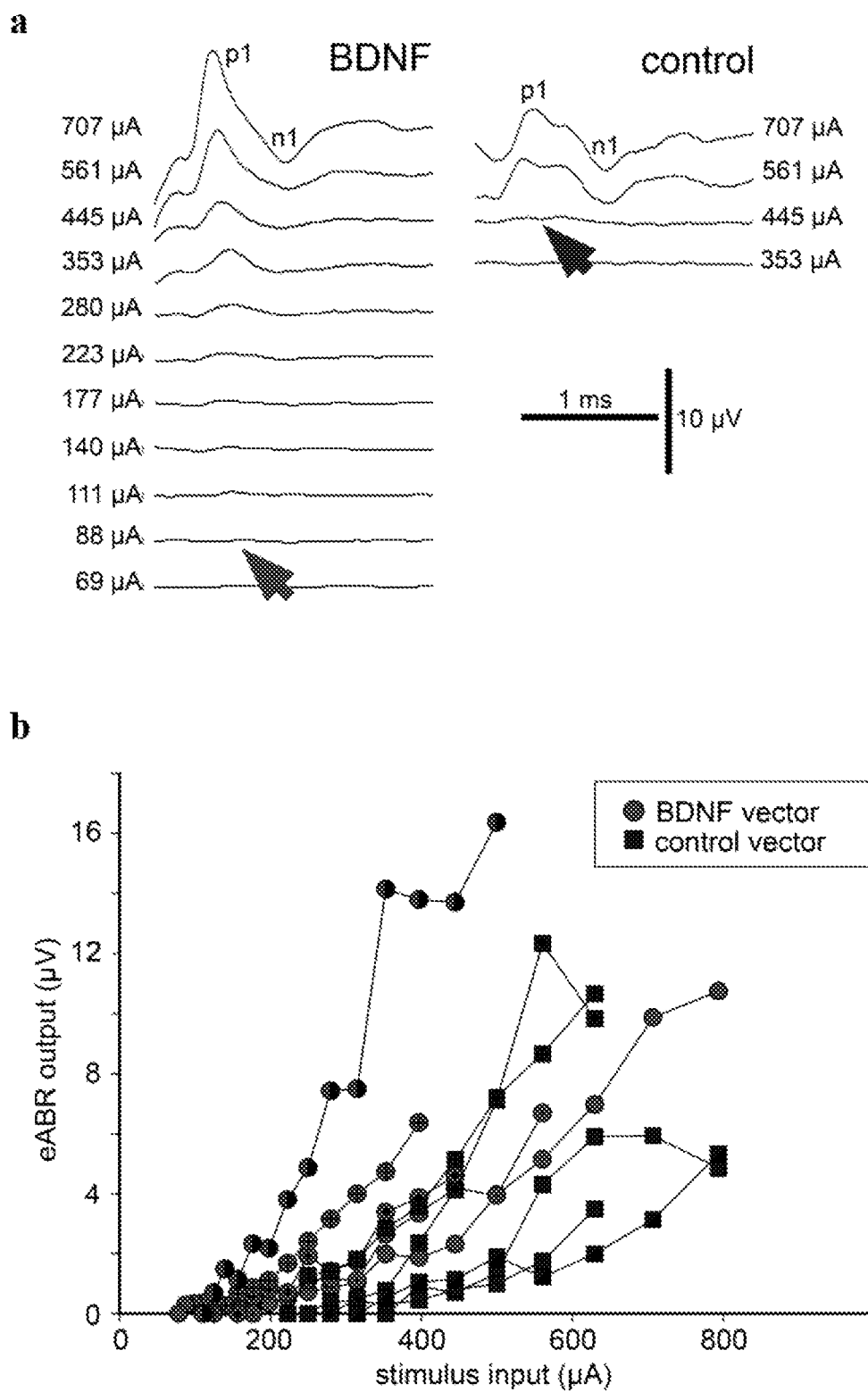
Figure 16:
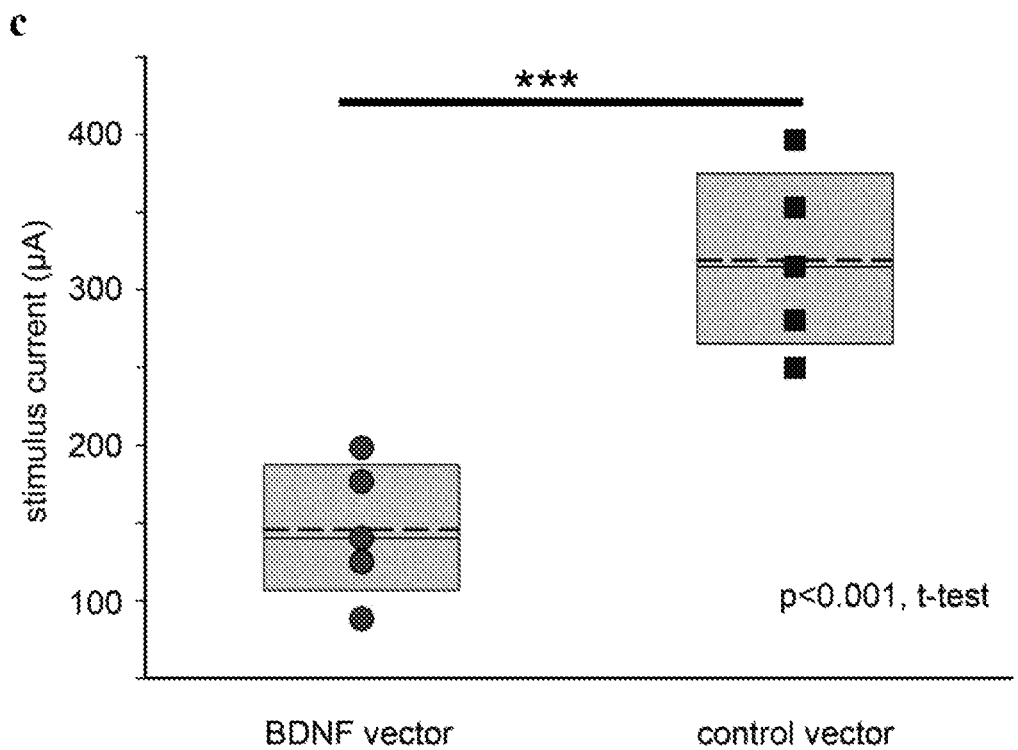
Figure 16:
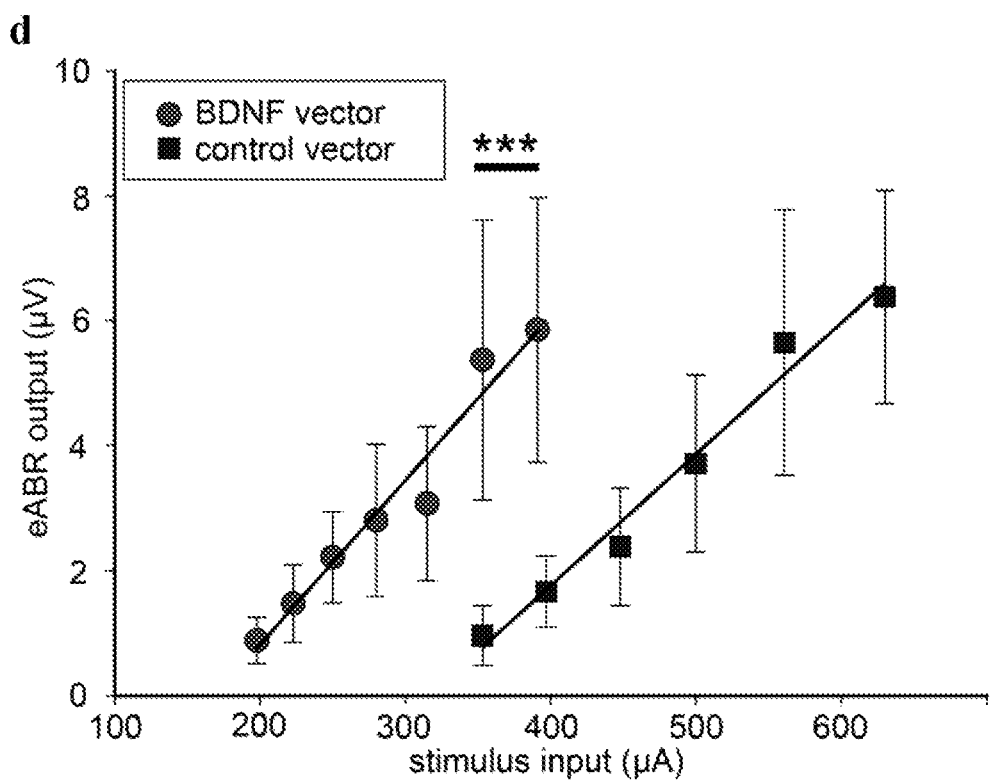

FIG. 16 shows functional validation of enhanced cochlear implant performance following BDNF gene therapy via tandem configuration CFE (20V—5 pulses; deafened guinea pig model). a) eABR traces after BDNF gene therapy; note the lower current stimulus needed to elicit a threshold response (88 μA—left arrowhead) compared to the threshold level of a control (CFE with a GFP-only vector) animal (445 μA—right arrowhead); two weeks post CFE gene delivery; four weeks post deafening. b) Individual eABR input-output functions (p1–n1 amplitude=output) for BDNF-treated versus control (n=5 for each). Note the lower thresholds and broader dynamic range of the eABRs with BDNF gene therapy. c) eABR thresholds. The mean threshold (dashed line) of the BDNF treatment group was less than half that of the control group. * P<0.001, t-test. d) Average eABR input-output growth functions. Linear regression best-fits: BDNF group: y=a+bx, where a=−4.45, b=0.026, $R^2$=0.957; Control group: y=a+bx, where a=−6.64, b=0.021, $R^2$=0.979. * P<0.001, ranked two way ANOVA.

Figure 17:
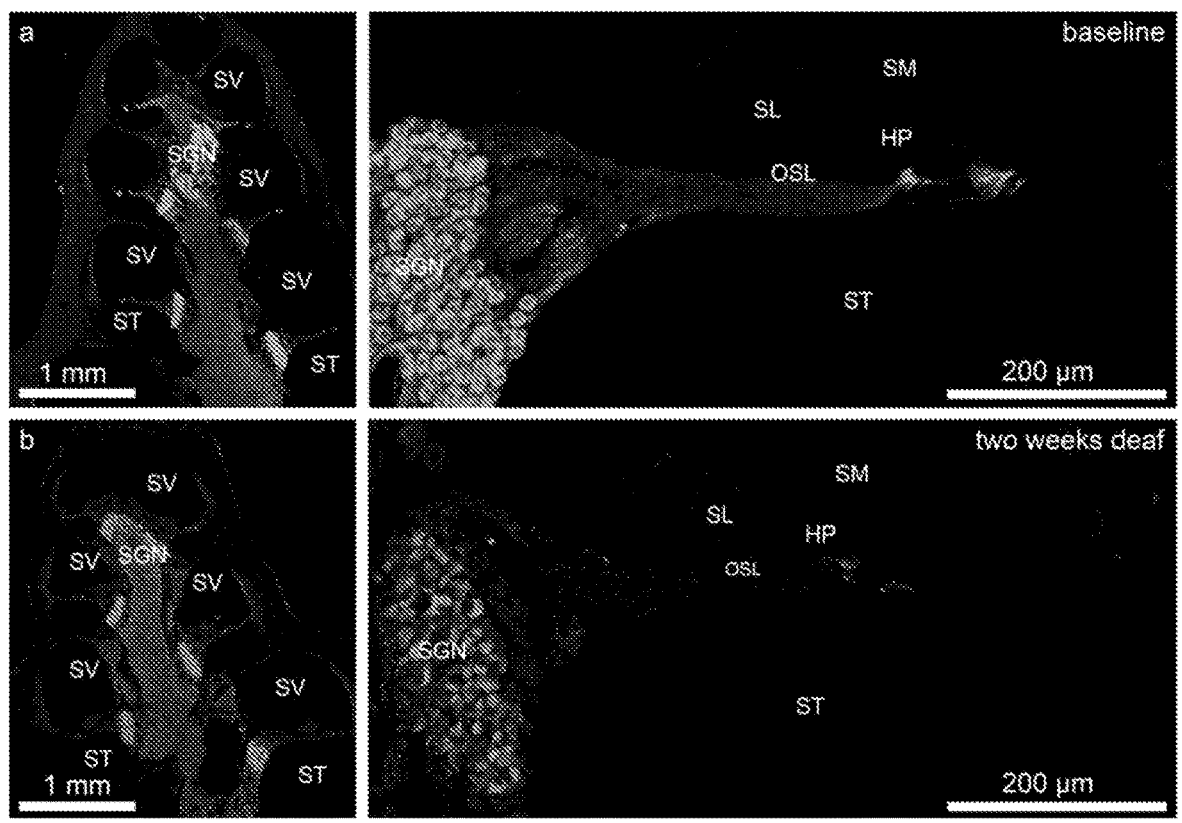
Figure 17:
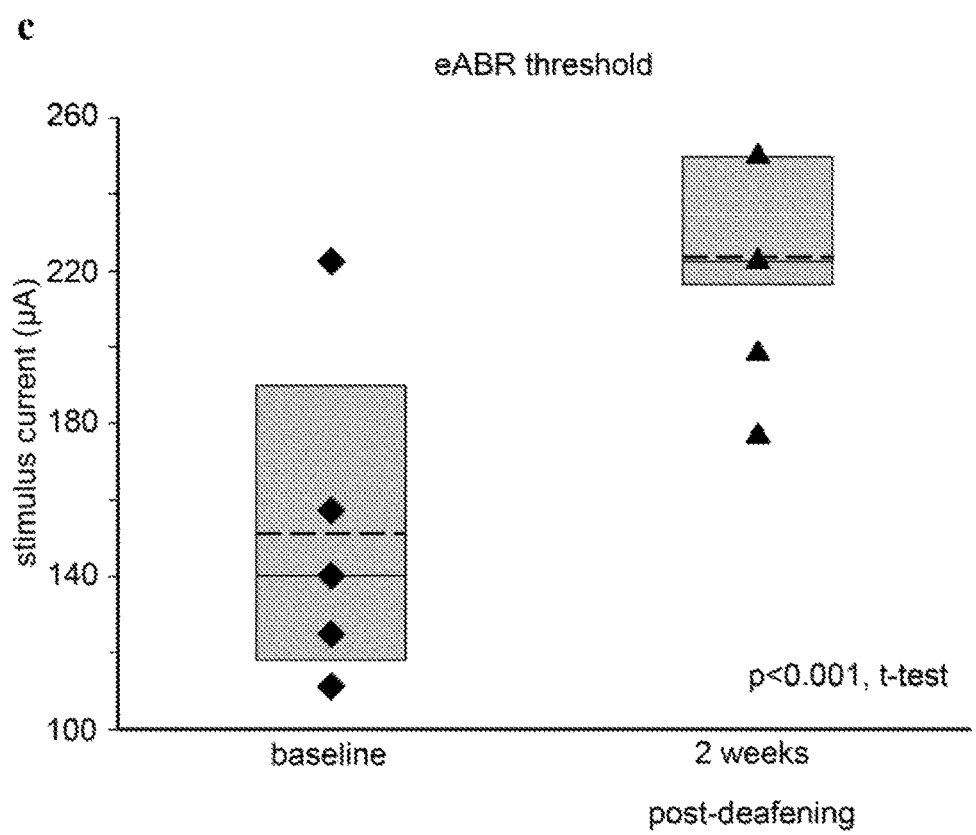

FIG. 17 shows control histology and eABR data. a) Immunofluorescence (anti-β-tubulin) of a cryosection from an untreated guinea pig cochlea. SGN—spiral ganglion neurons; OSL—osseous spiral lamina; HP—habenula perforata; SM—scala media; ST—scala tympani; SV—scala vestibuli; SL—spiral limbus. Left-hand side—autofluorescence channel for structural detail; Right-hand side—DAPI nuclear labelling in background. b) β-tubulin immunofluorescence from a cochlear cryosection 2 weeks post-ototoxic deafening. This is the point where CFE gene therapy was performed. c) Box plots with overlaid data showing eABR thresholds for acute cochlear implants, and implants inserted 2 weeks post deafening (n=5 acute; n=10 deafened). Dashed lines are the means. d) Average eABR input-output functions for baseline and deafened states.

FIG. 18: Follow-up eABR data on CFE-mediated BDNF gene therapy at 4 weeks post implant (6 weeks post-deafening). Note that the stimulus thresholds and growth functions of the BDNF-treated animals approach the baseline data (see FIG. 18). Linear regressions: BDNF treatment: y=−3.227+0.032*x, $R^2$=0.981; GFP control: y=−4.121+0.0186*x, $R^2$=0.971. (n=2 BDNF treated, n=4 control).

Figure 19:
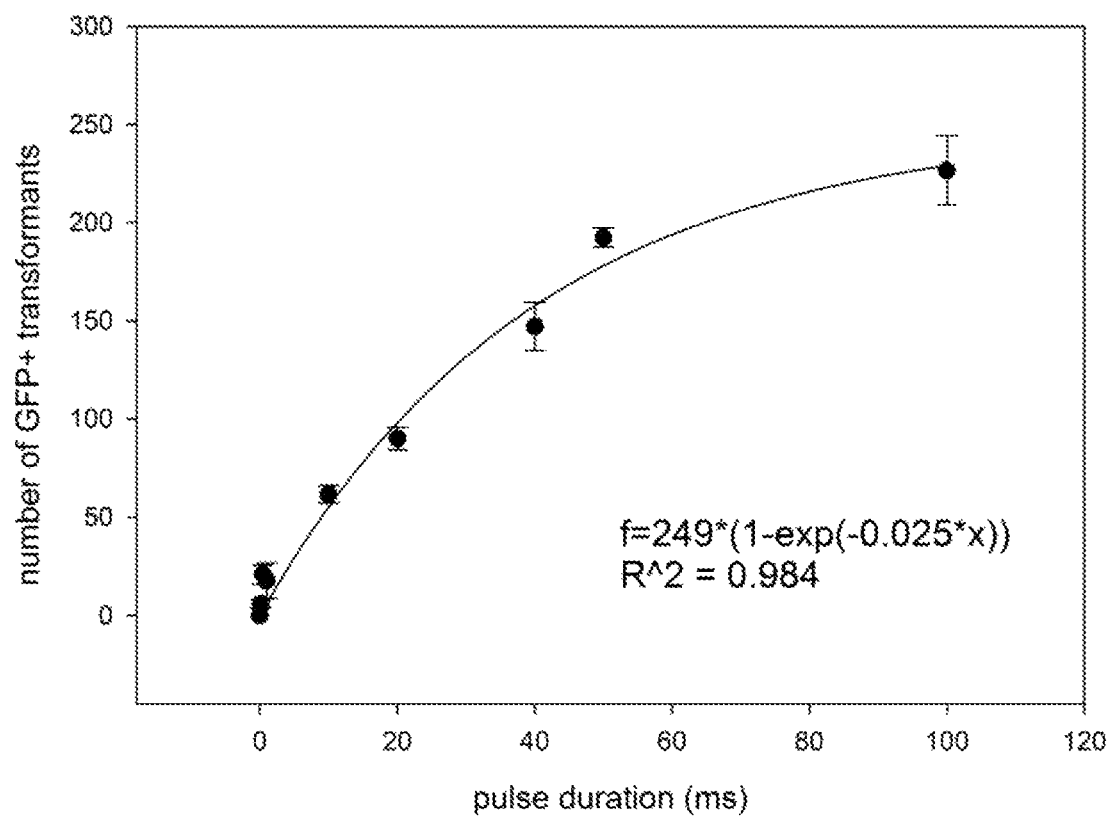

FIG. 19 shows the efficiency of transformation of HEK293 cells with a GFP reporter cDNA construct as a function of length of electroporation pulse (40V and 5 pulses).

Figure 20:
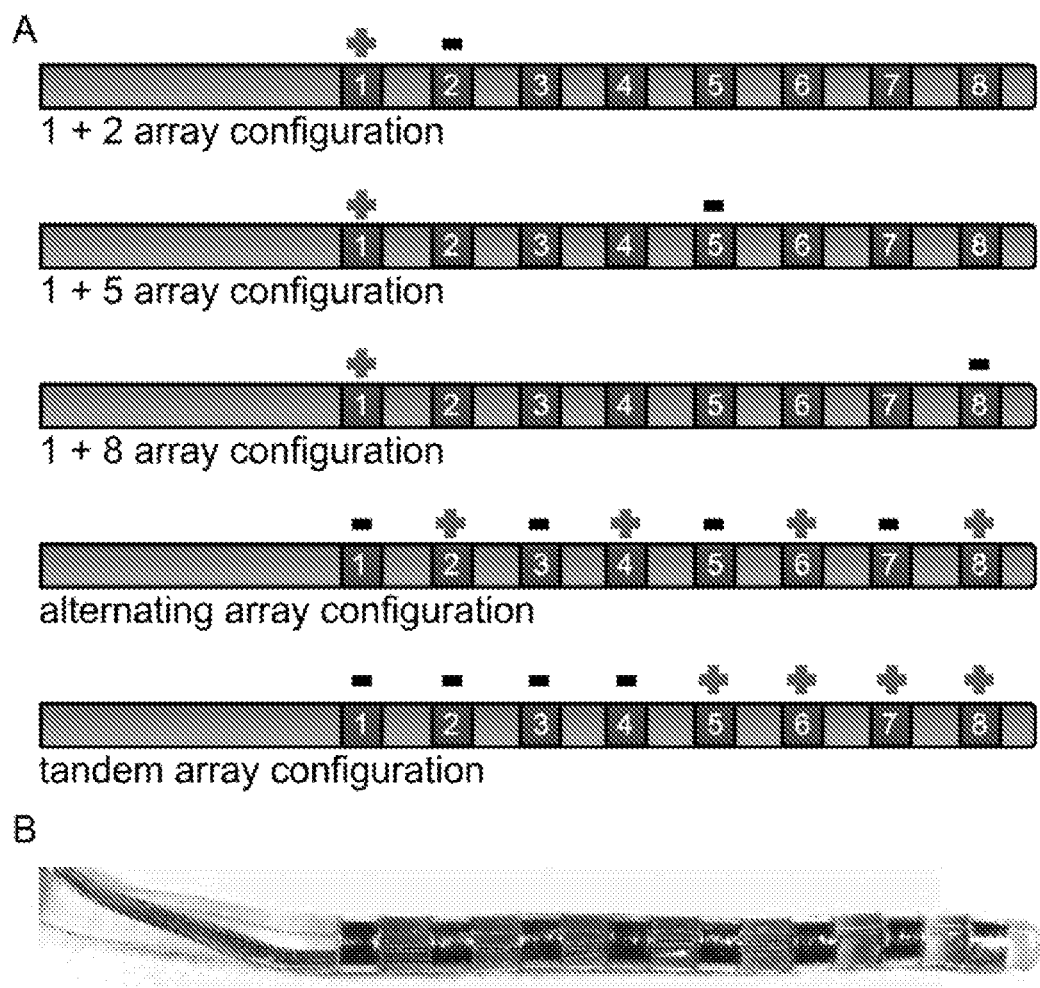

FIG. 20 shows A) Cochlear implant anode and cathode array configurations employed in Examples 2 and 8; and B) a photomicrograph of an actual 8-node Cochlear implant linear electrode array (aligned with the array configuration representations).

Figure 21:
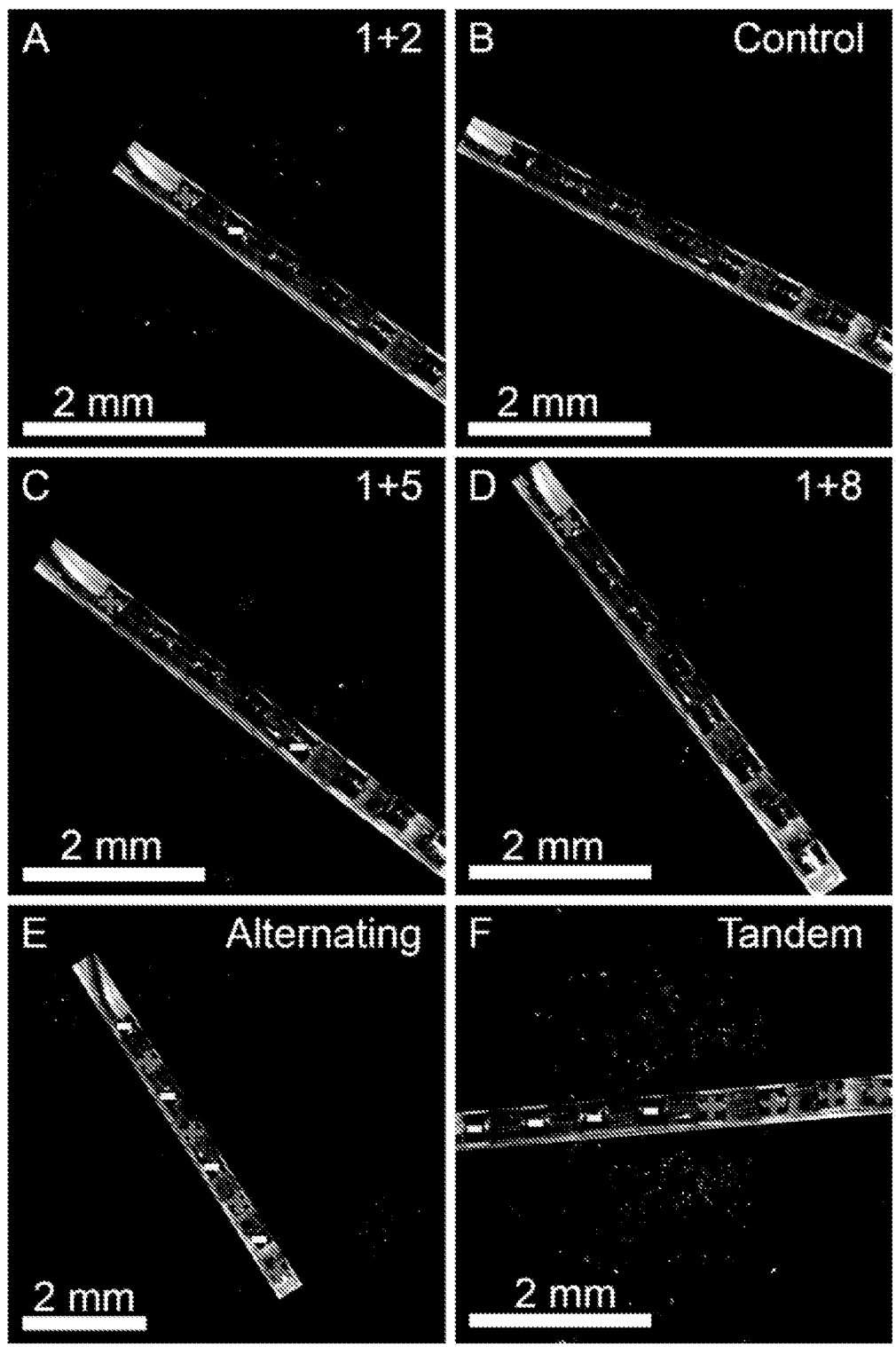

FIG. 21: Nuclear localised GFP fluorescence indicates HEK293 cells transformed by CFE. A, C-F (B=control), show examples of different electrode array configurations.

Figure 22:
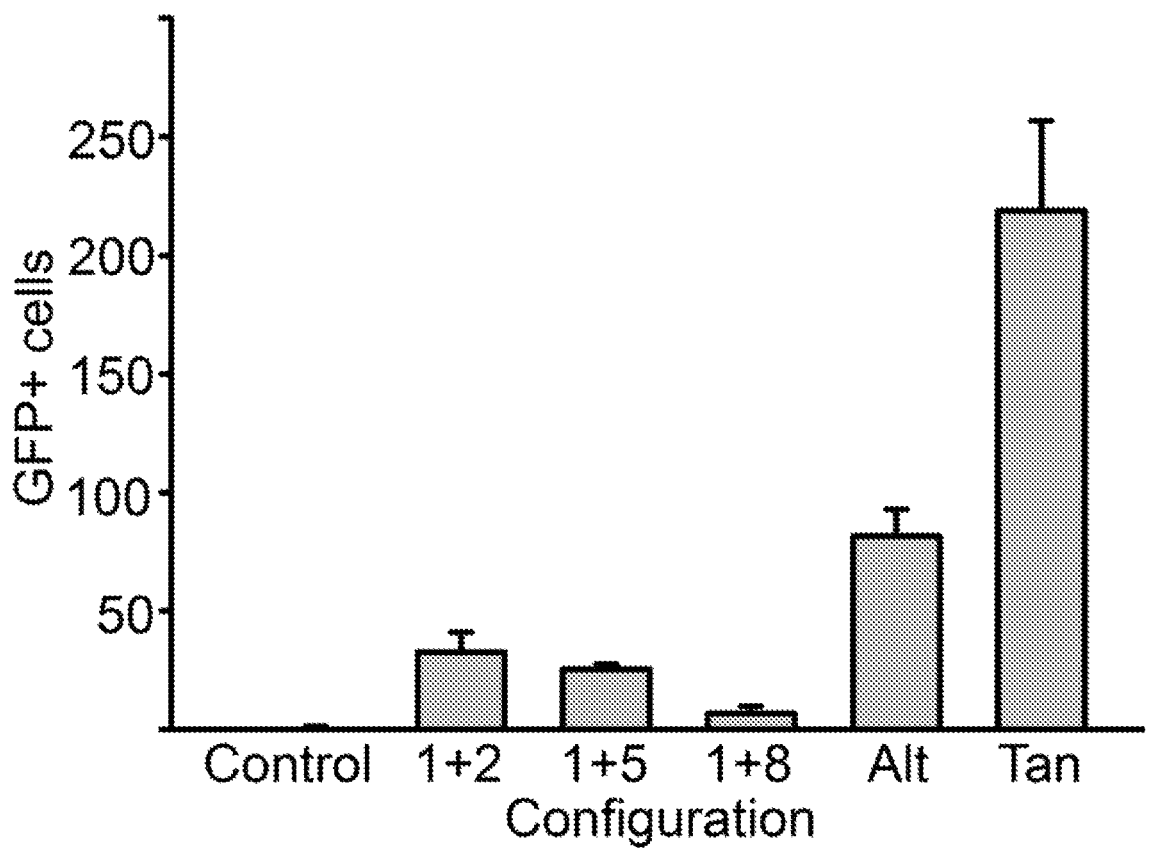

FIG. 22: Summary of data obtained from experiment illustrated in FIG. 21, indicating the mean+/−SEM number of transformed cells per experiment. * indicates P<0.02; ** P<0.001; ranked ANOVA with Holm-Sidak post-hoc pairwise comparisons. B. Control, plasmid DNA with the electrode array, without CFE. Position of electrode is overlaid schematically. All experiments utilised 40V, 10 pulses, 50 ms duration.

FIG. 23 shows the effect of voltage amplitude on cell transformation with 'tandem' electrode configuration CFE. CFE was delivered using 10 pulses at 40 ms duration, with varying voltage. Summary of data, indicating the mean+/−SEM number of transformed cells per experiment. * indicates P<0.05; ranked ANOVA with Tukey's test post-hoc pairwise comparisons. All experiments utilised 40 ms duration, 10 pulses, 1/s.

FIG. 24 shows the effect of pulse number of transformation efficiency with 'tandem' electrode configuration CFE. CFE was delivered using 20 and 40V with 40 ms duration, with varying pulse number. Summary of data. indicating the mean+/−SEM number of transformed cells per experiment. * indicates P<0.001 and ** P<0.05; ranked two-way ANOVA with Holm-Sidak method post-hoc pairwise comparisons.

Figure 25:
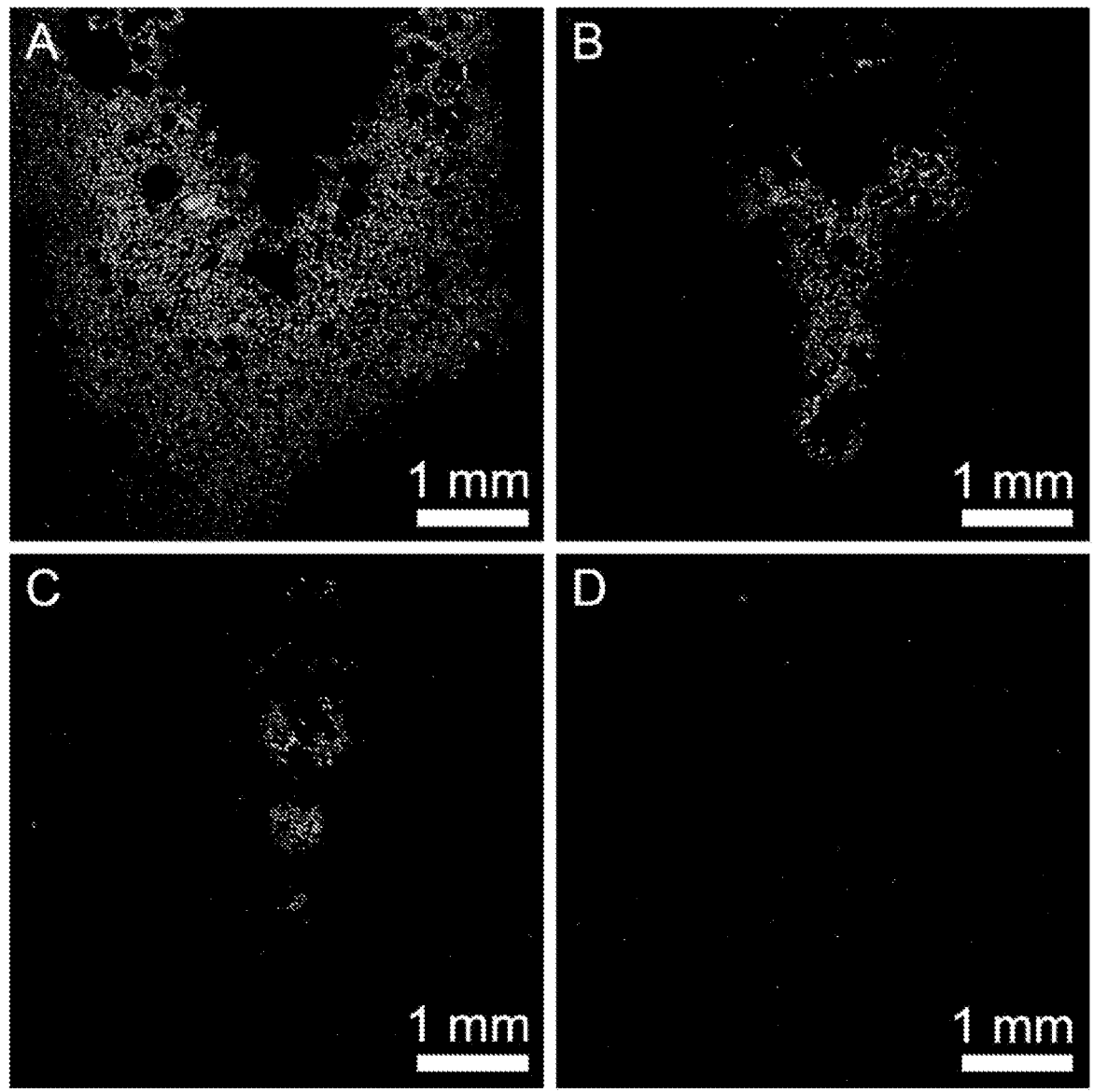

FIG. 25 shows the effect of increasing pulse number on cell death. A. Image showing dead cells labelled with propidium iodide 30 min after Tandem CFE (40 pulses, 40 V, 40 ms) localised close to the electrode array. B. Propidium iodide fluorescence at 30 mins post-CFE with 5 pulses. C. Propidium iodide fluorescence at 30 mins post-CFE with 1 pulse. D. Propidium iodide fluorescence at 30 mins with no-CFE (control).

Figure 26:
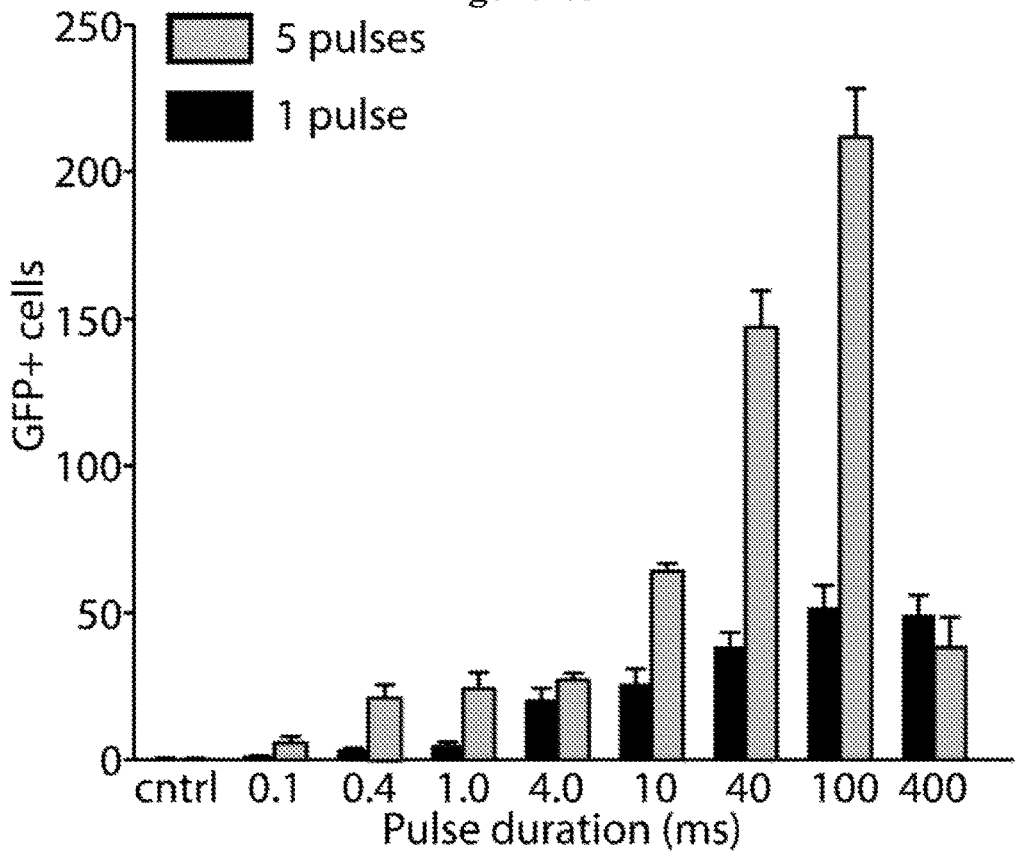

FIG. 26 shows the effect of pulse duration on number of transformed cells with 1 or 5 pulses via 'tandem' electrode configuration CFE, with 40 V and varying pulse duration. Summary of data indicating the mean+/−SEM number of transformed cells per experiment. * indicates P<0.001 and ** P<0.05; ranked ANOVA with Holm-Sidak method post-hoc pairwise comparisons. One pulse per second was delivered for the 5 pulse test. Cntrl; no CFE control.

Figure 27:
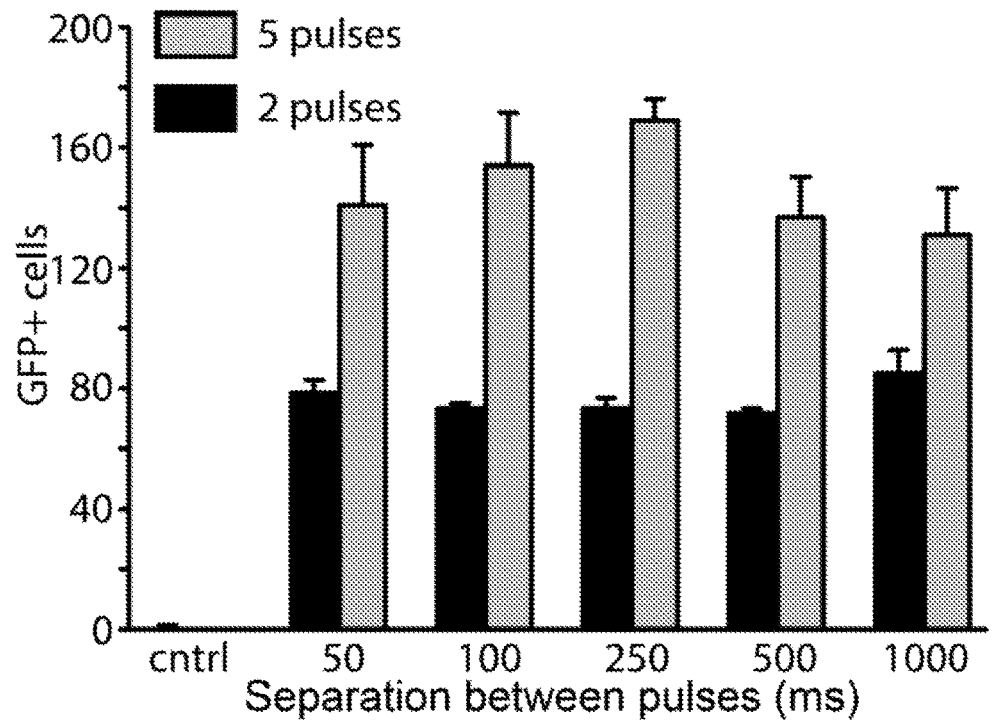

FIG. 27 shows the effect of gap duration on number of transformed cells with 2 or 5 pulses via 'tandem' electrode configuration CFE, with 40 V pulses 40 ms in length and varying gap duration. Summary of data indicating the mean+/−SEM number of transformed cells per experiment. * indicates P<0.001 and ** P<0.05; ranked ANOVA with Holm-Sidak method post-hoc pairwise comparisons. Cntrl; no CFE.

Definitions

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, reference to "a" or "one" element does not exclude the plural, unless context determines otherwise. For instance, reference to "a nucleic acid molecule" should not be read as excluding the possibility of multiple nucleic acid molecules.

As used herein, the term "close electric field" refers to an electric field formed between a positive electrode (anode) or anode array and a negative electrode (cathode) or cathode array, wherein the cathode or cathode array and the anode or anode array are separated by between about 10 μm and about 5 mm or less, typically between about 50 μm and about 1 mm or less, and even more typically between about 50 μm and about 0.5 mm or less, where the distance between the cathode or cathode array and the anode or anode array is measured as the distance between the proximal edges of the closest cathode and anode pairing.

As used herein, the term "subject" refers to any organism that may benefit from transfection of an agent into one or more of its cells, or an organism the transfection of which is desired for any other reason, such as to modify the organism's performance under certain conditions, or its ability to utilise or tolerate certain substances. According to an embodiment the subject is an animal, such as a mammal, including, but not limited to any one of humans, non-human primates, dogs, cats, horses, rodents, and the like. Typically, the terms "subject" and "patient" are used interchangeably herein. Typically the subject is a human.

As used herein, the term "non-human animals" refers to non-human vertebrate animals including, but not necessarily limited to, rodents, non-human primates, ovines, bovines, ruminants, lagomorphs, porcines, caprines, equines, canines, felines, aves, etc.

As used herein, the term "nucleic acid molecule" refers to any nucleic acid containing molecule, including but not limited to DNA or RNA molecules. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-carboxymethylaminomethyl-2-thiouracil, 5-carboxymethylaminomethyluracil-, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine, A nucleic acid molecule may include modifications designed to improve delivery into cells, stability once inside a cell, and/or binding to the appropriate intracellular target.

The nucleic acid molecule may be an oligonucleotide or a polynucleotide. The nucleic acid molecule may be naked DNA, such as cDNA, or naked RNA. The nucleic acid may comprise encapsulated DNA or RNA, such as polynucleotides present in liposomes or microspheres, particularly where such encapsulation improves the stability of the agent or the efficiency of transfection by electroporation. The use of encapsulated DNA or RNA may offer a less advantageous embodiment if encapsulation allows transfection of cells which are distant to the electrode to take place. It will be understood by a person skilled in the art that particles may be mixed with the nucleic acid molecule to condense the nucleic acid molecule, which may provide increased transduction efficiency.

The terms "in operable combination," "in operable order," and "operably linked" as used herein refer to the linkage of nucleic acid molecule sequences in such a manner that a nucleic acid molecule capable of directing the transcription of a given sequence and/or the synthesis of a desired polypeptide product is produced. The term also refers to the linkage of amino acid sequences in such a manner so that a functional protein is produced.

The terms "expression vector" or "expression cassette", as used herein, refer to a recombinant DNA molecule containing at least one desired coding sequence and appropriate nucleic acid sequences necessary for the expression of the operably linked coding sequence in a particular host organism. Nucleic acid sequences necessary for expression in eukaryotic cells are known to utilize promoters, enhancers, and termination and polyadenylation signals.

As used herein, the term "transfection" refers to the transfer of an agent, including but not limited to a nucleic acid molecule, a peptide or a protein, into the cytoplasm and/or nucleus of a cell by electroporation. The agent may be a nucleic acid molecule, and may encode a polypeptide product which is expressed by the cell. Alternatively, the nucleic acid molecule may act upon the transcription and translation machinery of the cell. A transfected cell may carry the nucleic acid molecule product permanently if the nucleic acid molecule agent is stably incorporated into the cell's genome. A transfected cell may carry the nucleic acid molecule product transiently if the nucleic acid molecule agent is not incorporated into the cell's genome, or the expression cassette and vector may retain expression viability but may not integrate into the chromosomal DNA (episomal expression).

DETAILED DESCRIPTION

The present invention is based on studies which surprisingly found that certain configurations of cochlear implant electrode microarrays, resulting in small intense electrical fields occurring at the cellular level, resulted in surprisingly more efficient and more targeted electroporation and resulting transfection, compared with previously published studies. In particular, high transformation efficiencies were obtained at voltages as low as 10V and at significantly reduced total delivered charge.

These results now show that highly efficient and highly targeted transfection of cells in vivo is possible, allowing for bioactive agent therapy, such as gene therapy, targeted at specific groups of cells within a subject with minimal effects on surrounding cells. Such methods may find application in control, reversal, compensation for, and possibly even cure of neurological conditions or defects including nerve degeneration or damage of a cerebral, spinal, otological, optical or other sensory nature, and/or other physiological conditions or defects affecting the muscoskeletal, cardiovascular, respiratory, gastrointestinal, integumentary, urinary, reproductive, immune or endocrine systems. The methods may be utilized to deliver targeted cancer treatment. Because of the spatial specificity and efficiency of the methods of the present invention, particular areas of the brain or spinal nerve may be more readily and safely treated, and conditions not previously considered treatable may now be addressed.

The methods described herein allow the use of targeted and efficient gene therapy which may, for example, enhance the expression of spiral ganglion cell trophic molecules, such as brain-derived neurotrophic factor, in cochlear cells which lie close to the cochlear implant. This is proposed to be beneficial to the function of the cochlear implant by promoting spiral ganglion cell neurite outgrowth specifically towards the transformed cells, which in turn bring the spiral ganglion neuron processes in close proximity to the cochlear implant electrodes. By providing spiral ganglion neurite outgrowth close to the position of the cochlear implant, the functionality of the cochlear implant may be improved by lowering the required stimulation currents. The use of lowered stimulation currents may enable the electrode design of the cochlear implant to include a higher density of electrodes when working as a bionic ear, thus also improving the auditory information bandwidth that can be delivered to the cochlear nerve.

Electroporation

The methods described herein use close electric field to deliver an agent into the cytoplasm or nucleus, or both, of cells within a restricted target region.

The close electric field arises from the proximity of the electrodes used, such as micron-sized electrodes within cochlear microarrays, and the resulting uniformity and intensity of the resulting electric field for a given voltage.

For the purposes of electroporation a cathode and an anode is required. The cathode and anode may be introduced to the target region for treatment as separate electrodes or as components of a single device, such as an electroporation probe. The cathode and/or anode may, independently, also comprise a single electrode or a plurality or array of electrodes.

The cathode or cathode array and the anode or anode array may be separated by between about 10 µm and about 5 mm, such as between about 10 µm and about 4 mm, between about 10 µm and about 3 mm, between about 0 µm and about 2 mm, between about 10 µm and about 1.5 mm, between about 10 µm and about 1 mm, between about 10 µm and about 0.75 mm, between about 10 µm and about 0.5 mm, between about 10 µm and about 0.4 mm, between about 10 µm and about 0.3 mm, between about 10 µm and about 0.2 mm, any of the foregoing ranges in which the lower limit is 50 µm instead of 10 µm or any of the foregoing ranges in which the lower limit is 100 µm instead of 10 µm, between about 10 µm and about 0.1 mm, between about 10 µm and about 50 µm, between about 10 µm and about 25 µm, about 10 µm, about 25 µm, about 50 µm, about 75 µm, about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, about 0.9 mm, about 0.95 mm, about 1 mm, about 1.5 mm, about 2 mm, about 3 mm, about 4 mm or about 5 mm.

The cathode, or electrodes in the cathode array, and the anode, or electrodes in the anode array, may comprise electrically conductive, non-toxic or bio-inert metal, for instance platinum, gold, tungsten, or stainless steel. The electroporation electrode may be electrically conductive over or along its entire surface. Alternatively, the electroporation electrode may be electrically conductive at its surface along one or more portions of the entire length of the electrode, and electrically non-conductive at its surface along another portion or portions of its length. The non-conductive portions may be insulated at the surface of the electrode with a coating, such as a resin or plastic coating. The non-conductive portions may be made of a non-conducting material, such as a resin or plastic. Conductive and non-conductive polymer materials and hydrogel materials may also be used. This may include molecular pore size determination to provide appropriate spatiotemporal delivery of the DNA within the effective range for close-field electroporation. The electrode(s) may be 'point' source(s) or sink(s) connected to power source(s) via insulated conductive lines. The electrodes may be of any desired shape, such as square, spherical, circular, oblong or elongated of any of the foregoing, cylindrical, etc. In an embodiment, each electrode may be, independently, less than 1 mm in one or more dimensions and may have one or more dimensions in the nanometre range (including less than 5 nm). Typically, the electrode(s) may have one or more dimensions of less than 0.75 mm, less than 0.5 mm, less than 0.4 mm, less than 0.3 mm, less than 0.2 mm, less than 0.1 mm, less than about 50 µm, less than about 25 µm, less than about 10 µm, less than about 5 µm, less than about 1 µm, about 0.025 mm, about 0.05 mm, about 0.075 mm, about 0.1 mm, about 0.125 mm, about 0.15 mm, about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, or about 0.75 mm. In an embodiment, all dimensions of an electrode for use in a method according to the present invention comply with the above listed dimensions and, in a further embodiment, all dimensions of all electrode(s) for use in a method according to the present invention comply with the above listed dimensions.

The cathode or cathode array and the anode or anode array may be configured in any convenient manner allowing for the separations described herein, and configurations may include a single cathode and anode, a single cathode and a plurality of anodes, a single anode and a plurality of cathodes, or a plurality of anodes and a plurality of cathodes. The cathode or cathode array and the anode or anode array may be counterpositioned on opposite sides of the target region for electroporation, or the cathode or cathode array and the anode or anode array may be placed end to end such that the close electric field flows along an axis defined by the cathode or cathode array and the anode or anode array. Another potential configuration contemplated by the present invention comprises a cathode or anode array comprising a plurality of electrodes arranged around one or a few electrodes of opposite polarity. An example of such an arrangement may comprise a hexagonal array of electrodes surrounding or in the proximity of a single electrode of opposite polarity as illustrated in FIG. 2B. This is described as a planar array.

The electrodes or arrays thereof may be inserted into or next to the target region before or after the agent is introduced into the target region.

In certain embodiments of the methods described herein, at least one electrode which is used for electroporation is provided by a cochlear implant. The term "cochlear implant" or "cochlear implant device" as used herein refers to a device which is at least partially implanted in the scala tympani or the scala vestibuli of the cochlea for the purpose of restoring hearing by direct electrical stimulation of the cochlear nerve. A cochlear implant is commonly termed a "bionic ear". Examples of cochlear implants and/or electrodes for cochlear implants are described in U.S. Pat. No. 7,451,000 (Cochlear Limited), U.S. Pat. No. 7,406,352 (Cochlear Limited); U.S. Pat. No. 7,367,992 (Cochlear Limited), U.S. Pat. No. 7,349,744 (Cochlear Limited); U.S. Pat. No. 7,346,397 (Cochlear Limited), U.S. Pat. No. 7,340,308 (Advanced Cochlear Systems, Inc.), U.S. Pat. No. 7,319,906 (Advanced Bionics Corporation), U.S. Pat. No. 7,317,944 (Advanced Bionics Corporation), and U.S. Pat. No. 7,315,763 (Advanced Bionics Corporation), the entire contents of each of which is incorporated by reference.

A cochlear implant possesses at least one electrode and more typically a series of independently addressable electrodes along the length of the region of the implant lying within the cochlea, with each electrode electrically insulated from other electrodes, forming a microarray. An example of a cochlear implant used in proof of principle studies here has a linear implant electrode microarray comprising 8 platinum ring electrodes, each having a diameter of approximately 400 µm and a depth of approximately 350 µm, each separated by a space of approximately 350 µm, for a total microarray length of just over 5 mm. During the normal operation of the cochlear implant, the electrodes receive stimuli originating from an external control unit and provide an electrical stimulus to the spiral ganglion cells by creating a voltage between the electrodes in a bimodal fashion to prevent polarization of the electrodes. In this normal neural interface mode, the stimulus to the nerve fibres may be unipolar, with one or more electrodes delivering current to a distant reference electrode, or bipolar, with current return between various array electrodes.

For the electroporation methods described herein, in certain embodiments some or all of the electrodes of the cochlear implant may act as a single electrode. In other embodiments, individual electrodes or groups of electrodes may act as an electrode array and other individual electrodes or groups of electrodes may act as a second electrode array. In certain embodiments the cochlear implant may provide a plurality of electrodes and second electrodes. Examples of configurations of electrodes and/or dedicated electroporation electrodes on a cochlear implant are illustrated in FIG. 1*d* and FIG. 4.

According to an embodiment the distal four electrodes form an electrode array of one polarity and the proximal four electrodes form an electrode array of opposite polarity in a 'tandem' microarray.

In an alternative embodiment, all the electrodes, or specific electrodes along the implant, may be used to generate a transient dielectric breakdown of the lipid bilayer of the plasma membrane of the target cells. In one embodiment, this may be performed by simultaneously polarizing some or all of the electrodes relative to at least one separate second electrode which is located close to the cochlear implant microarray, to provide a current return path. This second electrode is typically the cathode (negative) terminal relative to the electrodes of the electrode array.

Electrode arrays comprising interspersed electrode couplings, such as alternating arrays in which anodes and cathodes alternate with one another, may result in interference between the respective fields, possibly resulting in less intense or more dispersed electric fields compared to fields generated by discrete anode and cathode electrodes or between discrete anode and cathode arrays, and may result in less efficient transformation and poorer specificity of localisation of transformation. According to an embodiment, interspersed electrode couplings, such as alternating arrays are excluded from the scope of the present invention. According to another embodiment, the electrode arrays are configured as distinct or separated polarities.

Current may be delivered to and from the electrode(s) via connection to external (ie. outside of the subject) electroporation circuitry. Alternatively, the current for electroporation may be provided by dedicated circuitry in an electrode-bearing implant, such as a cochlear implant. In such embodiments the dedicated circuitry generates the required electrical pulse profile in an electroporation mode for use during the implantation procedure and at later stages if additional gene transfection is performed. The implant stimulator may then be switched to a conventional stimulus mode for operation as, for example, a cochlear prosthesis/auditory nerve stimulator. In certain embodiments dedicated electroporation electrodes included in an implant are not used in the normal operation of the implant.

In certain embodiments, cochlear implants are provided in which one or more dedicated electroporation electrodes are built into the implant for the purpose of providing the electroporation stimulus to the cochlear tissue. These dedicated electrodes may be driven via an external isolated electroporation-driving circuit, or the one or more dedicated electroporation electrodes could be driven externally by electroporation circuitry. In certain embodiments the dedicated electroporation electrodes are not used in the normal operation of the cochlear prosthesis in providing direct electrical stimulus to the spiral ganglion cells as a result of auditory stimulation.

The electroporation stimulus is typically provided in a square wave voltage configuration, delivering from a 0 Volt reference about 1V to about 100V, such as from about 1V to about 75V, about 1V to about 50V, about 1V to about 40V, about 1V to about 30V, from about 1V to about 25V, from about 1V to about 20V, from about 1V to about 15V, from about 1V to about 10V, from about 1V to about 5V, from about 5V to about 50V, from about 10V to about 50V, from about 15V to about 50V, from about 20V to about 50V, from about 25V to about 50V, from about 30V to about 50V, from about 10V to about 50V, from about 10V to about 40V, from about 10V to about 30V, about 5V, about 10V, about 15V, about 20V, about 25V, about 30V, about 35V, or about 40V.

Currents applied in the course of electroporation methods according to the present invention may be controlled or uncontrolled and will depend on the material within which the method is being carried out (as different materials will have different resistances), the area or volume over which the electric field is spread (which will depend on the configuration and shape of the anode and or cathode or arrays thereof) and will also depend on whether anodes and cathodes are interspersed such that interference between electric fields occurs or not (which will increase the current required for a given electric field strength). For a linear anode and cathode array configuration, for example as illustrated in FIG. 3 or equivalent, it may be desirable to deliver the electroporation current using current sources rather than voltage sources. In this case the current supplied to each electrode may be from about 1 μA to about 150 mA, such as from about 1 mA to about 100 mA, from about 1 mA to about 75 mA, from about 1 mA to about 50 mA, from about 1 mA to about 40 mA, from about 1 mA to about 30 mA, from about 1 mA to about 25 mA, from about 1 mA to about 20 mA, from about 1 mA to about 15 mA, from about 1 mA to about 10 mA, from about 1 mA to about 5 mA, from about 2 mA to about 50 mA, from about 5 mA to about 50 mA, from about 10 mA to about 50 mA, from about 15 mA to about 50 mA, from about 20 mA to about 50 mA, from about 30 mA to about 50 mA, from about 5 mA to about 40 mA, from about 5 mA to about 30 mA, from about 5 mA to about 20 mA, from about 10 mA to about 20 mA, about 1 mA, about 2 mA, about 3 mA, about 5 mA, about 7 mA, about 10 mA, about 15 mA, about 20 mA, about 25 mA, about 30 mA, or about 40 mA.

Total charge (Coulombs) applied in the course of electroporation methods according to the present invention may also be controlled or uncontrolled and as per current, described above, will depend on the material within which the method is being carried out, the area or volume over which the electric field is spread (which will depend on the configuration and shape of the anode and or cathode or arrays thereof) and will also depend on whether anodes and cathodes are interspersed such that interference between electric fields occurs or not (which will increase the current required to generate a given electric field strength). For a linear anode and cathode array configuration, for example as illustrated in FIG. 3 or equivalent, the charge delivered may be from about 1 μC to about 1 C/electrode per pulse. The charge may depend upon the number of electrodes, voltage and pulse width. Expressing this as per electrode per pulse enables the addressing of very broad operational ranges—for example 1 μC is the charge delivered to each of four of the 8 electrodes in one polarity at 4 Volts for 100 μs. Ignoring the roughness factor (the fine 3-dimensional structure of platinum electrodes), the minimum effective charge density on platinum electrodes may be between about 1 mC/cm$^2$ and about 1 C/cm$^2$, such as between about 5 mC/cm$^2$ and about 500 mC/cm$^2$, between about 10 mC/cm$^2$ and about 400 mC/cm$^2$, between about 15 mC/cm$^2$ and about 350 mC/cm$^2$, between about 20 mC/cm$^2$ and about 300 mC/cm$^2$, between about 25 mC/cm$^2$ and about 250 mC/cm$^2$, between about 30 mC/cm$^2$ and about 200 mC/cm$^2$, between about 40 mC/cm$^2$ and about 150 mC/cm$^2$, between about 50 mC/cm$^2$ and about 100 mC/cm$^2$, about 10 mC/cm$^2$, about 15 mC/cm$^2$, about 20 mC/cm$^2$, about 250 mC/cm$^2$, about 30 mC/cm$^2$, about 40 mC/cm$^2$, about 50 mC/cm$^2$, about 60 mC/cm$^2$, about 70 mC/cm$^2$, about 80 mC/cm$^2$, about 100 mC/cm$^2$, about 120 mC/cm$^2$, about 150 mC/cm$^2$, about 200 mC/cm$^2$, or about 250 mC/cm$^2$.

The electroporation stimulus may be delivered as pulses of from about 100 μs to 10 s duration, such as from about 1 ms to about 500 ms, from about 1 ms to about 300 ms, from about 1 ms to about 200 ms, from about 1 ms to about 150 ms, from about 1 ms to about 100 ms, from about 1 ms to about 75 ms, from about 1 ms to about 50 ms, from about 0.1 ms to about 5 ms, from about 5 ms to about 25 ms, from about 20 ms to about 50 ms, from about 50 ms to about 100 ms, from about 50 ms to about 200 ms, from about 50 ms to about 300 ms, from about 50 ms to about 500 ms, about 10 ms, about 20 ms, about 30 ms, about 40 ms, about 50 ms, about 60 ms, about 70 ms, about 80 ms, about 90 ms, about 100 ms, about 150 ms, or about 200 ms.

Multiple pulses are commonly used, with typically from 1 to 500 pulses, such as 1 to about 400 pulses, from 1 to about 300 pulses, from 1 to about 200 pulses, from 1 to about 100 pulses, from 1 to about 75 pulses, from 1 to about 50 pulses, from 1 to about 40 pulses, from 1 to about 30 pulses, from 1 to about 20 pulses, from 1 to about 10 pulses, 2 pulses, about 5 pulses, about 10 pulses, about 15 pulses, about 20 pulses, about 25 pulses, about 30 pulses, about 50 pulses, about 75 pulses, about 100 pulses, about 20 pulses, about 300 pulses, about 500 pulses.

The interval between electrostimulation pulses may be from about 0.1 to about 30 seconds, such as from about 0.1 s to about 20 s, from about 0.1 s to about 1 s, from about 0.1 s to about 5 s, from about 0.1 s to about 4 s, from about 0.1 s to about 3 s, from about 0.1 s to about 2 s, from about 0.1 s to about 1 s, from about 0.1 s to about 0.5 s, from about 0.1 s to about 0.3 s, from about 0.1 s to about 0.2 s, from about 0.5 s to about 1 s, from about 0.5 s to about 2 s, from about 0.5 s to about 5 s, about 0.5 s, about 0.75 s, about 1 s, about 1.5 s, about 2 s, about 3 s, about 4 s, about 5 s, or about 10 s.

The delivery of the electroporation current during the electroporation procedure for delivery of an agent may last from about 100 μs to about 20 minutes, depending upon the number of pulses and delay between pulses if more than one pulse is applied.

Ramped waveforms may also be used, as these may provide a faster onset of electroporation dielectric breakdown of the cell membrane for agent delivery, while minimizing current delivery. As such stimuli delivered to the intact cochlea of a subject may be perceived by the subject as excessively loud noise, typically the subject will be under general anaesthetic during electroporation.

According to an embodiment of the present invention, the electroporation stimulus is provided in up to 40 pulses of about 50 to about 100 ms duration separated by intervals of from about 0.5 to about 2 seconds, such as pulses of 50 ms duration separated by intervals of 950 ms, and delivered in a square wave configuration, at a voltage of from 10 to 40V, with a current of up to about 20 mA and total charge of less than 100 mC, with the gap between the cathode or cathode array and the anode or anode array being up to about 1 mm, more typically less than 0.5 mm.

In addition to the above, the positive (anode) and negative (cathode) arrays may be switched within an electrode array between pulses or groups of pulses. It is contemplated that this may allow for shaping of fields for electroporation and DNA transfer in 3 dimensional space.

Subjects and Target Regions

The present invention contemplates the transfection of any cells within any target region. The target region may be inside or outside an organism. According to an embodiment the target region is in or on a human or non-human organism, such as within an organ inside a human or non-human animal. In another embodiment, the target region may be a region on or in a surface or volume comprising cells to be transfected such as, for example, a region on or in a medium in a Petri dish or other culture vessel, a region in an explanted organ. According to embodiments, the present invention finds its main application in transfection of cells within a target region in a human or non-human animal. According to an embodiment, the subject is human. According to another embodiment, the subject is a non-human mammal, such as, but not limited to, a dog, cat, horse, or rodent.

In embodiments, the spacial accuracy and transformation efficiency of electroporation methods of the present invention will find application in a wide range of treatments of human and non-human animals, especially in correction or repair of defects or damage in localised regions in said animal(s). Non-limiting examples may include transfection of otic cells, such as cochlear mesenchymal cells, or nerve- or nerve-associated cells, including brain cells and optic cells (retina, optic nerve) to express neurotrophic factors to encourage or restore growth of nerves or re-myelination of cells to improve, establish or re-establish neural connections. Such methods may be for treating, correcting, halting or slowing down progression of or onset of, or at least ameliorating conditions including deafness, muscular dystrophy, Parkinson's disease, or spinal injury. Other examples may comprise transfection of particular cell types within an organ, such as the skin, skeletal or smooth muscle, liver, kidney, heart, pancreas, gastrointestinal system, reproductive organs, or the central and peripheral nervous systems, including the autonomic and enteric nervous systems, or a tumour, to provide, correct, improve or inhibit an activity in the target region. Methods according to the present invention may also find application in, or association with bionics other than cochlear implants.

Cells of particular interest include post-mitotic cells, such as neurons and sensory cells, such as cochlear hair cells, which may not be replaced by the body. Data reported herein indicates that functionality may be restored to such cells by methods according to the present invention comprising somatic cell gene therapy.

Electrodes or electrode arrays may be purpose-designed for particular applications or may be reconfigured electrodes of a cochlear implant electrode microarray. For transfection of cells within target regions well within the body of a subject, or well within an organ inside said subject, a long, thin/narrow shaft is contemplated as an embodiment, with the electrodes arranged at the tip either transversely or axially. In other methods, planar microarrays consisting of sheets of electrode nodes would be matched to the region targeted for close-field electroporation for delivery of the therapeutic molecules.

Where the methods described herein are intended for treatment of cochlear cells, the cochlea may be present in situ within a live subject. Where the methods described herein are intended for experimental or research purposes the cochlea may be present in situ within a live subject or may be substantially intact but isolated from the subject.

Cells which may be transfected by the methods described herein may be cells lying within less than 5 mm of an electrode, such as less than 4 mm, less than 3 mm, less than 2 mm, less than 1.5 mm, less than 1 mm, less than 0.75 mm, less than 0.5 mm, less than 0.4 mm, less than 0.3 mm, less than 0.2 mm, less than 0.1 mm, less than about 50 µm, about 50 µm, about 0.1 mm, about 0.15 mm, about 0.2 mm, about 0.25 mm, about 0.3 mm, about 0.35 mm, about 0.4 mm, about 0.45 mm, about 0.5 mm, about 0.6 mm, about 0.7 mm, about 0.8 mm, about 0.9 mm, about 1 mm, or about 2 mm. According to an embodiment, cells transfected by the methods described herein are within 3 mm of an electrode. According to an embodiment, cells transfected by the methods described herein will be cochlear mesenchymal cells.

In particular embodiments a subject's cochlea is a mature cochlea, which as used herein refers to a developmental stage of the cochlea within which air-borne sound transduction takes place. In rodents such as rats, mice and guinea pigs, this typically occurs around one week after birth. In humans air-borne sound transduction commences at birth.

Methods according to the present invention may be for transient expression of an agent by the cells within the target region, or may be for transfection and integration of a desired nucleic acid into the cell's genome for permanent transfection, or permanent expression of the expression vector without integration. Expression of a nucleic acid transfected into a particular cell or cell type in a target region may be inducible or constitutive, depending on the regulatory regions, such as promoters, associated with the nucleic acid, or by direction through manipulation of the close electric field properties.

Agents

Nucleic Acid Molecules

In certain embodiments, the agent may consist of a nucleic acid molecule. In certain embodiments the agent may comprise a nucleic acid molecule, in which case the agent may, for example, also comprise molecules which enhance the stability or transfection efficiency of the nucleic acid molecule, such as chitosan, and/or may also comprise non nucleic acid molecules such as small neuroprotective peptides.

(a) Nucleic Acid Molecules which Encode a Polypeptide Product

The agent may be a nucleic acid molecule which encodes a polypeptide product. The expression of the encoded polypeptide product promotes a desired outcome, such as promoting or maintaining neural outgrowth and/or survival.

The encoded polypeptide product may be a polypeptide endogenous to the subject. In certain embodiments the encoded polypeptide product is an exogenous polypeptide.

The nucleic acid molecule which encodes a polypeptide product comprises a coding sequence for a polypeptide product or a precursor polypeptide of the polypeptide product. The polypeptide product may be a full-length polypeptide which occurs in nature, or it may be a portion of a polypeptide which occurs in nature, provided that the desired activity or functional properties (such as receptor binding and/or the ability to induce signal transduction) of the polypeptide product are retained. The nucleic acid molecule may also comprise a sequence located adjacent to the coding sequence on the 5' or 3' end of the coding sequence or on both the 5' and 3' ends for a distance of about 1 kb or more on either end such that the sequence corresponds to the length of a full-length mRNA sequence. Sequences located 5' of the coding region and present on the mRNA are referred to as 5' non-translated sequences. Sequences located 3' or downstream of the coding region and present on the mRNA are referred to as 3' non-translated sequences.

The nucleic acid molecule may comprise a cDNA sequence encoding a polypeptide product. The nucleic acid molecule may comprise a genomic sequence encoding a polypeptide product. A genomic sequence contains the coding region interrupted with non-coding sequences termed "introns" or "intervening regions" or "intervening sequences." Introns are segments of a gene that are transcribed into nuclear RNA (nRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In certain embodiments, the expression of a nucleic acid molecule refers to the process of converting genetic information encoded in the nucleic acid molecule into RNA (including for example mRNA or snRNA) through "transcription" of the nucleic acid molecule (i.e., via the enzymatic action of an RNA polymerase), and for nucleic acid molecules encoding a polypeptide, into a polypeptide product through translation of mRNA. Expression can be regulated at many stages in the process. "Up regulation" refers to regulation that increases the production of expression products (i.e., RNA or protein), while "down regulation" refers to regulation that decreases production. Molecules (e.g., transcription factors) that are involved in up regulation or down regulation are often called "activators" and "repressors" respectively.

In addition to containing introns, genomic forms of a nucleic acid molecule may also include sequences located on both the 5' and 3' end of the sequences that are present on an RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

A nucleic acid molecule may be present in a cDNA, genomic DNA or RNA form. When present in a DNA form, the nucleic acid molecule may be single-stranded (i.e., the sense strand) or double-stranded. Suitable control elements such as enhancers/promoters, splice junctions, polyadenylation signals, etc. may be placed in close proximity to the coding region of the nucleic acid molecule if needed to permit proper initiation of transcription and/or correct processing of the primary RNA transcript. Alternatively, the coding region utilized in expression vectors may contain endogenous enhancers/promoters, splice junctions, intervening sequences, polyadenylation signals, etc. or a combination of both endogenous and exogenous control elements.

A nucleic acid molecule may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire nucleic acid molecule or portions of the nucleic acid molecule containing sequences found on both cDNAs; the two splice variants are therefore substantially homologous to such a probe and to each other.

In certain embodiments the nucleic acid molecule is provided in the form of expression vector or expression cassette.

In certain embodiments the nucleic acid molecule may encode a polypeptide product which is expressed episomally, for example when the nucleic acid is presented in the form of a vector, such as a plasmid. The use of a suitable extrachromosomal episomal vector within the cell nucleus provides a means of maintaining a polynucleotide sequence in target cells in high copy number extra-chromosomally, thereby eliminating potential effects of chromosomal integration. In these embodiments, the sequence which encodes the polypeptide product may be associated with a promoter which facilitates transcription of the sequence which encodes the polypeptide product. The promoter may be a constitutive promoter or an inducible promoter. Suitable promoters may include, but are not necessarily limited to a cytomegalovirus (CMV) promoter (see, for example Chen, X., Frisina, R. D., Bowers, W. J., Frisina, D. R., Federoff, H. J. (2001) HSV amplicon-mediated neurotrophin-3 expression protects murine spiral ganglion neurons from cisplatin-induced damage. *Molecular Therapy* 3 (6): 958-63 or Kawamoto, K., Sha, S. H., Minoda, R., Izumikawa, M., Kuriyama, H., Schacht, J., Raphael, Y. (2004) Antioxidant gene therapy can protect hearing and hair cells from ototoxicity. *Molecular Therapy* 9 (2): 173-181, the entire contents of which are incorporated herein by reference). The promoter may comprise a Myosin VIIa (Myo) or neuron specific enolase (NSE) promoter, as these are cell specific transcription regulators for hair cells (Myo) and spiral ganglion neurons (NSE). The promoter may comprise a cytomegalovirus immediate early (IE) enhancer (CMV-IE), or a chicken beta-actin promoter (CAG), or an elongation factor 1alpha promoter (EF-1alpha) or a Rous sarcoma virus promoter (RSV) (see, for example, Liu, Y., Okada, T., Nomoto, T., Ke, X., Kume, A., Ozawa, K., Xiao, S. (2007) Promoter effects of adeno-associated viral vector for transgene expression in the cochlea in vivo. *Exp Mol Med.* 39 (2) 170-175, the entire contents of which are incorporated herein by reference). The promoter may comprise a glial fibrillary acidic protein (GFAP) promoter. The promoter may comprise a CBA promoter, which is a hybrid promoter comprising a sequence from the chicken β-actin promoter and from the CMV promoter.

In certain embodiments the nucleic acid molecule comprises a post-transcriptional regulatory element, for example to enhance expression of the agent, such as the woodchuck hepatitis virus posttranscriptional regulatory element (WPRE) (see, for example Stone, I. M., Lurie, D. I., Kelley, M. W., Poulsen, D. J. (2005) Adeno-associated virus-mediated gene transfer to hair cells and support cells of the murine cochlea. *Mol Ther* 11(6): 843-84 and Xu, L., et al. (2001) CMV-beta-actin promoter directs higher expression from an adeno-associated viral vector in the liver than the cytomegalovirus or elongation factor 1 alpha promoter and results in therapeutic levels of human factor X in mice. *Hum. Gene Ther.* 12: 563-573, the entire contents of which are incorporated herein by reference).

In certain embodiments the Nrg-ICD enhancer and/or PSD-95 promoter is used for targeting of the expression of agent in spiral ganglion neurons (see for example Bao, J., Lin, H., Ouyang, Y., Lei, D., Osman, A., Kim, T. W., Mei, L., Dai, P., Ohlemiller, K. K., Ambron, R. T. (2004) Activity-dependent transcription regulation of PSD-95 by neuregulin-1 and Eos. *Nature Neuroscience* 7 (11): 1250-8, the entire contents of which is incorporated herein by reference).

In certain embodiments the nucleic acid molecule may be incorporated into the genome of cells within the target region.

In an embodiment, the polypeptide product which is encoded by the nucleic acid molecule may be a neurotrophic factor. In one embodiment the nucleic acid may encode a neurotrophic factor for spiral ganglion cells or cochlear hair cells. As used herein a "neurotrophic factor" is a polypeptide possessing at least one activity selected from promoting the growth and survival of developing neurons, maintaining/supporting mature neurons, and/or directing neural growth towards the source of the neurotrophic factor, and/or supporting the survival of spiral ganglion cells, and/or supporting the survival of cochlear hair cells. According to an embodiment, the neurotrophic factor is a polypeptide possessing at least one activity selected from promoting or maintaining neurite outgrowth from spiral ganglion cells and/or directing neurite outgrowth from spiral ganglion cells towards the source of the neurotrophic factor, and/or supporting the survival of spiral ganglion cells, and/or supporting the survival of cochlear hair cells. In a particular embodiment the neurotrophic factor possesses activity in promoting or maintaining neurite outgrowth from spiral ganglion cells and/or directing neurite outgrowth from spiral ganglion cells towards the source of the neurotrophic factor, and/or supporting the survival of spiral ganglion cells. The neurotrophic factor may be encoded as a preprotein, and optionally subsequently processed to a mature form. In certain embodiments, the neurotrophic factor may be selected from Neurotrophin-3 (NT-3) or Neurotrophin-3 precursor molecule or a preprotein form thereof (NCBI Accession No. HGNC:8023, Swiss Prot Accession Number P20783) or homologs or human variants thereof; Neurotrophin 4/5 (NT-4/5, NT-4, NT-5, NTF4, NTF5) or a preprotein form thereof ((HGNC:8024), Ensembl accession No. ENSP00000328738, GenBank accession No. AAA60154, version GI:190265) or homologs or human variants thereof; Nerve growth factor (NGF) (NCBI Accession No. NP_002497.2 version GI:70995319) (HGNC:7808), Ensembl accession no. ENSP00000358525), preprotein forms thereof or homologs or human variants thereof; Brain derived neurotrophic factor (BDNF, Brain-derived neurotrophic factor Precursor, Abrineurin) (the preprotein form of which is described in NCBI Accession No. NP_001137277.1 version GI:219842288, UniProtKB/Swiss-Prot Accession No P23560) or homologs or human variants thereof; glial cell line-derived neurotrophic factor (GDNF, glial cell derived neurotrophic factor precursor) (NCBI Accession No. HGNC:4232 (gene) or the preprotein forms as described in NCBI Accession Numbers NP_000505 and NP_000505.1) or homologs or human variants thereof; ciliary neurotrophic factor (CNTF) (NCBI Accession No. NP_000605 version GI:4758020 (HGNC: 2169), UniProtKB/Swiss-Prot Accession No. P26441) or homologs or human variants thereof; Activity dependent neurotrophic factor (ADNF, ADNP1; KIAA0784; ADNP, or Activity-dependent neuroprotector homeobox protein) (Ensembl Accession Numbers: ENSP00000360662, ENSP00000379346, ENSP00000342905, and ENSP00000379349) or homologs or human variants thereof, or fragments thereof, or the ADNF homologues ADNF-9 or the active peptide region with an amino acid sequence of SALLRSIPA, or ADNF-14 (neuropeptide) or the neuroprotective NAP peptide of ADNF with an amino acid sequence of NAPVSIPQ; the cytokine trophic factor leukaemia inhibitory factor (LIF) (NCBI accession No. HGNC:6596 (genomic sequence), UniProtKB/Swiss-Prot Accession No. NP_002300.1 version GI:4504991 (polypeptide), typically in conjunction with a neurotrophin such as NT-3; and Fibroblast growth factor (FGF 1, FGF 2) (NCBI accession No NM_002006 (genomic sequence), UniProtKB/Swiss-Prot Accession No. P09038 (polypeptide)) or homologs or human variants thereof, which is believed to interact with NT3 and to support neurite outgrowth and growth cone development, or in a combination of FGF-2 & GDNF; macrophage migration inhibitory factor (MIF), a cytokine the promotes inner ear sensory neuritogenesis (Bank, L M, et al. (2012), "Macrophage migration inhibitory factor acts as a neurotrophin in the developing inner ear", *Development* 139(24):4666-74), e.g. human migration inhibitory factor (MIF), Genbank accession no. M25639; neural cell adhesion molecule (CAM)—L1 provides guidance cues in the nervous system (Brümmendorf T. and Rathjen, F. G. (1996), "Structure/function relationships of axon-associated adhesion receptors of the immunoglobulin superfamily", *Curr. Opin. Neurobiol.* 6: 584-593. PMID: 8937821) and its expression in the cochlea indicates a putative role in spiral ganglion neurite guidance (Hrynko S. H. et al (1998), "Multiple roles of neural cell adhesion molecule, neural cell adhesion molecule-polysialic acid, and L1 adhesion molecule during sensory innervation of the otic epithelium in vitro", *Neuroscience* 87: 432-437), e.g. human L1CAM Genbank accession no. X59847.

The polypeptide product which is encoded may be an Apyrase (IUBMB Enzyme Nomenclature Enzyme classification EC 3.6.1.5), an enzyme which hydrolyses ATP extracellularly and therefore prevents P2X receptor activation which can inhibit neurotrophin-dependent neurite outgrowth. The polypeptide product may be an ectonucleotidase, an enzyme which promotes the production of adenosine, which is neuroprotective via adenosine receptors on spiral ganglion neurons. An example of a suitable ectonucleotidase in human subjects is ectonucleoside triphosphate diphosphohydrolase 2 (ENTPD2) (NCBI Accession no. NM 001246).

The polypeptide product which is encoded by the nucleic acid molecule may be involved in the melanocortin signalling pathway, for example alpha-melanocyte stimulating hormone (alpha-MSH). The melanocortins make up a family of endogenous peptides derived from pro-opiomelanocortin, which bind to five melanocortin receptors (MCRs). Other examples of melanocortins which may be encoded by the nucleic acid molecule include proopiomelanocortin (POMC) or its cleavage products (adrenocorticotropin/beta-lipotropin/alpha-melanocyte stimulating hormone/beta-melanocyte stimulating hormone/beta-endorphin) or precursors of active peptides (for gene NCBI Accession No. HGNC: 9201; for precursor NCBI accession No AAA60140 version GI:190188).

The polypeptide product which is encoded by the nucleic acid molecule may be a morphogen, for example a bone morphogenic protein (BMP), Sonic hedgehog, or Wingless/Wnts.

The polypeptide product which is encoded by the nucleic acid molecule may be an axon guidance factor which is capable of attracting neurites, such as spiral ganglion cell neurites, such as laminin, Netrin-1, an Ephrin, a semaphorin, a Slit such as a 3 slit homolog, slit2 or slit3 or a cytokine such as Leukemia inhibitory factor.

(b) Nucleic Acid Molecules which Modulate Endogenous Gene Expression

In certain embodiments the agent may comprise or consist of a nucleic acid molecule which modulates the expression of an endogenous gene sequence. Depending on the particular application, the modulation of expression may up-regulate or down-regulate expression of the gene. The modulation of expression of the endogenous gene may be a direct regulation of expression, for example by directly modulating transcription or translation of an endogenous gene. The modulation of expression of the endogenous gene by the nucleic acid molecule may be an indirect regulation of expression, for example by expression of a polypeptide by the nucleic acid molecule which in turn modulates the expression of the endogenous gene. An example may be targeted inhibition of adenosine kinase (NCBI accession No HGNC:257 (genomic sequence); NP_001114.2 (polypeptide)), leading to increased extracellular adenosine levels which are neuroprotective.

The modulation of expression of an endogenous gene sequence may be an up-regulation of an endogenous gene sequence. For example, the nucleic acid molecule may encode a transcription factor which promotes the expression of an endogenous gene, such as a gene which encodes a neurotrophic factor. The Sox2, Brn-3.1 and Gata 3 transcription factors are examples of this class of cell signalling molecule associated with determination of sensory hair cell, supporting cell and spiral ganglion neuron development and survival in the cochlea (Keithley, E M, Erkman, L., Bennett, T., Lou, L. Ryan, A. F. (1999) Effects of a hair cell transcription factor Brn-3.1, gene deletion on homozygous and heterozygous mouse cochleae in adulthood and aging. *Hearing Research* 134:71-76; Van der Wees, J., Van Looij, M. A., de Ruiter, M M, Elias, H., van der Burg, H., Liem, S. S., Kurek, D., Engle, J. D., Karis, A., van Zanten, B. G., de Zeeuw, C. I., Grosveld, F. G., van Doornick, J. H. (2004) Hearing loss following Gata3 haploinsufficiency is caused by cochlear disorder. *Neurobiol Dis* 16:169-78; Dabdoub, A., Puligilla, C., Jones, J. M., Fritzsch, B., Cheah, K. S., Pevney, L. H. Kelley, M. W. (2008) Sox2 signalling in prosensory domain specification and subsequent hair cell differentiation in the developing cochlea. *Proc Natl Acad Sci USA* 105:18396-401; and Appler, J., Koundakjian, E., Lu, C, Goodrich, L. (2009) Gata3 regulates neurite extension and targeting of spiral ganglion neurons. *Proc, 7th Molecular Biology of Hearing and Deafness conference*. June 20-23, Harvard Medical School, Boston, Mass., USA).

The Adenovirus-mediated transduction of the transcription factor atonal homologue 1 (Atoh1, also known as Math1, ATH1, HATH1 or bHLHa14) (NCBI accession No. BC069578 version GI:47480322 (HGNC:797), Uniprot accession Nos. Q92858; Q14CT9) into mouse or guinea pig cochlear cells has been described to lead to the generation of a cochlear hair cell-like phenotype from supporting cells, which led to secretion of trophic factors, the attraction of neurite outgrowth and the formation of functional synapses between the transformed cells and auditory spiral ganglion cells. Accordingly, the methods described herein contemplate the transfection of the transcription factor atonal homologue 1 into cochlear cells using electroporation, without the need for viral vector-mediated delivery.

Other transcription factors which modulate the expression of neurotrophic factors in cells are known in the art. For example, the transcription factor SRY-box-containing gene 10 (Sox10) induces a greater than 100 fold up regulation of the expression of ciliary neurotrophic factor in Schwann cells in the mouse, whilst knockdown of Sox10 results in a reduction of expression ciliary neurotrophic factor by more than 80%. Accordingly, the methods described herein contemplate the transfection of cells within a target region in a subject by electroporation of a nucleic acid molecule encoding a transcription factor, wherein the transcription factor modulates the expression of an endogenous neurotrophic factor, or wherein the transcription factor modulates the expression of an exogenous polynucleotide sequence which encodes a neurotrophic factor and which is transfected with the transcription factor.

The up-regulation of a gene sequence may be achieved by the use of gene targeting constructs to generate transcription units formed by homologous recombination between an endogenous target gene and the targeting construct. In such methods, expression of a desired targeted gene in a cell (i.e., a desired endogenous cellular gene) is altered by the introduction by homologous recombination into the cellular genome at a preselected site, of DNA which includes at least a regulatory sequence, an exon and a splice donor site. These components are introduced into the chromosomal (genomic) DNA in such a manner that this, in effect, results in production of a new transcription unit (in which the regulatory sequence, the exon and the splice donor site present in the DNA construct are operatively linked to the endogenous gene). As a result of introduction of these components into the chromosomal DNA, the expression of the desired endogenous gene is altered.

The production and use of targeting constructs are described, for example, in U.S. Pat. No. 5,641,670 (Treco et al.), the entire contents of which are incorporated herein by reference. Endogenous genes which may be up-regulated by these techniques include neurotrophic factor genes selected from Neurotrophin-3 (NT-3) or Neurotrophin-3 precursor molecule or a preprotein form thereof (NCBI Accession No. HGNC:8023, Swiss Prot Accession Number P20783) or homologs or human variants thereof; Neurotrophin 4/5 (NT-4/5, NT-4, NT-5, NTF4, NTF5) or a preprotein form thereof ((HGNC:8024), Ensembl accession No. ENSP00000328738, GenBank accession No. AAA60154, version GI:190265) or homologs or human variants thereof; Nerve growth factor (NGF) (NCBI Accession No. NP_002497.2 version GI:70995319) (HGNC:7808), Ensembl accession no. ENSP00000358525), preprotein forms thereof or homologs or human variants thereof; Brain derived neurotrophic factor (BDNF, Brain-derived neurotrophic factor Precursor, Abrineurin) (the preprotein form of which is described in NCBI Accession No. NP_001137277.1 version GI:219842288, UniProtKB/Swiss-Prot Accession No P23560) or homologs or human variants thereof; glial cell line-derived neurotrophic factor (GDNF, glial cell derived neurotrophic factor precursor) (NCBI Accession No. HGNC:4232 (gene) or the preprotein forms as described in NCBI Accession Numbers NP_000505 and NP_000505.1) or homologs or human variants thereof; ciliary neurotrophic factor (CNTF) (NCBI Accession No. NP_000605 version GI:4758020 (HGNC: 2169), UniProtKB/Swiss-Prot Accession No. P26441) or homologs or human variants thereof; Activity dependent neurotrophic factor (ADNF, ADNP1; KIAA0784; ADNP, or Activity-dependent neuroprotector homeobox protein) (Ensembl Accession Numbers: ENSP00000360662, ENSP00000379346, ENSP00000342905, and ENSP00000379349) or homologs or human variants thereof, or fragments thereof, or the ADNF homologues ADNF-9 or the active peptide region with an amino acid sequence of SALLRSIPA, or ADNF-14 (neuropeptide) or the neuroprotective NAP peptide of ADNF with an amino acid sequence of NAPVSIPQ, the cytokine trophic factor leukaemia inhibitory factor (LIF) (NCBI accession No. HGNC:6596 (genomic sequence), UniProtKB/Swiss-Prot Accession No. NP_002300.1 version GI:4504991 (polypeptide), typically in conjunction with a neurotrophin such as NT-3; and Fibroblast growth factor (FGF 1, FGF 2) (NCBI accession No NM_002006 (genomic sequence), UniProtKB/Swiss-Prot Accession No. P09038 (polypeptide)) or homologs or human variants thereof, which is believed to interact with NT3 and to support neurite outgrowth and growth cone development, or in a combination of FGF-2 & GDNF; Apyrase; or ectonucleoside triphosphate diphosphohydrolase 2 (ENTPD2) (NCBI Accession no. NM 001246); a gene encoding a polypeptide involved in the melanocortin signalling pathway, for example alpha-melanocyte stimulating hormone (alpha-MSH), proopiomelanocortin (POMC) (HGNC Accession No. HGNC:9201), or a gene encoding a morphogen, for example a bone morphogenetic protein (BMP), Sonic hedgehog, or Wingless/Wnts, a gene encoding an axon guidance factor, such as laminin, Netrin-1, an Ephrin, a semaphorin, a Slit such as a 3 slit homolog, slit2 or slit3 or a cytokine such as Leukaemia inhibitory factor; a gene encoding macrophage migration inhibitory factor (MIF), a cytokine the promotes inner ear sensory neuritogenesis (Bank, L M, et al. (2012), "Macrophage migration inhibitory factor acts as a neurotrophin in the developing inner ear", *Development* 139(24):4666-74), e.g. human migration inhibitory factor (MIF), Genbank accession no. M25639; a gene encoding macrophage migration inhibitory factor (MIF), a cytokine the promotes inner ear sensory neural cell adhesion molecule (CAM)—L1 provides guidance cues in the nervous system (Brümmendorf T. and Rathjen, F. G. (1996), "Structure/function relationships of axon-associated adhesion receptors of the immunoglobulin superfamily", *Curr. Opin. Neurobiol.* 6: 584-593. PMID: 8937821; Hrynko S. H. et al (1998), "Multiple roles of neural cell adhesion molecule, neural cell adhesion molecule-polysialic acid, and L1 adhesion molecule during sensory innervation of the otic epithelium in vitro", *Neuroscience* 87: 432-437), e.g. human L1CAM Genbank accession no. X59847.

The modulation of expression of the endogenous gene may be the down-regulation of expression of an endogenous gene. The down-regulation of expression of the endogenous gene may, for example, be the down-regulation of a transcription factor which constitutively or inducibly inhibits the expression of a neurotrophic factor by a cell within a target region in a subject, such as a cochlear mesenchymal cell, which results in the cell expressing a neurotrophic factor.

The down-regulation of an endogenous gene may utilize the targeted disruption of the expression of one or more endogenous genes using any nucleic acid molecules which selectively target and inhibit the expression of the genes, such as antisense sequences, varieties of small interfering RNA (siRNA) sequences, shRNA sequences, microRNAs, ribozyme sequences, and the like. The "expression" of endogenous genes is intended to encompass the transcription and/or translation of endogenous gene sequences.

Methods for the design, synthesis, and delivery of antisense nucleic acid molecules are well known in the art. The antisense molecules may be DNA or RNA, or partial or complete synthetic analogues thereof. Sequences of/for antisense constructs may be derived from various regions of the target gene(s). Antisense constructs may also be designed to target and bind to regulatory regions of the nucleotide sequence, such as the promoter, or to coding (exon) or non-coding (intron) sequences. Antisense polynucleotides of the invention may be generated which are at least substantially complementary along their length to the region of the gene in question. Binding of an antisense polynucleotide to its complementary cellular sequence may interfere with transcription, RNA processing, transport, translation and/or mRNA stability.

Suitable antisense oligonucleotides may be prepared by methods well known to those of skill in the art. Typically antisense oligonucleotides will be synthesized on automated synthesizers. Suitable antisense oligonucleotides may include modifications designed to improve their delivery into cells, their stability once inside a cell, and/or their binding to the appropriate target. For example, the antisense oligonucleotide may be modified by the addition of one or more phosphorothioate linkages, or the inclusion of one or more morpholine rings into the backbone. The antisense oligonucleotide may be 10-30 base pairs in length.

As a practical matter, the level of complementarity between the antisense nucleic acid molecule and the target mRNA or cDNA sequence, or portion thereof, can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman to find the best segment of homology between two sequences (Advances in Applied Mathematics 2:482-489 (1981)). When using Bestfit or any other sequence alignment program to determine whether a particular sequence is, for instance, 90% identical to a reference sequence, the parameters are set such that the percentage of identity is calculated over the full length of the reference nucleotide sequence and that gaps in homology of up to 5% of the total number of nucleotides in the reference sequence are allowed. A preferred method for determining the best overall match between a query sequence and a subject sequence, also referred to as a global sequence alignment, can be determined using the FASTDB computer program based on the algorithm of Brutlag and colleagues (Comp. App. Biosci. 6:237-245 (1990)). In a sequence alignment the query and subject sequences are both DNA sequences. An RNA sequence can be compared by converting U's to Ts. The result of said global sequence alignment is in percent identity. Preferred parameters used in a FASTDB alignment of DNA sequences to calculate percent identity are: Matrix=Unitary, k=tuple=4, Mismatch Penalty=1, Joining Penalty=30, Randomization Group Length=0, Cut-off Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. Only bases outside the 5' and 3' bases of the subject sequence, as displayed by the FASTDB alignment, which are not matched/aligned with the query sequence, are calculated for the purposes of manually adjusting the percent identity score.

Small interfering RNA (siRNA) sequences are small, usually double-stranded RNA oligonucleotides, for example at 19, 21, 27 or 29 bases in length, with or without overhangs, which specifically hybridize with RNA sequences of interest and which serve as substrates for the RNA-induced silencing complex. Double-stranded RNA molecules may be synthesized in which one strand is identical to a specific region of the mRNA transcript to be silenced, and this double stranded RNA may be introduced directly. Alternatively, corresponding dsDNA can be employed, which, once presented intracellularly is converted into dsRNA. Methods for the design and synthesis of suitable siRNA molecules for use in RNA interference (RNAi) and for achieving post-transcriptional gene silencing are well known to those of skill in the art. For example, rules for the rational design of siRNA are available online in "Rules of siRNA design for RNA interference (RNAi)" from the Protocol Online web page. These rational design principals are also described in Elbashir S M et al. (2001), "'Duplexes of 21-nucleotide RNAs mediate RNA interference in cultured mammalian cells", Nature, 411:494-498; Elbashir S M et al. (2001). Functional anatomy of siRNAs for mediating efficient RNAi in *Drosophila melanogaster* embryo lysate. EMBO J. 20:6877-6888; Elbasbir S M et al. (2002), "Analysis of gene function in somatic mammalian cells using small interfering RNAs", Methods, 26:199-213; Reynolds A, Leake D, Boese Q, Scaringe S, Marshall W S, Khvorova A (2004), "Rational siRNA design for RNA interference", Nat Biotechnol. (2004) 22(3):326-30; and online at Oligonucleotide Properties Calculator (oligocalc). The entire contents of each of these publications is incorporated herein by reference.

Examples of two siRNA design tools which implement the rational siRNA principals discussed above are design algorithms offered by Dharmacon, Inc and also available in a downloadable Microsoft Exel™ template, written by Maurice Ho.

The skilled addressee will appreciate that a range of suitable siRNA or nucleic acid molecules comprising an siRNA sequence which is capable of inhibiting the expression of an endogenous gene can be identified and generated based on knowledge of the sequence of the genes in question using routine procedures known to those skilled in the art without undue experimentation. Those skilled in the art will appreciate that there need not necessarily be 100% nucleotide sequence match between the target sequence and the siRNA sequence. The capacity for mismatch is dependent largely on the location of the mismatch within the sequences. In some instances, mismatches of 2 or 3 nucleotides may be acceptable but in other instances a single nucleotide mismatch is enough to negate the effectiveness of the siRNA. The suitability of a particular siRNA molecule may be determined using routine procedures known to those skilled in the art without undue experimentation.

Although the maximal effects of antisense nucleic acids and siRNA on the specific inhibition of RNA or protein expression are comparable, siRNA generally produces a longer-lasting effect.

Ribozymes, such as hammerhead or hairpin ribozymes, are capable of the targeted catalytic cleavage and splicing of specific RNA sequences, including mRNA and genomic RNA sequences. The design and methods for the delivery of ribozymes are reviewed, for example, in Vaish, Kore and Eckstein (1998) *Nucleic Acids Research* 26:5237-5242; in Lieber and Strauss (1995) *Mol. Cell. Biol.* 15:540-551; and in Usman and Blatt (2000) *J Clin Invest* 106:1197-1202, the entire contents of each of which are incorporated herein by reference.

Short hairpin RNA (shRNA) is a sequence of RNA with a tight hairpin turn structure which is introduced into cells as part of a vector which comprises a constitutive promoter such as a U6 promoter to allow shRNA to be constitutively expressed. The shRNA hairpin structure is cleaved by the cellular machinery into siRNA, which is then bound to the RNA-induced silencing complex (RISC). This complex binds to and cleaves mRNAs which match the siRNA that is bound to it. The vector comprising the shRNA sequence is usually passed on to daughter cells in cell division, allowing the gene silencing to be inherited. Strategies for designing shRNA sequences and nucleic acid molecules comprising shRNA for use in mammalian cells are known, for example McIntyre and Fanning, Design and cloning strategies for constructing shRNA expression vectors, *BMC Biotechnol.* (2006) 6:1.

The nucleic acid may be microRNA. The term microRNA or "miRNA" as used herein has the ordinary and plain meaning of a non-coding RNA molecule found in eukaryotes which is involved in RNA-based gene regulation. The term can be used to refer to the single-stranded RNA molecule processed from a precursor or in certain instances the precursor itself or a mimetic or inhibitor thereof. MicroRNAs are capable of control of expression of genes in humans and non-human animals, and play a significant role in control of development regulatory mechanisms (see, for example, John B, et al. (2004), "Human MicroRNA Targets", *PLoS Biol* 2(11): e363. doi:10.1371/journal.pbio.0020363; and Li et al (2010), "Computational approaches for microRNA studies: a review", *Mamm Genom.* 21(1-2):1-12). The involvement of microRNA in normal cochlear function and in a familial cochlear disorder has also been described in Mencia et al., *Nature Genetics* (2009) 41(5):609-613. It is anticipated that the modulation of microRNA activity in cells of the cochlea, either by the introduction of microRNA or microRNA mimics into cells or the silencing of endogenous microRNA with a microRNA inhibitor/decoy (see, for example, Mullokandov et al (2012), "High-throughput assessment of microRNA activity and function using microRNA sensor and decoy libraries", *Nat. Methods* 9(8): 840-846) may provide an approach for modulating the expression of particular targeted genes. Strategies for the administration of microRNA into cells or tissues of subjects have been described in International patent publication No. WO 2008/073920, which describes methods of modulating gene expression, or biologic or physiologic pathways in a cell, a tissue, or a subject comprising administering to the cell, tissue, or subject an amount of an isolated nucleic acid or mimetic thereof comprising a specific microRNA or microRNA inhibitor nucleic acid sequence in an amount sufficient to modulate the expression of a gene positively or negatively modulated by the microRNA. Studies have demonstrated therapeutic application of modulating microRNA in animals, including primates.

Techniques for the design of microRNA and microRNA inhibitors are readily available. A database of known microRNA sequences, new microRNA sequences and predicted microRNA targets is maintained at miRBase (available via an internet search for miRbase or microRNA database) and described in "miRBase: tools for microRNA genomics" Griffiths-Jones S, Saini HK, van Dongen S, Enright AJ. NAR 2008 36(Database Issue):D154-D158; "miRBase: microRNA sequences, targets and gene nomenclature" Griffiths-Jones S, Grocock R J, van Dongen S, Bateman A, Enright AJ. NAR 2006 34(Database Issue): D140-DI44; and "The microRNA Registry." Griffiths-Jones S. NAR 2004 32(Database Issue):D109-D11L. Commercial services are available for the design and synthesis of specific microRNA inhibitors based on a provided target sequence.

Alternatively, avoidance of microRNA suppression of a target gene may be achieved by introducing into cells in a target region in a subject, as described above, an exogenous homologous sequence sufficiently different to the endogenous target sequence such that the microRNA is insufficiently homologous to the introduced sequence to achieve suppression.

Expression of genes within target regions may also be regulated by introduction of mutations.

Mutations may be inserted into target genes by any method as known in the art.

For example, an exogenous nucleic acid may be introduced which comprises an oligonucleotide or polynucleotide which introduces a mutation comprising single or multiple nucleotide insertions, deletions or substitutions into the endogenous target gene.

Single or multiple nucleotide insertions, deletions or substitutions may be introduced via recombination of the target mutation site with an introduced targeting nucleotide sequence. Such an introduced nucleotide sequence may, for example, comprise a nucleotide sequence to be introduced into the genome flanked either side by nucleotide sequences homologous to target sequences contiguous in or located either side of a desired mutation insertion point. In accordance with the methods of the present invention, a nucleotide sequence to be introduced into the genome may also include a selectable marker operably linked to desired regulatory regions (which may include, for example, a stress-inducible promoter).

The nucleotide sequences homologous to the target sequences may be isogenic with the target sequences to thereby promote the frequency of homologous recombination.

Homologous nucleotide sequences that are not strictly isogenic to the target sequences can also be used. Although mismatches between the homologous nucleotide sequences and the target sequences can adversely affect the frequency of homologous recombination, isogenicity is not strictly required and substantial homology may be sufficient. For the purposes of the present invention, the level of homology between the homologous sequences and the target sequences may be at least about 90% identity, at least about 95% identity, at least about 99% identity or 100% identity.

A targeting nucleotide sequence can be comprised in a vector. Representative vectors include plasmids, cosmids, and viral vectors. Vectors can also comprise nucleic acids including expression control elements, such as transcription/translation control signals, origins of replication, polyadenylation signals, internal ribosome entry sites, promoters, enhancers, etc., wherein the control elements are operatively associated with a nucleic acid encoding a gene product. Selection of these and other common vector elements are conventional and many such sequences can be derived from commercially available vectors. See, for example, Sambrook, J. et al., Molecular Cloning, Cold Spring Harbor Laboratory (1989), Sambrook, J. and Russell, D. W. (2001), *"Molecular Cloning: A Laboratory Manual"*, 3rd edition, (*Cold Spring Harbor Laboratory Press*, and references cited therein and Ausubel et al. (eds) Current Protocols in Molecular Biology, John Wiley & Sons (2000).

Optionally, a targeting DNA is co-administered with a recombinase, for example recA, to a target cell to thereby enhance the rate of homologous recombination. The target cell(s) may already comprise, or have been transformed to comprise suitable recombinase target sequences, if required.

For example, a recombinase protein(s) can be loaded onto a targeting DNA as described in U.S. Pat. No. 6,255,113. To enhance the loading process, a targeting DNA can contain one or more recombinogenic nucleation sequences. A targeting DNA can also be coated with a recombinase protein by pre-incubating the targeting polynucleotide with a recombinase, whereby the recombinase is non-covalently bound to the polynucleotide. See, for example, A. Vergunst et al (1998), *Nucleic Acids Res.* 26:2729 and A. Vergunst and P. Hooykaas (1998), *Plant Molec. Biol.* 38:393 406, International patent publications WO 99/25821, WO 99/25840, WO 99/25855, and WO 99/25854 and U.S. Pat. Nos. 5,780, 296, 6,255,113, and 6,686,515.

Mutations may also be introduced into plants using zinc finger nucleases (ZFNs), transcription activator-like effector nucleases (TALENs), clustered regulatory interspaced short palindromic repeat (CRISPR)/Cas-based RNA-guided DNA endonucleases, and homing endonucleases (HEs) as discussed in, for example, Gaj T. et al (2013; *Trends Biotechnol.* 31(7): 397-405), Carroll D. (2012; *Molecular therapy* 20(9): 1659-1660), Xiao A. et al (6 Jun. 2013; *Nucleic Acids Research* 2013, 1-11, doi: 10.1093/nar/gkt464, P. Mali, K. M. Esvelt, G. M. Church (2013), *Nat. Methods* 10, 957-963 (2013). doi: 10.1038/nmeth.2649; pmid: 24076990, and P. Mali et al., (2013), *Science* 339, 823-826 (2013).doi: 10.1126/science.1232033; pmid: 23287722, the disclosures of these references being hereby incorporated by cross-reference.

Agents Other than Nucleic Acid Molecules

Also contemplated in the methods described herein is the electroporation of polypeptides, such as small neuroprotective polypeptides which may support the survival of cochlear hair cells and/or spiral ganglion cells. Examples of such molecules include the neuroprotective NAP peptide, activity dependent neurotrophic factor, FNK peptide, $ACTH_{4-9}$ analogue Org 2766, or molecules comprising these peptides which retain neuroprotective activity in the cochlea.

Delivery of Agents

Agents for electroporation into one or more cells within a target region in a subject may be delivered to the target region by any suitable method as known in the art. Non-limiting examples may include injection or microinjection or coating of the agent directly on the microarray.

In one embodiment, one or more of the electroporation electrodes, or the electroporation assembly comprising the electrode(s) or electrode array(s) may comprise a lumen, channel or groove which carries the agent and allows the delivery of the agent to the target region, or it may be associated with a separate catheter or cannula, such as a silicon or polymer tube which is attached to the electrode. Alternatively, the agent may be introduced into the target region via a cannula which may be inserted or removed independently to the electroporation electrode.

In embodiments in which a cochlear implant provides at least one electroporation electrode, the agent may be provided via a lumen, channel or groove in the cochlear implant electrode microarray. These forms of electrode may allow multiple rounds of introduction of agent into the cochlea following implantation of the cochlear implant and therefor multiple rounds of electroporation. The use of a cochlear implant with a lumen to deliver agents to the cochlea is described, for example, in Paasche et al., (2003) *Otology & Neurology* 24:222-227, the entire contents of which is incorporated herein by reference.

The lumen of the cochlear implant may be sealed following delivery of the agent.

US patent application publication No. 2008/0214986, the entire content of which is incorporated herein by reference, describes the use of gel compositions with a predetermined conductivity for use in optimising the electroporation of tissues. In certain embodiments, the electrodes and or cochlear implant may be coated with gel, as described in US 2008/0214986, to provide a degree of control over the conductivity of the volume surrounding the electrodes.

In certain embodiments of the methods described herein wherein the cochlear implant comprises at least one electrode which is used for electroporation, the agent is delivered to the target region using a catheter or cannula which is not associated with the cochlear implant. In these embodiments typically the catheter or cannula is inserted into the target region and the solution comprising the agent is delivered. The catheter or cannula is then withdrawn, the cochlear implant is introduced and electroporation takes place, as described above.

The agent may be delivered to the target region at the time the electroporation electrode(s) is/are inserted into the target region, or before the insertion of the electroporation electrode or after the insertion of the electroporation electrode. The agent may be provided in a diffusible form, such as incorporated in or associated with a biodegradable or biocompatible viscous liquid or gel solution surrounding the electrode array of the cochlear implant. The viscous liquid or gel solution may comprise polyacrylic acid (PAA), polyvinyl alcohol (PVA), polylactic acid (PLA) and/or polyglycolic acid (PGA). Pluronic F127 (BASF) at <30% solution may also be used to stabilise the media containing the agent. This approach may provide an advantage in that the agent is presented to the target region with the electrode(s) in situ in a stable concentration of at the time of electroporation.

Where the agent comprises a nucleic acid molecule the agent may be presented in a diluent solution which comprises ions and proteins, or the agent may be diluted in sterile distilled deionised water, provided that the diluent solution does not substantially adversely affect the efficiency of electroporation or efficacy of the agent. Typically water is used as the diluent, or with a generic buffer such as TRIS (50 mM), or isotonic saline, with the nucleic acid molecule provided typically at a concentration of from 10 ng/µl to 10 µg/µl. The nucleic acid molecule may be provided within a buffered solution, such as phosphate-buffered saline (PBS; e.g. pH 7.4), or a perilymph-like solution (for example as described by Salt, A. N. Konishi, T. (1986) The cochlear fluids: Perilymph and endolymph. Eds. Altschuler, R. A., Hoffman, D. W., Bobbin, R. P. In: *Neurobiology, of Hearing: The Cochlea*. New York, Raven Press, pp. 109-122), and may be in the presence of divalent cation chelators such as ethylenediaminetetraacetic acid (EDTA) for stabilization of the molecules.

Where the target region is located in a cochlea, the target region may be in the cochlear chamber, such as a region comprising mesenchymal cells of the scala tympani, of the scala vestibuli or of the scala media. In such an embodiment, typically the solution comprising agent is delivered to the base of the cochlea, typically via a perforated round window, so that the solution comprising the agent flows through the cochlear perilymphatic chambers and displaces the media lying within the cochlea chamber. Alternatively the solution comprising the agent may be delivered via a cochleostomy. The volume of the human scala tympani is in the order of 30 µl, the scala vestibuli 22 µl, and the scala media 2 µl. In order to ensure that the chamber contains sufficient agent the nominal volume of solution comprising the agent to be delivered to the cochlea may be in the order of 60 µl or less.

Typically, the controlled delivery of such a volume may be achieved through the use of a mechanical infusion micropump, or a microsyringe. Once the agent and electrode are present within the appropriate chamber(s) electroporation takes place, and in certain embodiments the electroporation electrode is then removed. In these embodiments of the invention the electroporation electrode may be withdrawn from the cochlea as a separate action to the placement of the cochlear implant, and typically the electrode is removed before the insertion of the cochlear implant.

Preferred forms of the present invention will now be described, by way of example only, with reference to the following examples, including comparative data, and which are not to be taken to be limiting to the scope or spirit of the invention in any way.

EXAMPLES

Example 1

Materials and Methods

Vector Preparation

The brain derived neurotrophic factor (BDNF) gene therapy cassette (CMVp-3xflag-BDNF-IRES-hrGFP gene cassette) comprised a CMV (cytomegalovirus) promoter upstream of a C-terminal FLAG-tagged proBDNF gene (including signal peptide), with GFP co-expression afforded by an internal ribosome entry site (IRES) (see FIG. 1a). Plasmid DNA was purified from E. coli cultures using a PureLink MaxiPrep kit (Invitrogen). DNA was resuspended in tris-buffered saline at 2 µg/µL and stored at −20° C. DNA was quantified on a NanoDrop ND-1000 spectrophotometer (Thermo Scientific) and confirmed by gel electrophoresis. 20 µL of the DNA suspension was used to transfect each cochlea via microinjection into scala tympani of the cochlea via the round window, followed by cochlear implant array-based electroporation.

Animal Use

Coloured guinea pigs of either sex weighing between 500 g and 700 g were used for the procedures. Procedures were approved by the University of New South Wales Animal Care and Ethics Committee. Anaesthesia was induced using 4% isoflurane delivered with oxygen, and maintained at 1-2% isoflurane. Buprenorphine (15 µg/kg i.m., Temgesic, Reckitt Benckiser), and medetomidine hydrochloride (175 µg/kg i.m., Domitor, Pfizer Animal Health) were used for analgesia and enrofloxacin (5 mg/kg i.m., Baytril, Bayer Australia Ltd) was used as a prophylactic antibiotic. Body temperature control and cardio-pulmonary monitoring ($O_2$ saturation and heart rate) were sustained (MouseStat, Kent Scientific). Guinea pigs were euthanized via intraperitoneal injection of pentobarbital (100 mg/kg of body weight) at the conclusion of experiments, or to provide cochlear tissue for ex vivo close-field electroporation.

Microarray-Based Close-Field Electroporation Ex Vivo and Organotypic Culture

Both cochleae were removed immediately after euthanasia and placed into DMEM media (GIBCO) at room temperature. Under a dissection microscope a perforation was made through the round window using a 29 gauge needle and cochleae were placed onto sterile cloth dampened with Tris buffered saline (TBS). 20 µL of plasmid DNA was injected into scala tympani via the round window and the cochlear implant electrode array (part no. Z60271, Cochlear Ltd, Australia) was then inserted into the basal turn (FIG. 1 c, d). Electroporation of the mesenchymal cells lining the scalae was achieved using between 5 and 50 pulses (50 ms; 950 ms interval) at varying voltages (CUY 21 square wave electroporator; NEPA GENE) in either a 'tandem' or 'alternating' electrode array configuration (FIG. 1d). The resistance of the tandem and alternating array configurations ranged between 150 and 1200 ohms. After a 10 minute interval, the array was removed and the cochlea was incubated at room temperature for a further 20 minutes in the humidity chamber, before resection to enable organotypic culture. Dissected elements of the cochlea were placed into supplemented DMEM media (GIBCO), (10% fetal bovine serum and 100 units/mL streptomycin and penicillin), and incubated at 37° C. with 5% $CO_2$ for three to four days. Tissue was then fixed in 4% paraformaldahyde (PFA) for 30 minutes, then transferred to 0.1M phosphate buffered saline (PBS). The number and location of GFP expressing cells on each fragment of the cochlea was recorded using epifluorescence microscopy. Immuno-labelling was performed as described below on some cochleae to confirm expression of the FLAG-tagged BDNF neurotrophin gene construct (FIG. 7d; FIG. 9d).

In Vivo Close-Field Electroporation Gene Delivery

In vivo electroporation of the BDNF gene construct was achieved using the electrode array inserted into scala tympani via the round window under anaesthesia. The surgical approach utilised a post-auricular exposure of the mastoid process. A hole was drilled through the bulla allowing visualisation of the round window. A small perforation was made in the round window using a 29 gauge needle. 20 µL of DNA solution was loaded into 0.96 mm outside diameter, 0.58 mm internal diameter PVC tubing, connected to a microperfusion pump. Fine forceps were used to match the end of the tubing to the face of the round window and the DNA was delivered into the cochlea. The electrode array was then inserted into scala tympani and close-field electroporation carried out as described for the in vitro experiments. Ten minutes after electroporation the array was removed and the wound sutured and the animals supported during recovery. Analysis of mesenchymal cell transfection, recombinant BDNF production and neural regeneration was undertaken up to three weeks post-surgery by euthanizing the guinea pigs and perfusing the dissected cochlea with PFA as described above.

BDNF Gene Therapy in a Deafened Guinea Pig Model

To study spiral ganglion regeneration with CFE-mediated neurotrophin gene therapy, guinea pigs were deafened using an ototoxic treatment targeting the sensory hair cells through co-administration of furosemide (100 mg/kg i.v. via external jugular cannulation; Troy Laboratories), and i.m. injection of kanamycin sulphate (400 mg/kg; Sigma), as previously described (Nelson, D. I., et al (2005), "The global burden of occupational noise-induced hearing loss", *Am J Ind Med* 48, 446-458). Deafness was confirmed using auditory brainstem response (ABR) and distortion product otoacoustic emission (DPOAE) measurement via a TDT systems II evoked potential workstation, including a Medusa optically-coupled headstage (Tucker-Davis Technologies) within a sound attenuating chamber (Sonora Technology) (after Holt, J. R. and Vandenberghe, L. H. (2012), "Gene therapy for deaf mice goes viral", *Mol Ther* 20, 1836-1837). Testing was performed prior to deafening and again one to two weeks post treatment. ABR was determined at 2, 4, 8, 16, 24 and 32 kHz tone pips (5 ms) and clicks (100 µs, alternating polarity), while DPOAE was tested at 6, 8, 16, 20, 24 and 28 kHz. ABR thresholds were tested to a maximum level of 90 dB SPL while DPOAE was evaluated 60 dB SPL. Only animals lacking ABR or DPOAE were used in the gene therapy experiments.

Tissue Processing Following In Vivo Electroporation

Fixed cochleae were decalcified in 8% EDTA in 0.1M sodium phosphate buffer at 4° C. for two weeks (EDTA solution was changed every 2-3 days). To determine transformed cell counts of in vivo electroporation-alone animals, decalcified cochleae were cut with a scalpel along the modiolar axis, removing the topside of the bony capsule of the cochlea. GFP positive cells on each hemisection could then be located and counted with an epifluorescence microscope.

To analyse neurite maintenance and outgrowth, decalcified cochleae of deafened and treated guinea pigs were cryoprotected in 10% sucrose for 24 h and 30% sucrose for 24 h. Cochleae were embedded using Tissue-Tek OCT (Sakura Finetek), snap frozen at −80° C. and cryosectioned at 50 µm. Mid-modiolar sections were placed into 12 well plates containing 0.1M PBS for immunolabeling. Cochleae of one guinea pig, also deafened and treated were not cryosectioned. These cochleae were hemisectioned as was done for the electroporation-alone animals and immunostaining was performed in situ on whole-mount tissue to provide a three dimensional view of the neurite outgrowth (FIG. 14 a, b).

Immunohistochemistry

Tissue was immunolabeled in 12 well plates containing 0.1 M PBS. 10% normal goat serum (NGS) was included as a blocking agent along with 1% Triton X-100 for permeabilization. The tissue was incubated at room temperature for one hour prior to addition of the primary antibody (with 5% NGS and 0.1% Triton X-100). Primary incubation used a 1:8000 dilution of anti-neuronal class III β-Tubulin (TUJ1) (Covance) or 1:500 anti-FLAG (F7425) (Sigma) or 1:400 anti-aspartoacylase (ASPA) antibody. Secondary antibodies used were Alexa-488 conjugated goat anti-mouse (A11001) (Invitrogen) for class III β-Tubulin, and Alexa-594 conjugated goat anti-rabbit (A11072) (Invitrogen) for FLAG and ASPA primaries. Both primary and secondary staining was done overnight at 4° C. in PBS containing 5% goat serum and 0.01% Triton X-100. Three washes of 10, 20 and 40 minutes were done after incubation with each antibody.

Image Acquisition and Statistical Analysis

Semi-quantitative analysis of spiral ganglion neurite regeneration and increase in SGN somata cell size was performed using f-tubulin immunofluorescence data. Images were acquired using a confocal laser scanning microscope (Zeiss LSM 710 NLO). Three mid-modiolar sections were imaged for each cochlea and three optical slices were captured and exported as separate TIFF files for each section. The optical slices were taken at 10 µm intervals through the centre of each section. Exported 8 bit TIFF files were analysed using Image J software (National Institutes of Health). Images were taken of the basal turn only for both left (treated) and right (control) cochleae. The mean values obtained for the three optical slices were averaged over the three tissue sections to generate a mean value for each cochlea. To calculate the average soma size, the circumference of each SGN cell within Rosenthall's canal was outlined, and the area recorded. The nucleus of each cell was also measured. It was determined that discounting cells with a nucleus surface area less than 15 µm$^2$ would preclude duplicate neuron counting across multiple optical sections.

To quantify the BDNF gene therapy-mediated regeneration of the SGN neurites within the osseous spiral lamina, average pixel intensities of the neuronal labelling were calculated. All images were captured using identical settings. The fibre tracks through the spiral lamina were manually outlined in each of the exported TIFF files. The sum of all pixel intensities within that area was divided by the total designated area to give a sum of average pixel intensities per square micron.

Statistical analysis and graphs were generated using SigmaPlot software (Systat®). Treated and untreated cochleae were compared by a repeated measures one way ANOVA for both cell soma size and dendrite maintenance. A one way ANOVA was performed on ranked data to compare the efficiencies of tandem and alternating array configurations for the ex vivo data, with post-hoc Holm-Sidak multiple pairwise comparison. Data analysis included assessment for normal distribution and equal variance; where required, data were analyzed using non-parametric ranked ANOVA.

Calculating Transfection Efficiency

Transfection efficiency calculations were determined based on nuclear GFP labelled mesenchymal cell counts compared with universal nuclear fluorescence labelling with DAPI within regions of interest for ex vivo imaging of dissected fixed cochleae (FIG. 12 a, b).

Electrically-Evoked Auditory Brainstem Response (eABR) Measurements eABR was measured under isoflurane anaesthesia. The guinea-pigs were implanted with the 8 node electrode arrays (Cochlear ltd. Part number Z60274) as described for the microarray-based electroporation methodology, except that the implant was cemented in place (Ketac Cem Easymix dental cement, 3M ESPE AG, Germany), securing the array within the cochlea and emerging lead to the mastoid bone. The array lead was routed from the bulla to the scapulae, where the connector was implanted subdermally, encapsulated in parafilm. To undertake eABR measurements, the guinea-pigs were anaesthetised with isoflurane and an incision was made to access the microarray connector. This was attached to a stimulator (A-M systems analog stimulus isolator 2200, USA) set to provide stimulation via a bipolar (tandem) configuration. ABR recording electrodes (subdermal) were placed at the vertex of the skull and lateral temporal region on the implant side; a reference electrode was inserted in the flank. Alternating monophasic pulses of 100 µs duration were delivered via the cochlear implant array in the tandem configuration (bipolar), and averaged over 512 trials. A suprathreshold maximum stimulus was set, with successive 1 dB reductions driven by the auditory evoked workstation (as described for ABR recordings under Deafness model) in referenced to 1 mA at 70 dB. The p1 waveform latency of the eABR occurred around 400 µs from the stimulus onset. eABR amplitudes were measured as the p1–n1 difference (FIG. 16a).

Example 2

Close-Field Microarray-Based Electroporation of Confluent HEK293 Cells

HEK293 cells grown to confluence on coverslips coated with poly-D-lysine were overlayed with a solution comprising a brain derived neurotrophic factor (BDNF) gene therapy cassette (CMVp-3xflag-BDNF-IRES-hrGFP gene cassette) as described above, and subjected to electroporation. Electroporation was via a microarray comprising an 8 electrode linear microarray consisting of platinum ring electrodes 400 µm diameter×350 µm depth (Cochlear Ltd, Australia, part no. Z60276). The microarray was placed on top of the confluent cells.

Parameters varied were electrode configuration and electronic stimulation treatments.

Electrode Configurations were as shown in FIG. 3:
Tandem: four cathodes (−) then four anodes (+)–tip–total distance=5.4 mm;
Alternating (anode-cathode-anode-cathode-anode-cathode-anode-cathode)–total distance=5.4 mm;
Electrodes 1 and 8-electrode position 1=anode (+); electrode position 8=cathode (−) (separation=6 mm). The electrodes in the centre were not connected; and
Electrodes 1 and 2-electrode position 1=anode (+); electrode position 2=cathode (−) (separation=350 µm). The other electrodes progressing to the tip were not connected.

Electrostimulation treatments (voltage and pulses) were varied as follows (all pulses were 50 ms with 950 ms interval, using a CUY 21 square wave electroporator; NEPA GENE):
40V/10 pulses (40V/10P);
20 V/10 pulses (20V/10P); and
10 V/5 pulses (10V5P)
8 experiments were carried out per configuration/treatment combination.

Transfected cells expressing GFP were counted at 48 hours post-electroporation, using an epifluorescence microscope, after fixing in 4% paraformaldehyde and washing in phosphate buffered saline (PBS).

Data analysis ranked two way ANOVA with Holm-Sidak pair-wise comparison.

Results:

The data, summarised in FIG. 4, showed that electroporation of a planar sheet of HEK293 cells confirmed the findings of the in vitro and in vivo studies in showing that the 'tandem' electrode configuration provided higher transfection efficiency than the 'alternating' electrode configuration (P<0.001).

The tandem electrode configuration also provided significantly greater numbers of transfected cells than any of the other three configurations (P<0.001).

FIG. 4 shows that all configuration/treatment combinations provided significantly greater numbers (P<0.001) of transfected cells than the control (no electroporation—DNA present), except for the 20V/5 pulse treatment with the 1 and 8 electrode configuration (P=0.076), and the alternating, 20V/5P treatment (P=0.009). This means that the minimum configuration of 2 electrodes only 350 µm apart (config 1 and 2) was significantly effective, and a tandem configuration (with the same minimal gap between anode and cathode) provided the best results. The configuration of electrodes 1 and 8 was nonetheless effective, especially at the higher voltage/pulse regimes. The difference in effectiveness between the alternating and tandem electrode configurations appears to correlate with the electric fields modelled for these configurations (see FIG. 2A), which show the tandem electrode configuration as providing the most strongly focussed electric field.

The electroporation effect extended from <400 µm from the electrodes to a distance of ~2.5 mm.

Figure 5:
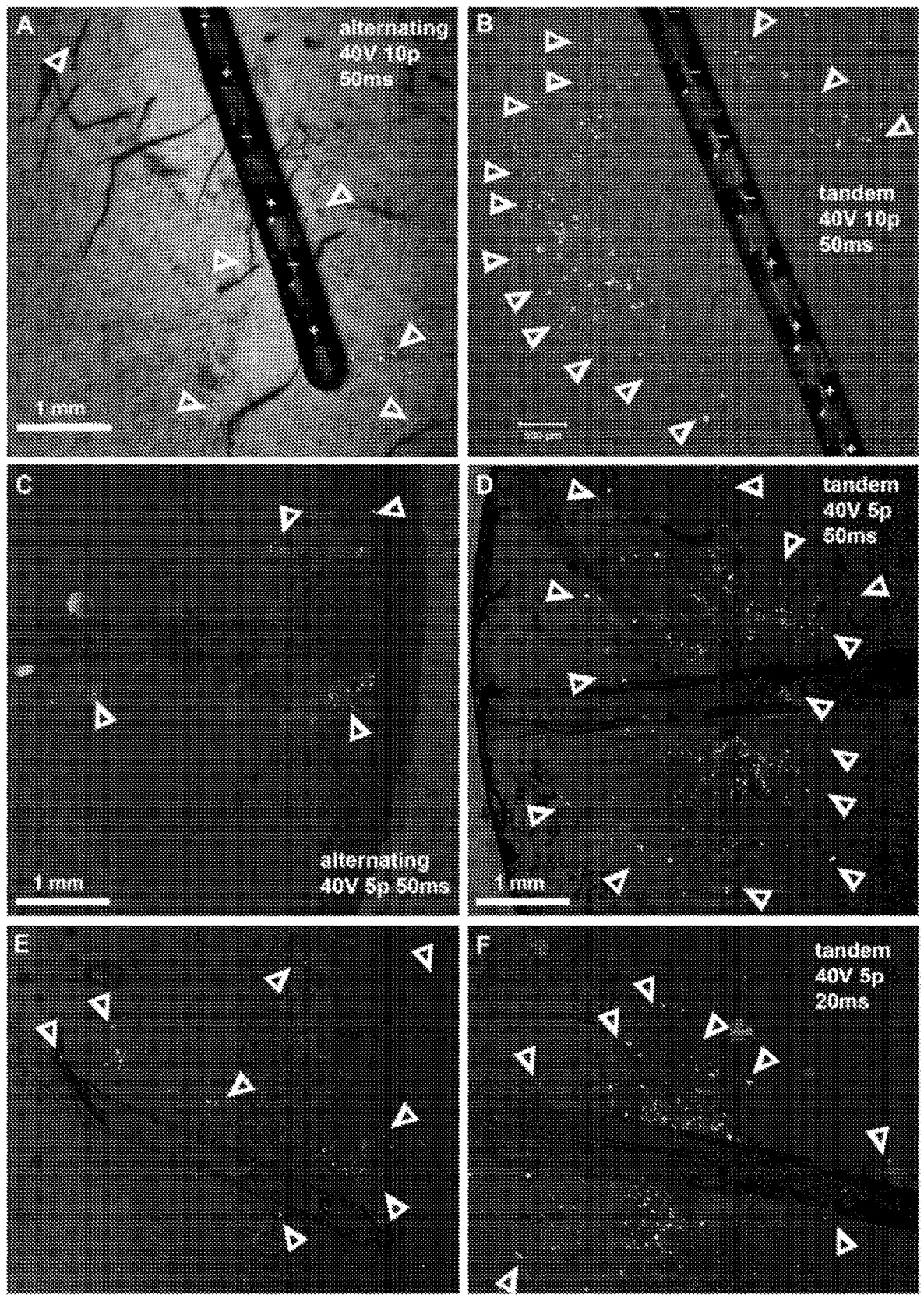
FIG. 5 Shows fluorescence imaging of Green Fluorescence Protein (GFP) labeling in the nuclei of HEK293 cells in monolayers. Cells were imaged 48 hours after close-field electroporation with a naked cDNA construct which drove the GFP expression under a CMV promoter. Tandem & alternating configurations of the microarray are as shown: A. and B. are images with the microarray superimposed on top of the HEK293 cell monolayer to indicate the scale; 40V, 10 pulses, 50 ms square wave close-field electroporation. C and D. 40V, 5 pulses, 50 ms. E and F. 40V, 5 pulses, 20 ms. The arrowheads indicate regions of transfected cells. Dark lines in Panels C-F indicate microarray placement.
Figure 6:
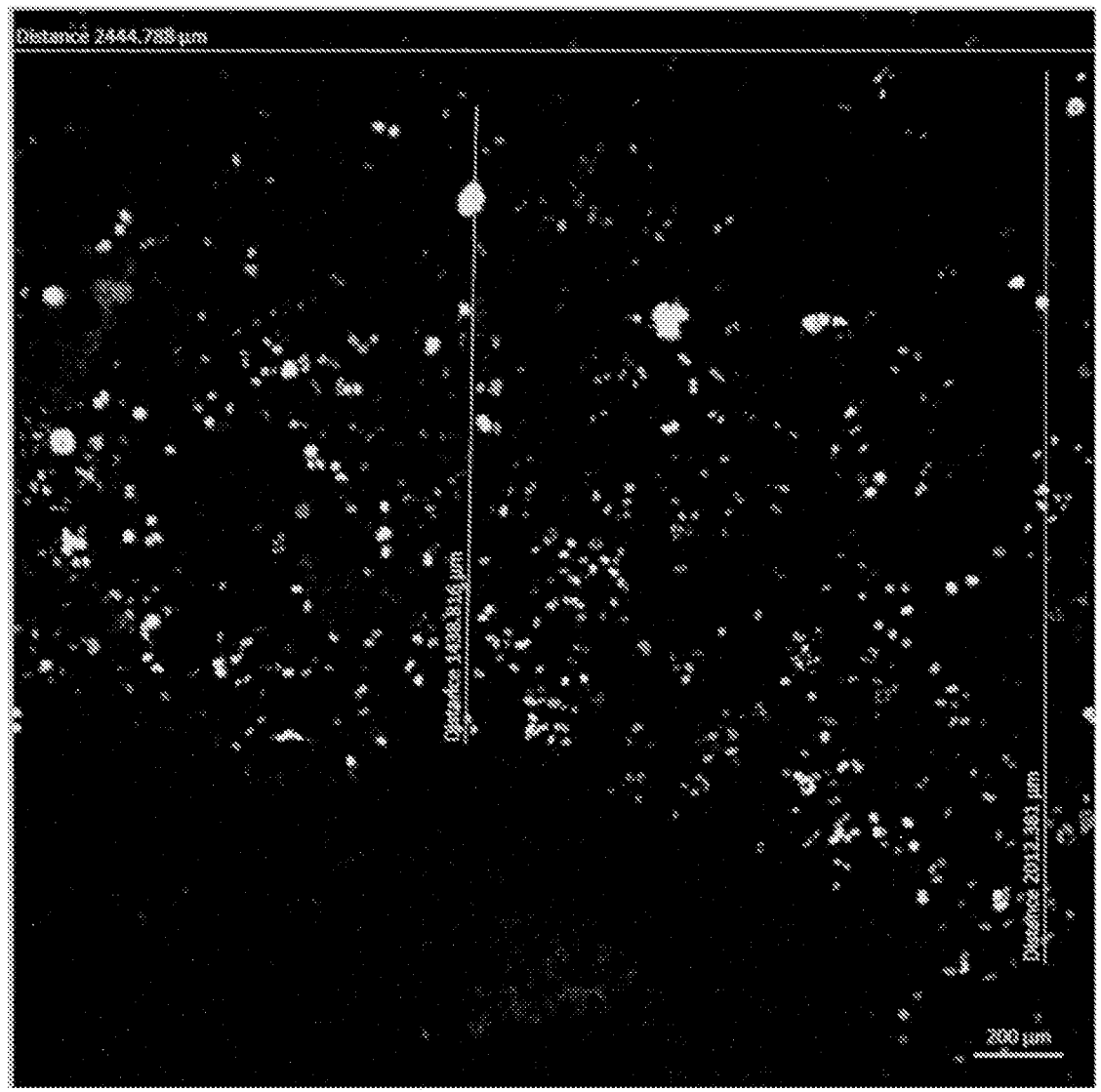
FIG. 6 provides a fluorescence photomicrograph illustrating HEK293 cells transfected using CFE methodology according to the present application employing a "tandem" electrode configuration (as illustrated in FIG. 6B) with the microarray overlaid on the fixed HEK293 cell sheet. Transfected cells are evident as GFP positive. Cells were treated with 10×40V pulses at 50 ms per pulse.

FIGS. 5 and 6 illustrate transfection results for this in vitro model of CFE utilising confluent sheets of HEK293 cells. FIGS. 5A to 5F show the 8-electrode linear array as placed on top of the cells, as a 2D model to test for the difference in transfection efficiency between the alternating and tandem electrode configurations. Cells were treated with 10×40V pulses at 50 ms per pulse. The arrowheads indicate regions of transfected cells displaying nuclear localization of GFP fluorescence 48 hours post-transfection. The greater efficiency of the 'tandem' microarray configuration (FIGS. 5A, 5C and 5E) over the 'alternating' microarray configuration (FIGS. 5B, 5D and 5F) is clearly evident. Note the close-field effect where cell transfection extends to a boundary approximately 2.5 mm from the array (FIGS. 5 and 6). This provides spatial regulation of cell transfection.

Example 3

Ex Vivo Cochlear Gene Delivery

An ex vivo model was developed to establish the potential of microarray-based close-field electroporation gene delivery. The CMVp-BDNF3xFLAG-IRES-GFPnls gene cassette (described in Example 1) was microinjected into the scala tympani perilymphatic fluid compartment of normal intact guinea-pig cochleae, via the round window, and then an eight-node cochlear implant microarray was inserted (FIG. 1 c, d). The microarray was configured as either alternating anodes and cathodes ('alternating' configuration), or as a 'tandem' array where four adjacent electrodes (350 µm diameter platinum rings with 300 µm separation) were wired in parallel as the anode (distal end of the array), and the other electrodes provided a common cathode ('tandem' configuration) (FIG. 1d). Transduction of cells with the gene cassette was achieved across the tested voltage range (4 V, up to 100 V; 5-20 pulses, 50 ms duration) in 76 experiments (Table 1). The lateral walls of the cochleae were removed and the tissue placed in organotypic culture ten minutes after electroporation. From 18 hours in culture, GFP reporter fluorescence was prominent in mesenchymal cells lining scala tympani and scala vestibuli including the perilymphatic surface of Reissner's membrane (FIG. 7a,b, FIG. 8, and FIG. 9 b, c, d), and was maintained for the duration of organotypic cultures (up to 4 days). The GFP positive cells were confined to the basal turn region, within ~1 mm of the array, consistent with spatially constrained electroporation of the cells within the cochlear perilymphatic chambers. Middle and apical regions of the cochlea were devoid of GFP positive cells (FIG. 7c). Control experiments where DNA was delivered without electroporation yielded minimal GFP positive cell counts (mean=3±0; n=2). Cryosectioning of electroporated cochleae revealed that the transduction was effectively constrained to mesenchymal cells (FIG. 9b). Hair cells and supporting cells of the organ of Corti, or other cell types facing scala media, were not transduced. Expression of BDNF by transduced cells was confirmed by anti-FLAG immunolabeling in both whole-mount and sectioned tissue (FIG. 7d, FIG. 9d). CFE was effective from 10V in both microarray configurations (combined data 26.4±8.3, n=5; P=0.033; one sample t-test; FIG. 7e).

Figure 7:
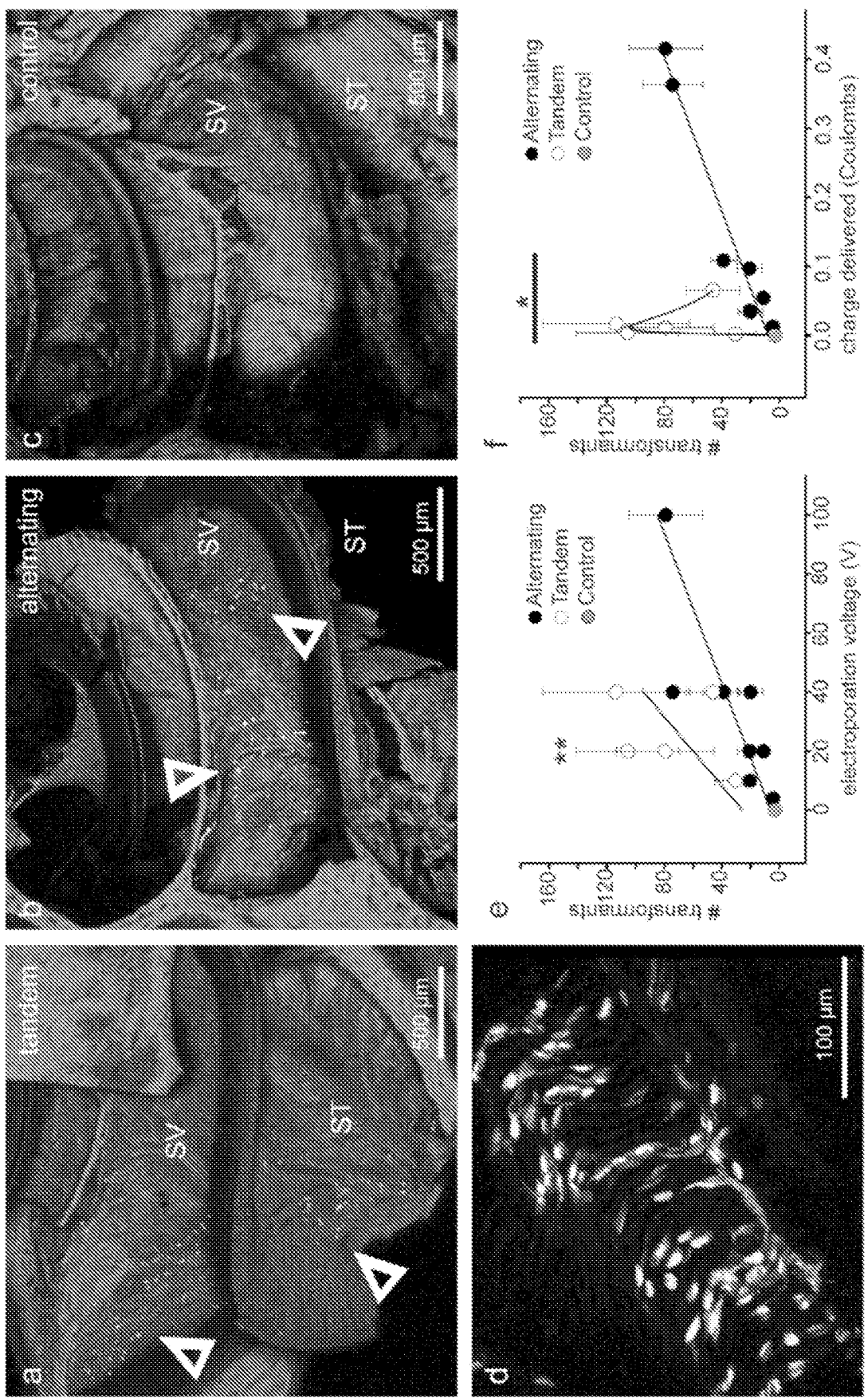
FIG. 7 shows results for ex vive CFE of guinea pig *cochleae* using cochlear implant electrode microarrays in alternating or tandem electrode configurations: a), b) confocal projected images of the distribution of transformed mesenchymal cells (nuclear localized GFP fluorescence) lining the perilymphatic compartments (scala tympani (ST) and scala vestibuli (SV)) of the cochlea (white arrowheads). Note the basal location of the transformants, which demonstrates site specificity of gene delivery a) 20V—5 pulses tandem configuration; b) 40V—20 pulses alternating configuration. c) Control: BDNF-GFP plasmid loading with cochlear implant, without CFE. d) BDNF production by the transformed mesenchymal cells was confirmed by anti-FLAG immunofluorescence co-incident with the GFP nuclear labelling. e) Effect of voltage on electroporation efficiency (GFP+ve cells) for the two different close-field electroporation modalities. Lines of best fit: tandem array, y=a+b*x, where a=25.8, b=1.71, $R^2$=0.39; alternating array.

The tandem microarray configuration demonstrated greater gene delivery efficiency than the alternating configuration, with an asymmetric optimum in the lower range of applied voltages (~20V) and a minimum effective charge delivery of 0.01 coulombs (FIG. 7 e,f). Cell counts of up to 310 GFP positive cells were achieved with five 20V pulses, with no increase with additional pulses. In contrast, the alternating

TABLE 1

Summary of nuclear GFP labelled mesenchymal cell counts arising from ex vivo cochlear close-field electroporation gene delivery.

| Voltage (V) | Wiring configuration | Pulses | GFP+ Range | Mean GFP+ | *Estimated charge delivery (mC) | n = | Current range (mA) |
|---|---|---|---|---|---|---|---|
| 100 | Alternating | 50 | 52 | 52 | 859.1 | 1 | n/d |
| 100 | Alternating | 20 | 53-130 | 79 | 415.5 | 2 | 80-100 |
| 60 | Alternating | 10 | 94 | 94 | 164.8 | 1 | 60 |
| 40 | Alternating | 20 | 0-300 | 74 | 363.1 | 17 | 60-140 |
| 40 | Alternating | 10 | 23-59 | 38.8 | 108.7 | 4 | 110-120 |
| 40 | Alternating | 5 | 11-67 | 29 | 34.4 | 6 | 60-110 |
| 20 | Alternating | 20 | 1-57 | 20.8 | 97.1 | 6 | 10-40 |
| 20 | Alternating | 10 | 8-14 | 11 | 54.6 | 2 | 30 |
| 10 | Alternating | 20 | 25-16 | 20.5 | 35.8 | 2 | <10 |
| 8 | Alternating | 20 | 17 | 17 | 65.0 | 1 | 90 |
| 4** | Alternating | 20 | 18 | 18 | 13.0 | 1 | <10 |
| 40 | Tandem | 20 | 5-180 | 46.1 | 65.6 | 10 | 20-50 |
| 40 | Tandem | 5 | 32-245 | 113.5 | 17.2 | 4 | 30 |
| 20 | Tandem | 10 | 13-165 | 79.4 | 11.2 | 5 | ≤10 |
| 20 | Tandem | 5 | 1-310 | 105.4 | 4.0 | 8 | ≤20 |
| 10 | Tandem | 5 | 2-47 | 30.3 | 2.3 | 3 | <10 |
| 4** | Tandem | 10 | 4-11 | 8.3 | 3.4 | 3 | <10 |
| 4** | Tandem | 5 | 1-13 | 8.3 | 1.9 | 4 | <10 |
| 0** | n/a | 0 | 1-4 | 2.8 | 0 | 5 | 0 | n/d—not determined,
n/a—not applicable;
GFP+ is the number of transformed mesenchymal cells showing nuclear localized green fluorescence protein signal.
* based on passive resistance measurement; total charge delivered to array.
**Note: Control experiments where DNA was delivered without electroporation yielded minimal GFP positive cell counts (mean ± s.e.m. = 2.8 ± 0.5; n = 5). Close-field electroporation was effective from 4 V (combined mean = 9.5 ± 1.8, n = 8; P = 0.017; t-test).

configuration provided a linear increase in transformation efficiency with increasing voltage to the highest test level and charge delivery (100V, 0.416 coulombs FIG. 7 e,f). Comparing transfectants between 'tandem' and 'alternating' array configurations for all data between 10V and 40V showed a significantly greater efficiency with the 'tandem' array (P=0.039, ranked one way ANOVA).

Example 4

In Vivo Cochlear Gene Delivery

In 16 experiments, a cochlear implant microarray was surgically inserted into anaesthetised guinea-pigs for CFE gene delivery (FIG. 10). In vivo CFE yielded comparable transformed cell numbers to the et vivo experiments (compare FIGS. 7, 8 and 9b with FIGS. 9a and 11; and Table 1 with Table 2).

The optimum ex vivo transfection parameters for the two array configurations were mapped to in vivo experiments. 'Tandem' CFE produced more consistent levels of transfection in vivo than did 'alternating' CFE (tandem: 20V—5 pulses, range 45-373, mean=169.1±47.9, n=7; alternating: 40V—20 pulses, range 1-99, mean=47.4±21.5, n=5). In addition, transduction via alternating CFE at the 20V—5 pulse parameter was 8-fold less than tandem CFE (15.5±9.0, n=4) (FIG. 11c; P=0.043, t test). All cochleae were fixed 3-4 days after electroporation. Maximum transfection efficiency of the tandem array configuration was determined in three experiments (20V—5 pulses) at 4 days post CFE. These experiments yielded GFP cell counts ranging from 179-373 cells. Regions of interest that included at least 100 cells were analysed for GFP and DAPI fluorescence nuclear labelling (FIG. 12). The average number of double-labelled mesenchymal cells was 42.5%±3.3%. Two control experiments utilized electroporation with a GFP-null vector, no GFP fluorescence cells were detected. Two controls where the left cochlea was perfused with the GFP expressing BDNF plasmid followed by insertion of the electrode array, without electroporation resulted in 6 and 7 GFP positive cells, respectively, four days post-electroporation (not shown).

Example 5

In Vivo BDNF Gene Therapy Promotes Spiral Ganglion Neurite Regeneration

A kanamycin—furosemide ototoxic treatment was used to selectively destroy sensory hair cells and produce a deafened guinea-pig model, where, within two weeks, the peripheral neurites of the SGN degenerate within the osseous spiral lamina and the SGN somata atrophy (see Example 1). Both alternating configuration CFE and tandem configuration CFE BDNF gene delivery to the left cochlea produced pronounced regeneration of the peripheral spiral ganglion neurites, and increased the size of somata

TABLE 2

Summary of GFP counts of transfected mesenchymal cells with close-field electroporation in vivo.

| Wiring configuration | Voltage (V) | Pulses | GFP+ range | Mean GFP+ | Estimated* charge delivery (mC) | n = | Current range (mA) |
|---|---|---|---|---|---|---|---|
| No electroporation | 0 | 0 | 6-7 | 65 | 0 | 2 | 0 |
| Alternating | 20 | 5 | 0-33 | 15.5 | 37.5 | 4 | 30-40 |
| Alternating | 40 | 20 | 1-99 | 47.4 | 122.5 | 5 | 40-50 |
| Tandem | 20 | 5 | 45-373 | 169.1 | 8.3 | 7 | 10 |

*based on passive resistance measurement; total charge delivered to array; GFP+ is the number of transformed mesenchymal cells showing nuclear localized green fluorescence protein signal.

compared with the untreated (right) cochlea of deafened guinea pigs (analysed from 7-21 days post gene delivery) (FIGS. 13, 14, 15). The extent of regeneration of the peripheral auditory nerve was determined by analysing the intensity of β-tubulin immunofluorescence within the osseous spiral lamina region (basal turn) (P=0.017, comparing matched treated and untreated cochleae of each of four animals, paired t-test; FIG. 13d, Table 3). Similarly, the average SGN somata size was approximately 40% larger in the BDNF gene therapy-treated (left), versus untreated (right) cochleae of these animals (basal turn, P=0.012, paired t-test; FIG. 13e, Table 3). The deafened guinea pig organ of Corti typically exhibited a flattened epithelium due to the loss of hair cells and supporting cells (FIG. 13b, FIG. 15a). Neurite processes typically branched beyond the habenula perforata and descended through the basilar membrane into the scala tympani region (FIG. 13a, FIG. 1S). Ectopic branching also extended to the inner sulcus, and outer sulcus—spiral ligament region, within scala media (FIG. 14, FIG. 15). The neurite regeneration extended beyond the basal turn mesenchymal cell transfection zone, to the mid-turn region (FIG. 13a), likely reflecting diffusion of the secreted recombinant BDNF. Robust immunolabeling for the Schwann cell marker aspartoacylase (Mersmann, N. et al. (2011), "Aspartoacylase-lacZ knockin mice: an engineered model of Canavan disease", PLoS One 6, e20336) indicated remyelination of regenerated neurites (FIG. 13c).

TABLE 3

Animals histologically examined for neurite regeneration following close-field electroporation gene delivery - comparison between treated and untreated cochleae from the

| Animal ID | Days between deafening and therapy | Days between therapy and tissue collection | Average SGN cell soma size | | Average pixel intensity per $\mu m^2$ dendrites | |
|---|---|---|---|---|---|---|
| | | | Treated | Untreated | Treated | Untreated |
| GP287 | 16 | 17 | 215.9 | 149.3 | 60.0 | 21.4 |
| GP284 | 17 | 11 | 257.3 | 200.4 | 33.0 | 14.3 |
| GP283 | 14 | 7 | 297.7 | 192.6 | 73.2 | 19.1 |
| GP269 | 21 | 21 | 216.9 | 169.9 | 40.5 | 10.0 |

* For guinea pigs 287, 284, and 283, alternating configuration of the array was used. For guinea pig 269 a tandem configuration was used.

Example 6

Enhanced Cochlear Implant Performance

Thresholds for electrically-evoked auditory brainstem response (eABR) via the cochlear implants were determined four weeks post-deafening, which was two weeks after cochlear implantation and tandem configuration CFE gene delivery (20V—5 pulses) using either the BDNF-GFP gene cassette (n=5), or the control (GFP) vector (n=5). The improvement in auditory brainstem neural recruitment due to the BDNF gene therapy was such that the mean eABR threshold for the BDNF gene therapy group was less than half that of the control group (BDNF group 145.6 µA±19.3; control group 319 µA±26.0; P<0.001, ANOVA, Holm-Sidak all pairwise comparison) (FIG. 16; Table 4), with no overlap in data (FIG. 16c).

These results show a considerably greater improvement in cochlear implant performance than that reported for direct BDNF drug delivery in an earlier study (Landry, T. G. et al (2011), "Spiral ganglion neuron survival and function in the deafened cochlea following chronic neurotrophic treatment", *Hear Res* 282:303-313). Complementing this, the dynamic range (growth function) of the eABR was significantly increased in the BDNF gene therapy treatment group (FIG. 16 b, d), with a considerable extension of the range of stimulus eliciting growth of the eABR. Thus BDNF gene therapy restored the cochlear

TABLE 4 eABR Results following close-field electroporation gene delivery of a BDNF therapeutic cassette versus GFP control cassette.

| Cochlea ID | treatment | 2 week threshold |
|---|---|---|
| GP222-L | BDNF-20 V/5 Pulses | 49 dB/88 µA |
| GP213-L | BDNF-20 V/5 Pulses | 57 dB/223 µA |
| GP205-L | BDNF-20 V/5 Pulses | 55 dB/177 µA |
| GP204-L | BDNF-20 V/5 Pulses | 53 dB/140 µA |
| GP203- L | BDNF-20 V/5 Pulses | 52 dB/125 µA |
| GP214-L | GFP-20 V/5 Pulses | 62 dB/397 µA |
| GP202-L | GFP-20 V/5 Pulses | 61 dB/353 µA |
| GP201-L | GFP-20 V/5 Pulses | 58 dB/250 µA |
| GP200-L | GFP-20 V/5 Pulses | 60 dB/315 µA |
| GP199-L | GFP-20 V/5 Pulses | 59 dB/280 µA | nerve recruitment towards pre-treatment levels (FIG. 17). By way of comparison, acute cochlear implant stimulation in normal-hearing guinea-pigs (where both the auditory nerve and the sensory hair cells are intact; FIG. 17a,c), provided a mean eABR threshold of 151.2 µA±19.4 (n=5). This was not significantly different from the BDNF gene therapy group (P=0.771; one way ranked ANOVA, Holm-Sidak all pairwise comparison) (compare with FIG. 16c), indicating recovery of threshold, even discounting possible augmentation of this baseline in this control group due to inner hair cell stimulation. The baseline for the CFE-mediated BDNF gene therapy was two weeks post deafening. Reference eABR recordings at the time of implantation had a mean threshold of 223.7 µA±7.4 (FIG. 16 b,c; n=10). This was significantly higher than the BDNF gene therapy group at 2 weeks treatment (P<0.001; see FIG. 16c), but significantly less than the GFP vector control group at 2 weeks treatment (P=0.001; FIG. 16c), indicating the further deterioration in the spiral ganglion over time in the absence of gene therapy. The functional recovery of eABR input-output gain with BDNF gene therapy was re-confirmed at four weeks post-treatment (6 weeks after deafening) in cases where the interface had not failed (n=2 BDNF-GFP vector; n=4 GFP only control vector) (FIG. 18). Overall, these results demonstrate a remarkable functional enhancement of the cochlear implant-neural interface arising from restoration of the peripheral spiral ganglion neurites following CFE-mediated BDNF gene therapy.

Example 7

Analysis of Pulse Width

Here pulse width was assessed for transduction of HEK293 cell monolayers using the 8 electrode microarray in Tandem configuration for close filed electroporatoin.

The cells were transduced as described in Example 2. In this example of close field electroporation, voltage and pulse number were kept constant at 40V and 5 pulses respectively, and the square-wave pulse width was varied between 100 µs and 100 ms, with a GFP reporter cDNA construct at 2 µg/µL in TRIS-buffered saline. After 48 hours in culture, the GFP positive cells were fixed and then counted as GFP positive labelling. These data were best fit by the relationship: f=249*(1−exp(−0.025*x)). Data shown are mean+/−s.e.m., n=3-9 experiments for each pulse duration; 40 Volts, 5 pulses of varying duration (plus a 0 V, 0 pulse control, n=5). These data (FIG. 19) indicate that 90% of the maximum possible electroporation efficiency is achieved with pulse widths of 100 ms; 50 ms pulses enable 78% of the maximum efficiency; 40 ms represents the decay constant for this exponential curve, i.e. where 67% of possible transduction occurs. Thus at 5 decay constants (200 ms), these data predict 99% maximum transduction.

Discussion

This study indicates that close-field electroporation of naked DNA utilising a cochlear implant microarray enables high efficiency gene delivery. Since the electric field strength decays quadratically with the distance from electrodes, the microarray-based CFE allows site-specific transformation of the mesenchymal cells lining the perilymphatic compartments of the cochlea. This somatic cell gene therapy produced the neurotrophin support critical to the viability of the primary auditory neurons, a signal lost with the death of the cochlear hair cells. In response to BDNF expression by the mesenchymal cells, the regeneration of the peripheral auditory neurites extended back along their original track within the osseous spiral lamina. This porous structure is contiguous with the perilymph and the re-growth in mid-cochlear levels likely reflects apical diffusion of BDNF from the basal transduction site. BDNF expression drove regeneration of SGN peripheral neurites to close proximity with the electrode array. This regeneration, accompanied by remyelination and increased somata size, make the spiral ganglion neuron highly amenable to more precise electrical stimulation, with reduced stimulus intensity. The study also demonstrates that the configuration of the electrodes within the microarray is a major determining factor for CFE transformation efficiency. Gene delivery was most efficient using a 'tandem' array configuration, compared with the 'alternating' electrode configuration. This points to the nature of the shape of the current paths around the electrodes as playing a role in the transient dielectric breakdown of the cell plasma membrane that enables movement of negatively charged DNA into the cells. There was minimal transduction of other cell types (within the cochlear partition) and this is probably due to the limited diffusion of DNA from the perilymphatic compartment in the few minutes required for DNA loading and CFE. The eABR input-output function of the BDNF gene therapy-treated cochleae was restored towards control levels (2 weeks post deafening, FIG. 17 c,d), indicating that recruitment of smaller sub-populations of spiral ganglion neurons may be achievable with increased electrode density, due to lowered stimulus thresholds. This has significant translational ramifications for the performance of future generation cochlear implants utilising such complementary gene therapy. Currently pitch perception is largely lacking in cochlear implant recipients, making tonal colour and music appreciation a major potential gain if the microarray—spiral ganglion nexus can be improved.

This microarray-based CFE should have broad translational significance as it overcomes many constraints of other gene therapy platforms, including the use of naked DNA, delivered by highly localised electrical fields without significant current spread, reducing extraneous electrical stimulation and local tissue damage. In the case of the cochlear implant array, the ability of CFE utilizing a few pulses of ~10V to produce significant numbers of transformed cells is well within the operational parameters of current generation cochlear implant devices and other neural interfaces.

BDNF neurotrophin gene therapy demonstrated here has broad applicability to neural repair, but the application is not limited by particular gene constructs. For example, it is contemplated that applications of the present methodology will include treating brain disorders, such as Parkinson's disease, where CFE may provide a safe and efficient alternative to proposed viral vector-based transduction of neurons and glia in the striatum for sustained production of dopamine. Safety concerns are considerably mitigated in comparison with viral vector-based gene therapy approaches, where uncontrolled spread of the virus can lead to undesirable off-target effects, and the likelihood of immunological reactions is a major barrier to implementation. Along with the advantage of using circularized naked DNA which does not integrate into the genome, thereby eliminating the possibility for random insertional mutagenesis, CFE gene therapy also removes the DNA packaging constraints associated with viral-vectors. The therapeutic gene cassette can either be directly delivered to the target site, or integrated into the microarray interface, while the microarray itself could be used acutely, for CFE-mediated gene therapy alone, or chronically, implanted to establish an enhanced neural interface, as shown in the deafened cochlea model exemplified here.

Example 8

Further Studies Investigating Electroporation Parameters

Further studies were carried out to further characterise parameters important for optimal electroporation, including electrode array configuration, voltage applied, number of electroporation pulses, pulse duration, pulse gap, and investigation into CFE-mediated cell death.

A) Materials and Methods
HEK-293 Cell Line

The cells were maintained in Dulbecco's Modified Eagles Medium (DMEM) supplemented with 10% Heat-Inactivated Fetal Bovine Serum (HT-FBS, Life Technologies), 1% Penicillin/Streptomycin mix (Life Technologies), 1% Non-Essential Amino-Acids (NEAA, Life Technologies). Cells were split and plated on coverslips the day prior to electroporation. Cells were electroporated at 80% confluence.
DNA Plasmid The construct used in these experiments contained a nuclear localized green fluorescent protein reporter gene (GFPnls), driven by a chicken-B-actin/cytomegalovirus hybrid promoter (CAG). Plasmid DNA was purified from *E. coli* using a column chromatography purification kit (Qiagen) and resuspended at 2 µg/µl and in 50 mM Tris-buffered saline (pH 7.4) before transformation.
Close-Field Electroporation Electroporation was performed on the HEK293 cell monolayers with an In Vivo Square Wave Electroporator (Sonidel Ltd, CUYEDIT), connected to a linear eight-node cochlear implant array consisting of platinum ring electrodes (400 µm diameter×350 µm length) with 350 µm separation (Cochlear Ltd, Australia, part no. Z60276). The coverslip was removed from the cell culture well and placed on a flat surface. The electrode array was lowered onto the coverslip. The DNA was applied to each coverslip (20 µl at 2 µg/µl) electroporation was initiated using the desired electrode configurations and electroporation parameters.
Study of CFE-Mediated Cell Death Using the 'Tandem' array configuration, the pulse was set at 40V, 1, 5 or 40 pulses, 40 ms pulse duration, 1 pulse/sec. Tris-buffered saline was applied to the coverslip instead of the DNA. Immediately after electroporation, coverslips were placed in a humidity chamber for 2 mins. Coverslips were then placed in fresh, warmed media and returned to the incubator for 30 minutes. Cell death was identified by propidium iodide fluorescence, where propidium iodide was added to the media at a concentration of 1:1000 and was incubated for 5 minutes. Coverslips processed and imaged using the confocal LSM with 633 nm excitation using a HeNe laser.
B) Study of Variation in Electrode Array Configuration on CFE The electrodes within the array were configured as anodes and cathodes with the following arrangement (illustrated in FIG. 20): 1+2 (a single anode and a single cathode with 350 µm separation), 1+5 (a single anode and a single cathode with 2.45 mm separation), 1+8 (a single anode and a single cathode with 4.55 mm separation), tandem (four juxtaposed cathodes, then four anodes, all elements with 350 µm separation; total length 5.4 mm) and alternating (alternating cathode and anode with 350 µm separation, total length 5.4 mm).

This initial study of the effect of varying electrode configuration on transformation efficiency and spatial distribution used 40V, 10 pulses, 50 ms duration, 1 pulse/sec.

Significant numbers of cells were transformed by CFE, evident as green fluorescence in the cell nuclei (FIGS. 21A to 21F). The numbers of cells and spread of cells provided a readout of the effective electric field (FIG. 21).

The results demonstrate that there is a significant effect of varying electrode spacing and electrode association. Ranked One-Way ANOVA showed that the configuration of the electrodes within the array had a significant effect on the number of transformed cells (P<0.001; n=4 per configuration). All CFE configurations produced significant cell transformation compared with the control group (FIG. 22; Table 5; ranked one way ANOVA with Holm-Sidak pairwise comparisons (P<0.001 for all except '1+8' (P=0.016), n=4 per group)).

The control group (no CFE) exhibited 0.8±0.8 GFP positive cells per coverslip. The different CFE configurations resulted in variation in numbers of transformed cells between 7.0±3.1 ('1+8') and 219.0±37.7 ('tandem'). The 1+2 CFE resulted in a circular field of cells with the electrodes at the centre (FIG. 21A) of ~1 mm diameter, whereas the alternating CFE produced a linear bias to the field of transformants extending the length of the array (~5 mm) FIG. 21E). 1+5 and 1+8 CFE configurations yielded smaller average transformant numbers, which had a broad, low density distribution (FIGS. 21C, D). The transformation efficiency with the tandem configuration was significantly higher than any of the other configurations (see Table 5). These data suggests that a key feature of CFE is sub mm separation between the anode and cathode poles within the array; highlighting the difference between transformation using local electric field focusing and conventional 'open-field' electroporation, where the target field is located between separated electrodes.

TABLE 5

Statistical analysis for CFE electrode configuration by one-way ANOVA with Holm-Sidak post-hoc comparisons (n = 4/group)

| Comparison | Unadjusted P | Critical Level | Significance |
| --- | --- | --- | --- |
| tandem vs. 1 + 5 | <0.001 | 0.005 | Yes |
| tandem vs. 1 + 8 | <0.001 | 0.006 | Yes |
| Alt vs. 1 + 5 | <0.001 | 0.006 | Yes |
| 1 + 2 vs. 1 + 5 | <0.001 | 0.007 | Yes |
| tandem vs. 1 + 2 | 0.003 | 0.009 | Yes |
| tandem vs. Alt | 0.003 | 0.010 | Yes |
| 1 + 8 vs. 1 + 5 | 0.014 | 0.013 | No |
| 1 + 2 vs. 1 + 8 | 0.045 | 0.017 | No |
| Alt vs. 1 + 8 | 0.045 | 0.025 | No |
| 1 + 2 vs. Alt | 1.000 | 0.050 | No |

B) Electrical Pulse Parameters

Utilising the most efficient CFE electrode configuration (tandem), the effect of electrical pulse parameters was systematically resolved.

i) Voltage Amplitude

Using the 'Tandem' array configuration, the pulse parameters were set at 10, 20 or 40V, 10 pulses, 40 ms pulse duration, 1 pulse/sec.

The numbers of transformed cells increased significantly with increasing pulse amplitude (40 ms duration, 10 pulses, 1/s; FIG. 23; Table 6). The 40 V amplitude produced ~8 times greater transformation than the 20 V amplitude (170+19.7 versus 22.7±5.9; n=6 per group). No transformed cells were detected in the control experiments (n=6).

TABLE 6

Statistical analysis for voltage amplitude by one-way ANOVA with Tukey's Test post-hoc comparisons n = 6/group)

| Comparison | Diff of Ranks | q | P < 0.05 |
| --- | --- | --- | --- |
| 40 V vs control | 108.000 | 6.235 | Yes |
| 40 V vs 10 V | 71.000 | 4.099 | Yes |
| 40 V vs 20 V | 37.000 | 2.136 | No |

TABLE 6-continued

Statistical analysis for voltage amplitude by one-way ANOVA with Tukey's Test post-hoc comparisons n = 6/group)

| Comparison | Diff of Ranks | q | P < 0.05 |
| --- | --- | --- | --- |
| 20 V vs control | 71.000 | 4.099 | Yes |
| 20 V vs 10 V | 34.000 | 1.963 | No |
| 10 V vs control | 37.000 | 2.136 | No | ii) Pulse Number

Using the 'Tandem' array configuration, the pulse was set at 10 or 20V, pulse number ranging from 1-40 (1, 3, 5, 10, 20 and 40), 40 ms pulse duration, 1 pulse/sec.

Forty volts produced significantly greater cell transformation than twenty volts across the range of pulse numbers (2 way ranked ANOVA, P<0.001). At 40V, all pulse numbers (1, 3, 5, 10, 20, 40) resulted in significantly greater transformation than the control (no CFE); ranked ANOVA, multiple Comparisons versus Control Group (Holm-Sidak method; P<0.001 above 1 pulse; P=0.031 1 pulse). Cell transformation had a bell-shaped distribution with regard to pulse number with tandem configuration CFE (40V, 40 ms; n=6 per group except for 5 pulses (n=9)) (FIG. 24; Table 7), with 5, 10 and 20 pulses providing the maxima (range 147-170 cells) with no significant difference between these treatments (ANOVA, Holm-Sidak comparisons). At 20V, 3, 5, 10 and 20 pulse numbers resulted in significantly greater transformation than the control (no CFE); ranked ANOVA, multiple Comparisons versus Control Group (Holm-Sidak method; P<0.003). Cell transformation had a bell-shaped distribution with regard to pulse number with tandem configuration CFE (20V, 40 ms; n=6 per group) (FIG. 24; Table 7), 10 pulses providing the maxima (22 GFP+ve cells). There was a decline in transformed cell numbers at 40 pulses for both 20 and 40V. This was explained by the noticeable increase in cell death proximal to the electrode array with prolongation of the pulse train detected using propidium iodide fluorescence (FIG. 25).

TABLE 7

Statistical Analysis for pulse number, using A) 20 V (n = 6/group) and B) 40 V (n = 6/group (except 5 n = 9/group)), 40 ms duration pulses, by one-way ANOVA with Holm-Sidak post-hoc comparisons.

| A) 20 V pulses | | | | | |
| --- | --- | --- | --- | --- | --- |
| Comparison | Diff of Means | t | Un-adjusted P | Critical Level | Significance |
| 20 V: 10 pulses vs. 1 pulse | 18.250 | 3.642 | <0.001 | 0.003 | Yes |
| 20 V: 10 pulses vs. 40 pulses | 17.000 | 3.393 | 0.001 | 0.004 | Yes |
| 20 V: 5 pulses vs. 1 pulse | 13.583 | 2.711 | 0.009 | 0.004 | No |
| 20 V: 5 pulses vs. 40 pulses | 12.333 | 2.461 | 0.017 | 0.004 | No |
| 20 V: 10 pulses vs. 3 pulses | 9.583 | 1.913 | 0.060 | 0.005 | No |
| 20 V: 10 pulses vs. 20 pulses | 9.417 | 1.879 | 0.065 | 0.005 | No |
| 20 V: 20 pulses vs. 1 pulse | 8.833 | 1.763 | 0.083 | 0.006 | No |
| 20 V: 3 pulses vs. 1 pulse | 8.667 | 1.730 | 0.089 | 0.006 | No |
| 20 V: 20 pulses vs. 40 pulses | 7.583 | 1.513 | 0.135 | 0.007 | No |
| 20 V: 3 pulses vs. 40 pulses | 7.417 | 1.480 | 0.144 | 0.009 | No |

TABLE 7-continued

Statistical Analysis for pulse number, using A) 20 V (n = 6/group) and B) 40 V (n = 6/group (except 5 n = 9/group)), 40 ms duration pulses, by one-way ANOVA with Holm-Sidak post-hoc comparisons.

| | | | | | |
|---|---|---|---|---|---|
| 20 V: 5 pulses vs. 3 pulses | 4.917 | 0.981 | 0.330 | 0.010 | No |
| 20 V: 5 pulses vs. 20 pulses | 4.750 | 0.948 | 0.347 | 0.013 | No |
| 20 V: 10 pulses vs. 5 pulses | 4.667 | 0.931 | 0.355 | 0.017 | No |
| 20 V: 40 pulses vs. 1 pulse | 1.250 | 0.249 | 0.804 | 0.025 | No |
| 20 V: 20 pulses vs. 3 pulses | 0.167 | 0.0333 | 0.974 | 0.050 | No |

B) 40 V pulses

| Comparison | Unadjusted P | Critical Level | Significance |
|---|---|---|---|
| 40 V: 10 pulses vs. 1 pulse | <0.001 | 0.003 | Yes |
| 40 V: 5 pulses vs. 1 pulse | <0.001 | 0.004 | Yes |
| 40 V: 20 pulses vs. 1 pulse | <0.001 | 0.004 | Yes |
| 40 V: 10 pulses vs. 40 pulses | <0.001 | 0.004 | Yes |
| 40 V: 10 pulses vs. 3 pulses | <0.001 | 0.005 | Yes |
| 40 V: 20 pulses vs. 40 pulses | <0.001 | 0.005 | Yes |
| 40 V: 5 pulses vs. 40 pulses | <0.001 | 0.006 | Yes |
| 40 V: 20 pulses vs. 3 pulses | 0.003 | 0.006 | Yes |
| 40 V: 5 pulses vs. 3 pulses | 0.004 | 0.007 | Yes |
| 40 V: 3 pulses vs. 1 pulse | 0.079 | 0.009 | No |
| 40 V: 40 pulses vs. 1 pulse | 0.221 | 0.010 | No |
| 40 V: 10 pulses vs. 5 pulses | 0.234 | 0.013 | No |
| 40 V: 10 pulses vs. 20 pulses | 0.471 | 0.017 | No |
| 40 V: 3 pulses vs. 40 pulses | 0.575 | 0.025 | No |
| 40 V: 20 pulses vs. 5 pulses | 0.682 | 0.050 | No | iii) Pulse Duration

Using the 'Tandem' array configuration, the pulse was set at 40V, 1 or 5 pulses, and a range of pulse durations (0.1-400 ms) with appropriate gap durations (999.9-600 ms) (which=1 pulse/sec).

All pulse duration experiments other than 0.1 ms for 1 pulse produced significant CFE—mediated cell transformation (P<0.004; ranked ANOVA; Holm-Sidak multiple comparisons for 1 pulse; Mann-Whitney Rank Sum Test for 5 pulses, 0.1 ms; P=0.026). Cell transformation was maximum at 100 ms pulse duration. Five pulses produced significantly greater cell width (2 way ranked ANOVA, 10 ms-400 ms indicating a significant interaction between pulse number and pulse duration; P<0.001); FIG. 26, Table 8). While with a single pulse, there was no difference between 40 ms (38.3±5.1 cells), 100 ms (51.7±7.8 cells; n=6) and 400 ms (49.2±6.9 cells; n=6) (P>0.05; Holm-Sidak multiple comparisons), the 5 pulse treatment showed that 40 ms (147.2±12.4 cells) and 100 ms (211.7±16.6 cells) pulse durations produced significantly greater cell transformation (P=0.003; P<0.001). The 400 ms pulse duration with 5 pulses resulted in a 5.5 fold decline to 38.3±10.2 cells; n=6 per group) (P<0.001) (ranked 2 way ANOVA, Holm-Sidak multiple comparisons).

TABLE 4

Statistical Analysis for pulse duration with 40 V, 40 ms duration and with 1 pulse (n = 6/group) or 5 pulses (n = 6/group (except 40 P n = 9/group)), ranked two-way ANOVA with Holm-Sidak multiple comparisons.

| Comparison | Diff of Means | t | Unadjusted P | Critical Level | Significance |
|---|---|---|---|---|---|
| 1 P: 100 ms vs. 10 ms | 13.583 | 3.145 | 0.003 | 0.009 | Yes |
| 1 P: 400 ms vs. 10 ms | 12.750 | 2.952 | 0.005 | 0.010 | Yes |
| 1 P: 100 ms vs. 40 ms | 7.417 | 1.717 | 0.093 | 0.013 | No |
| 1 P: 400 ms vs. 40 ms | 6.583 | 1.524 | 0.135 | 0.017 | No |
| 1 P: 40 ms vs. 10 ms | 6.167 | 1.428 | 0.161 | 0.025 | No |
| 1 P: 100 ms vs. 400 ms | 0.833 | 0.193 | 0.848 | 0.050 | No |
| 5 P: 100 ms vs. 400 ms | 32.417 | 7.505 | <0.001 | 0.009 | Yes |
| 5 P: 40 ms vs. 400 ms | 26.722 | 6.777 | <0.001 | 0.010 | Yes |
| 5 P: 100 ms vs. 10 ms | 17.917 | 4.148 | <0.001 | 0.013 | Yes |
| 5 P: 10 ms vs. 400 ms | 14.500 | 3.357 | 0.002 | 0.017 | Yes |
| 5 P: 40 ms vs. 10 ms | 12.222 | 3.100 | 0.003 | 0.025 | Yes |
| 5 P: 100 ms vs. 40 ms | 5.694 | 1.444 | 0.156 | 0.050 | No |

| Comparison | Diff of Means | t | Unadjusted P | Critical Level | Significance |
|---|---|---|---|---|---|
| Comparisons for factor: pulse no within 10 ms | | | | | |
| 5 p vs. 1 p | 21.000 | 4.862 | <0.001 | 0.050 | Yes |
| Comparisons for factor: pulse no within 40 ms | | | | | |
| 5 p vs. 1 p | 27.056 | 6.862 | <0.001 | 0.050 | Yes |
| Comparisons for factor: pulse no within 100 ms | | | | | |
| 5 p vs. 1 p | 25.333 | 5.865 | <0.001 | 0.050 | Yes |
| Comparisons for factor: pulse no within 400 ms | | | | | |
| 1 p vs. 5 p | 6.250 | 1.447 | 0.155 | 0.050 | No | iv) Gap Duration

Using the 'Tandem' array configuration, the pulse was set at 40V, 2 or 5 pulses, 40 ms pulse duration, and a range of gap durations (50 ms, 100 ms, 250 ms, 500 ms and 1000 ms).

Immediately after electroporation, coverslips were placed in a humidity chamber for 2 mins. Coverslips were then placed in fresh, warmed media and returned to the incubator. At 48 hours post-electroporation, cells were fixed with 4% paraformaldehyde for 30 mins. The cells were then gently washed with phosphate-buffered saline (PBS) for 15 mins. Coverslips were then mounted on microscope slides with Prolong Gold with DAPI mounting medium (Life Technologies). The slides were left to cure at room temperature for 24 hours in a darkened box. Slides were then refrigerated and imaged as soon as possible. Cells were imaged using a confocal laser scanning microscope (Zeiss LSM 710) with a 2.5× objective. Transfected cells expressing GFP were manually counted from the captured images.

As shown in FIG. 27, there was no effect of gap duration on the level of cell transformation (2 pulses P=0.255, 5 pulses P=0.437; two-way ranked ANOVA; Holm-Sidak multiple comparisons). N=3/group (2P) N=5/group.

CONCLUSION

These studies demonstrate the efficacy of array-based electroporation for therapeutic transgene delivery to the cochlea, and show that a cochlear implant array provided site-specific control of the location and level of transgene expression. The efficacy of the gene therapy was demonstrated by reversal of somata atrophy and regeneration of lost peripheral neurites of the spiral ganglion neurons in the treated cochleae of deafened guinea-pigs.

It will be appreciated that, although specific embodiments of the invention have been described herein for the purpose of illustration, various modifications may be made without deviating from the spirit and scope of the invention as defined in the following claims.

The claims defining the invention are as follows:

1. A method of transfecting one or more cells within a target region with an agent by electroporation, said method comprising using a linear electrode array comprising at least eight electrodes contiguous in an array structure provided in a single probe introduced into a target treatment region such that there will be no tissue between the electrodes due to the array structure, the electrodes of the linear array configured as a single anode array comprising four or more neighbouring electrodes and a single cathode array comprising four or more neighbouring electrodes where the distance between the cathode array and the anode array is not more than 5 mm, exposing said one or more cells to said agent and applying an electroporation pulse profile to create a close electric field focused between the anode array and cathode array in a target region within millimetre or sub-millimetre dimensional space adjacent to the array in said target region for sufficient time to cause electroporation to allow at least some of said agent to enter said one or more cells, wherein each of said anode array and said cathode array independently comprise from 4 to 8 electrodes.

2. A method of transfecting one or more cells within a target region with an agent by electroporation, said method comprising using a linear electrode array comprising eight or more electrodes contiguous in an array structure provided in a single probe introduced into a target treatment region such that there will be no tissue between the electrodes due to the array structure, the electrodes of the linear array configured as a single anode array comprising four neighbouring electrodes and a single cathode array comprising four neighbouring electrodes where the distance between the cathode array and the anode array is not more than 5 mm, exposing said one or more cells to said agent and applying an electroporation pulse profile to create a close electric field focused between the anode array and cathode array in a target region within millimetre or sub-millimetre dimensional space adjacent to the array in said target region for sufficient time to cause electroporation to allow at least some of said agent to enter said one or more cells, wherein each of said anode array and said cathode array comprises 4 electrodes.

3. The method of claim 1, wherein the agent comprises a nucleic acid molecule which on entering said one or more cells enables said one or more cells within said target region to produce, enhance or suppress an activity within said region.

4. The method of claim 1, wherein the agent comprises a nucleic acid molecule which on entering said one or more cells at least partially restores physiological function within said target region, one or more regions annexing said target region, or both within said target region and one or more regions annexing said target region.

5. The method of claim 1, wherein the agent comprises a nucleic acid molecule.

6. The method of claim 5, further characterised by any one of:
    the nucleic acid molecule encodes a neurotrophic factor,
    the nucleic acid molecule encodes a transcription factor which modulates the expression of a neurotrophic factor, or
    the nucleic acid molecule decreases the expression of a transcription factor, wherein the transcription factor modulates the expression of a neurotrophic factor.

7. The method of claim 6, wherein the neurotrophic factor is selected from any one of Neurotrophin-3, Neurotrophin-3 precursor molecule, Neurotrophin 4/5, Nerve growth factor, Brain-derived neurotrophic factor, glial cell line-derived neurotrophic factor, ciliary neurotrophic factor and Activity dependent neurotrophic factor.

8. The method of claim 1, wherein said anode array and said cathode array are separated by between about 10 μm and about 5 mm.

9. The method of claim 8, wherein said anode array and said cathode array have a length of 0.35 mm to 2.5 mm.

10. The method of claim 1, wherein said anode array and said cathode array are separated by at least 10 μm.

11. The method of claim 1, wherein a voltage applied between said anode array and said cathode array is about 1V to about 40V.

12. The method of claim 1, wherein a total electric charge delivered during said electroporation is less than 0.5 Coulombs, optionally less than 0.1 Coulombs, more optionally less than 0.05 Coulombs.

13. The method of claim 12, wherein the total electric charge is delivered through less than 100 electric pulses, optionally through 10 or fewer pulses, 5 or fewer pulses, 4 pulses, 3 pulses, 2 pulses or 1 pulse.

14. The method of claim 13, wherein each pulse is from about 100 μs to about 500 ms in duration.

15. The method of claim 1, wherein said anode array and said cathode array are provided on a cochlear implant electrode array.

16. The method of claim 2, wherein said anode array and said cathode array are separated by at least 10 μm.

17. The method of claim 2, wherein a voltage applied between said anode array and said cathode array is about 1V to about 40V.

18. The method of claim 2, wherein a total electric charge delivered during said electroporation is less than 0.5 Coulombs, optionally less than 0.1 Coulombs, more optionally less than 0.05 Coulombs.

19. The method of claim 18, wherein the total electric charge is delivered through less than 100 electric pulses, optionally through 10 or fewer pulses, 5 or fewer pulses, 4 pulses, 3 pulses, 2 pulses or 1 pulse.

20. The method of claim 19, wherein each pulse is from about 100 μs to about 500 ms in duration.

* * * * *